(12) United States Patent
Dahm

(10) Patent No.: US 7,863,641 B2
(45) Date of Patent: *Jan. 4, 2011

(54) METHOD AND APPARATUS FOR USING LIGHT EMITTING DIODES FOR THE TREATMENT OF BIOLOGICAL TISSUE

(76) Inventor: Jonathan S. Dahm, 131 Pirates Dr., Key Largo, FL (US) 33037

( * ) Notice: Subject to any disclaimer, the term of this patent is extended or adjusted under 35 U.S.C. 154(b) by 0 days.

This patent is subject to a terminal disclaimer.

(21) Appl. No.: 11/974,432

(22) Filed: Oct. 12, 2007

(65) Prior Publication Data
US 2008/0094841 A1    Apr. 24, 2008

Related U.S. Application Data

(63) Continuation of application No. 10/979,903, filed as application No. PCT/US03/26553 on Aug. 25, 2003, now Pat. No. 7,345,320.

(60) Provisional application No. 60/405,432, filed on Aug. 23, 2002, provisional application No. 60/410,720, filed on Sep. 13, 2002, provisional application No. 60/416,948, filed on Oct. 8, 2002, provisional application No. 60/420,479, filed on Oct. 22, 2002, provisional application No. 60/467,702, filed on May 3, 2003, provisional application No. 60/476,004, filed on Jun. 4, 2003.

(51) Int. Cl.
*H01L 33/00* (2006.01)

(52) U.S. Cl. .................. 257/99; 257/276; 257/625; 257/675; 257/706; 257/720; 257/E23.101

(58) Field of Classification Search .................. 257/99, 257/276, 625, 675, 706, 717, 720, 796, E23.101
See application file for complete search history.

(56) References Cited

U.S. PATENT DOCUMENTS

| | | | | |
|---|---|---|---|---|
| 5,631,987 | A * | 5/1997 | Lasky et al. | 385/88 |
| 5,729,561 | A * | 3/1998 | Hironaka | 372/36 |
| 7,345,320 | B2 * | 3/2008 | Dahm | 257/99 |
| 2001/0046652 | A1 * | 11/2001 | Ostler et al. | 433/29 |

* cited by examiner

*Primary Examiner*—Tan N Tran
(74) *Attorney, Agent, or Firm*—Emery L. Tracy

(57) ABSTRACT

The present invention provides a method and apparatus for using light emitting diodes for curing and various solid state lighting applications. The method includes a novel method for cooling the light emitting diodes and mounting the same on heat pipe in a manner which delivers ultra high power in UV, visible and IR regions. Furthermore, the unique LED packaging technology of the present invention utilizes heat pipes that perform very efficiently in very compact space. Much more closely spaced LEDs operating at higher power levels and brightness are possible because the thermal energy is transported in an axial direction down the heat pipe and away from the light-emitting direction rather than a radial direction in nearly the same plane as the "p-n" junction.

10 Claims, 79 Drawing Sheets

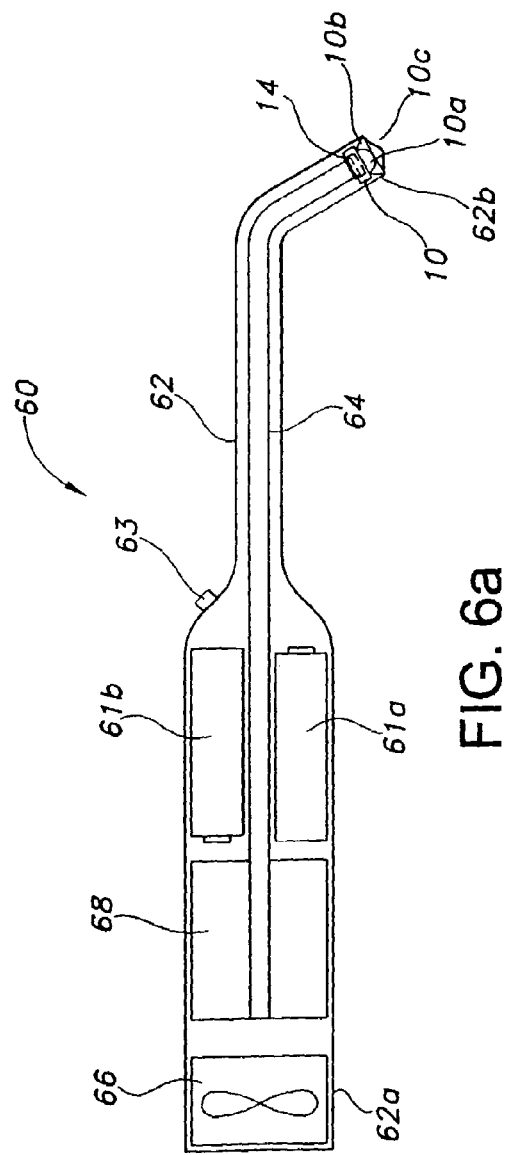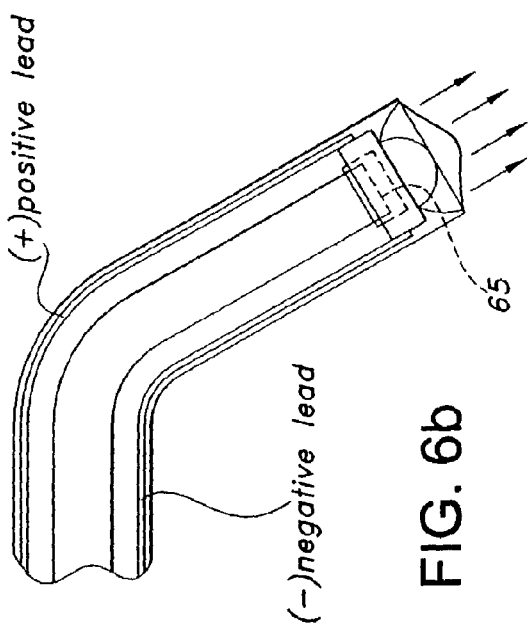

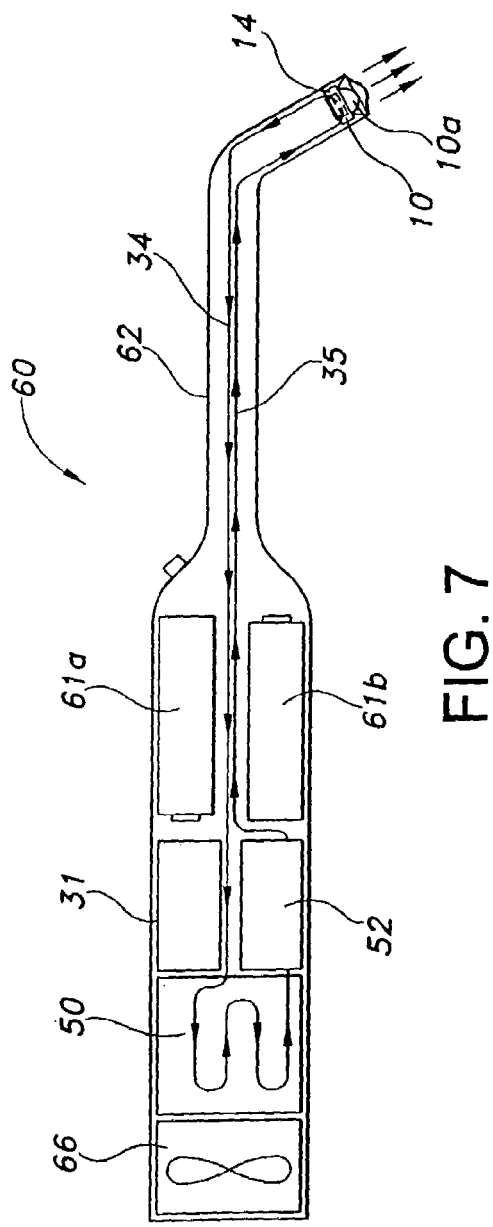
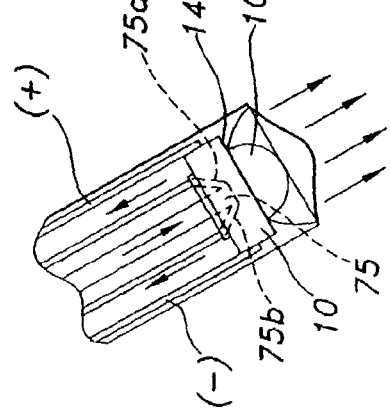
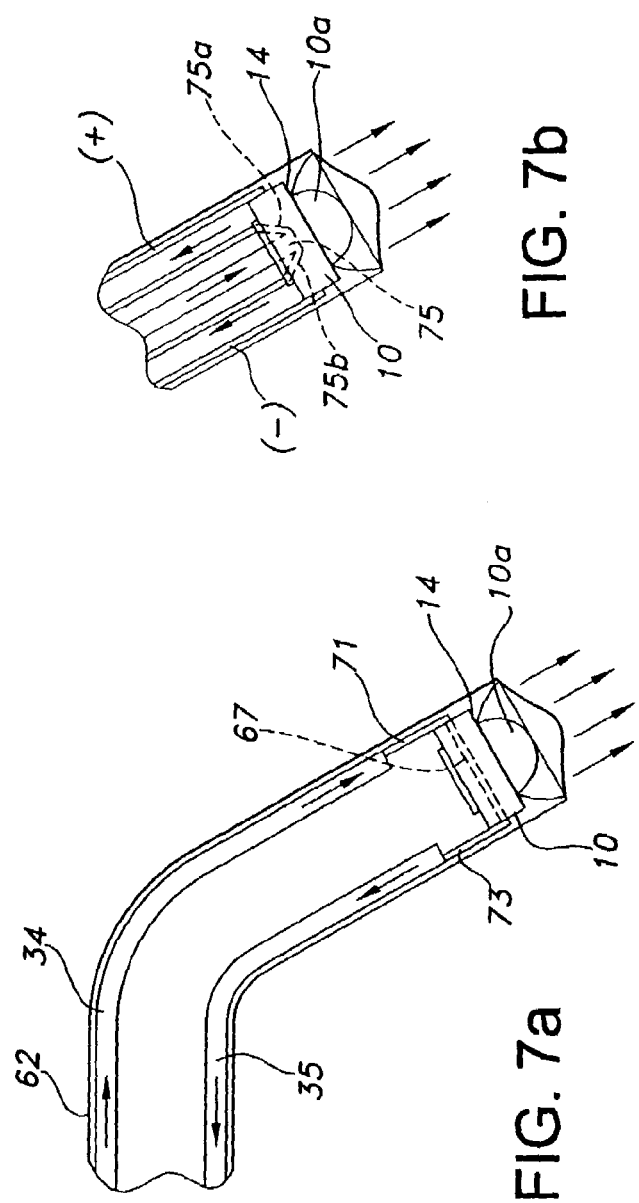
FIG. 7
FIG. 7a
FIG. 7b

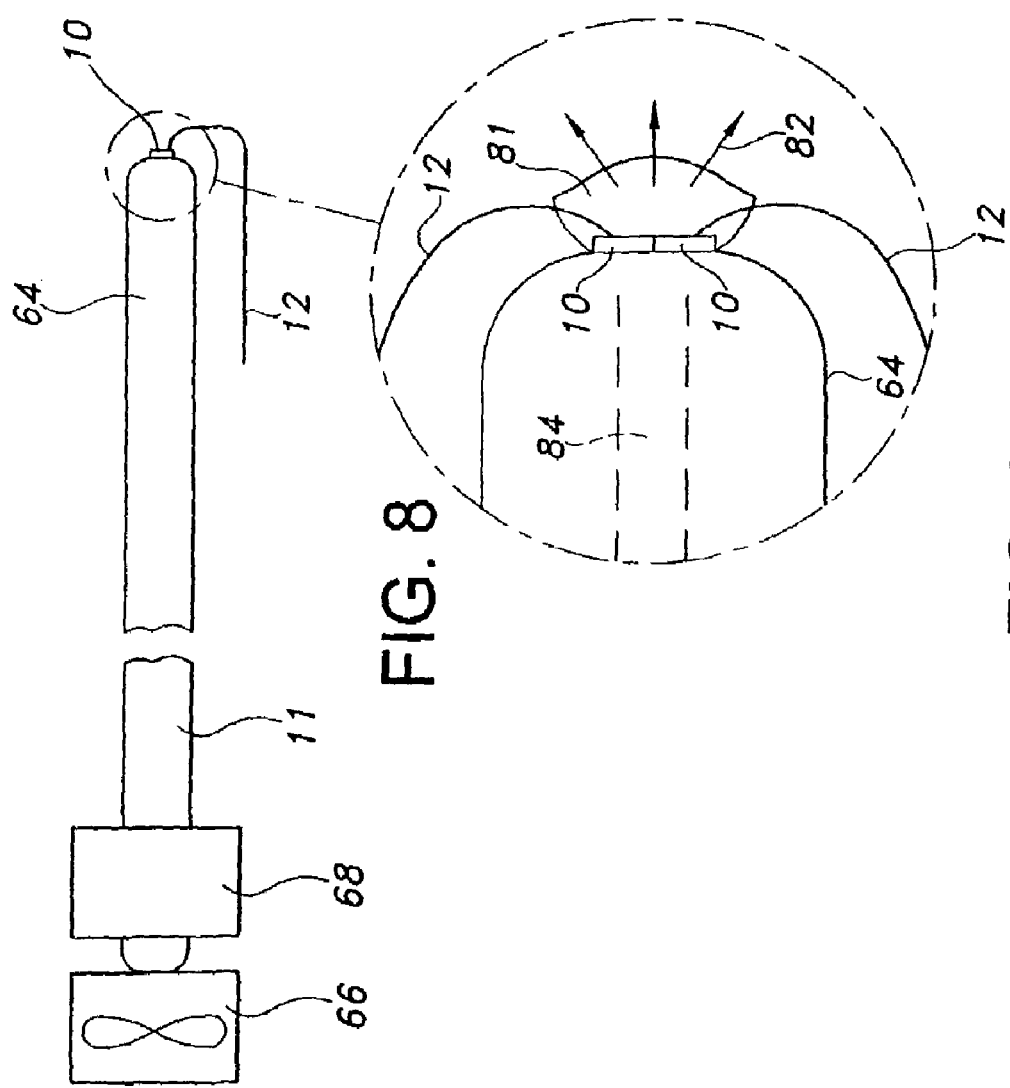

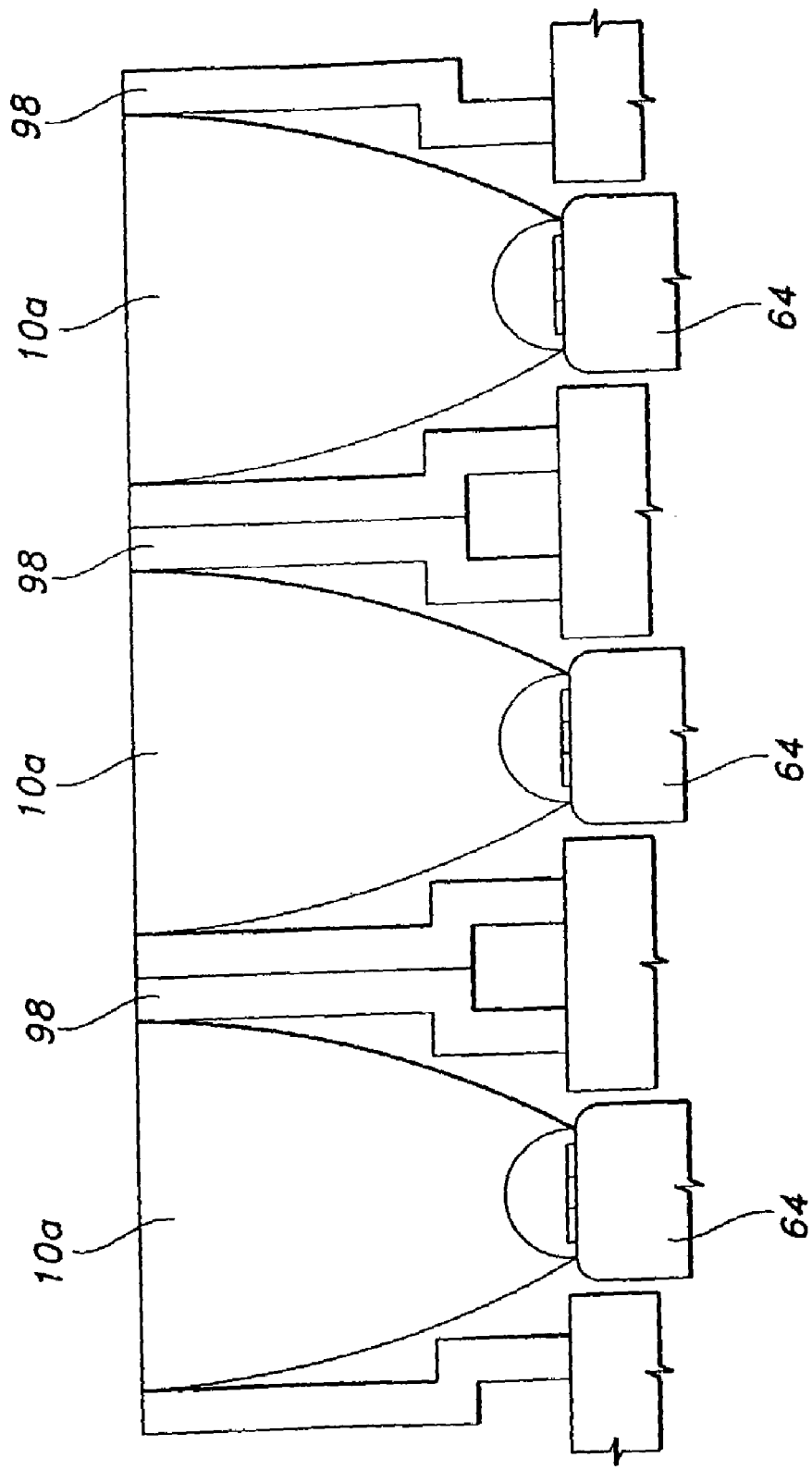

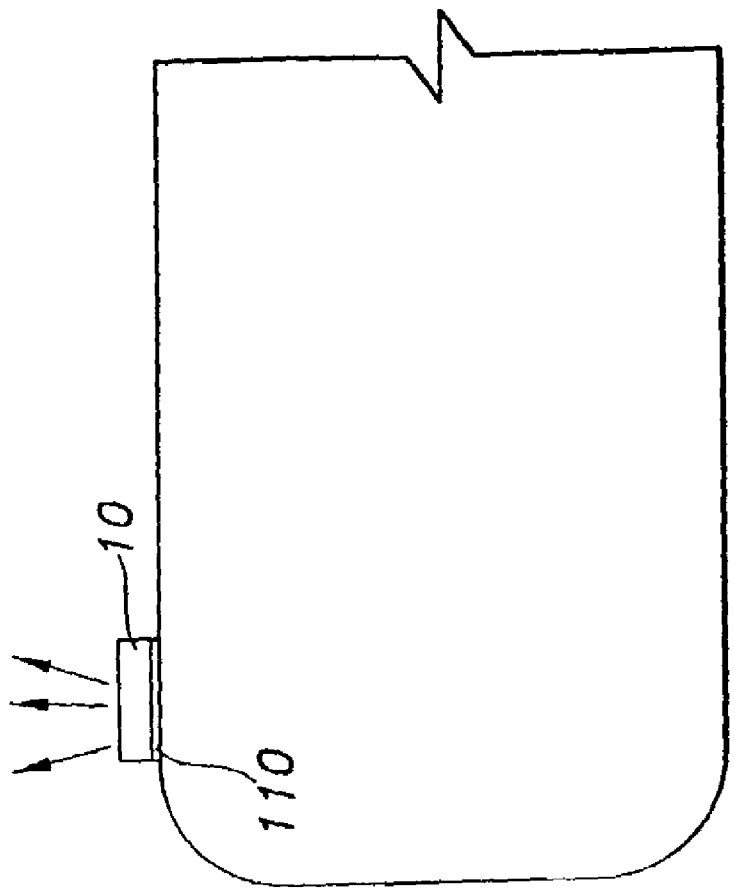
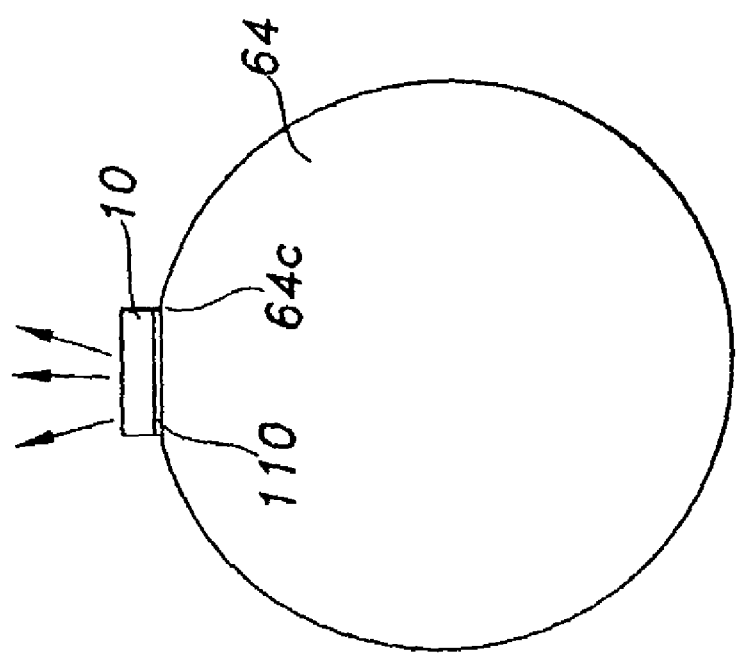
FIG. 18a
FIG. 18b

METHOD AND APPARATUS FOR USING LIGHT EMITTING DIODES FOR THE TREATMENT OF BIOLOGICAL TISSUE

CROSS REFERENCE TO RELATED APPLICATIONS

This application is a continuation and claims benefit of priority of pending U.S. patent application Ser. No. 10/979,903, filed Nov. 2, 2004, now U.S. Pat. No. 7,345,320 which claims benefit of priority of PCT Patent Application No. PCT/US2003/026553, filed Aug. 25, 2003, U.S. Provisional Application Nos. 60/405,432, filed Aug. 23, 2002; 60/410,720, filed Sep. 13, 2002; 60/416,948, filed Oct. 8, 2002; 60/420,479, filed Oct. 22, 2002; 60/467,702, filed May 3, 2003 and 60/476,004, filed on Jun. 4, 2003.

FIELD OF THE INVENTION

This invention relates to the field of light emitting diode ("LED") technology, particularly to improvement in light-emitting devices by integration of novel packaging methodologies to make much higher output LED devices.

BACKGROUND OF THE INVENTION

Heat can damage sensitive electronic components, degrading reliability and hampering the ability to concentrate higher power levels into smaller packages. Many applications would benefit from the ability to closely package LEDs into compact configurations, but the heat levels generated have always been a limiting factor. As LEDs become more sophisticated, eliminating internal heat buildup has also become increasingly difficult. Devices are becoming more powerful and creating solutions for removing the resulting heat generation often pose great challenges. The drive current through an LED must be controlled. High current densities within the junction of the chip cause partial overheating which damages the crystalline structure of the LED die. At these areas are so called dark line defects, where light ceases to be generated. By rapidly transporting heat away from the junction, dark line defect generation can be reduced or eliminated.

U.S. Patent Publication No. 2003/0036031 to Lieb et al. discloses a light-emitting headpiece for curing light-curable dental resins and similar materials. The device includes a head portion for supporting a LED light source, a tubular handle portion for containing a power source for energizing the LED light source and a nook portion that interconnects the head and handle portions. The head and the neck portions are integrally formed from a common, thermally conductive material and operate to provide a heat sink for the LED. A substantial portion of the light source housing itself functions to dissipate sufficient thermal energy away from the LED allowing the LED to be operated for a time interval sufficient to effect rosin curing.

In U.S. Patent Publication No. 2003/00213 to Herold et al, there is disclosed a method and apparatus for cooling electronic or opto-electronic devices. The apparatus includes the device mounted on a heat sink assembly within a can having a can body and a can header thermally coupled to the heat sink assembly and closing the can body and a thermal conductor outside the can and having a first portion attached to at least part of an edge of the can header and a second portion attached to a thermal sink outside the can.

In U.S. Pat. No. 6,159,005 to Herold et al., there is disclosed a small, light-weight handy device for photo polymerizing synthetic materials. The device includes a built-in battery, a light source constituted by an LED which emits a small useful spectral range only, thereby avoiding any heat radiation. The LED is preferably located at the tip of the device directed towards the site to be polymerized.

In U.S. Pat. No. 6,523,959 to Lu et al., there is disclosed a cooling device to cool a liquid crystal panel and polarizer of an optical system in a liquid crystal projector. The cooling device includes a heat dissipation system comprising a plurality of heat pipes disposed at the two flank sides of said liquid crystal panel.

In U.S. Pat. No. 6,113,212 to Ng et al., there is disclosed a method and apparatus for thermal control of LED print heads using heat pipes to transfer the heat from the LEDs to a heat sink. In this apparatus the LEDs are emitting in a direction that is perpendicular to the axis of the vapor cavity (within the heat pipe) and the LEDs are shown to be mounted, not at the very tip of the heat pipe, but some distance back from the tip mounted on a heat sink as well.

It is believed that none of these U.S. patent documents disclose LEDs on the tips of heat pipes and cooling in a manner to dissipate internal heat energy and packaging the same to achieve maximum light output. A need exists for cooling the LEDs and mounting the same on the heat pipes in a manner which greatly surpasses the performance of conventional cooling techniques and benefit high density, miniaturized LED components. Furthermore, there is a need for a novel LED packaging technology that channels heat away via state-of-the-art micro heat pipes that perform far more efficiently, and in much more compact space, than conventional heat sink technology. Use of heat pipe and LED configurations claimed in this patent application allows the heat to be transported down the heat pipe in an axial direction away from the direction of light propagation. This is in contrast to conventional heat spreaders or heatsinks which transports heat from the die in a radial direction away from it. This prevents close spacing of LED components due to the high thermal energy in a confined area.

SUMMARY OF THE INVENTION

In a first embodiment, the present invention is an apparatus for transporting thermal energy. The apparatus comprises at least one heat pipe with each heat pipe having a first end and a second end and a cavity extending from the first end to the second end. A light emitting device is mounted to the first end of each heat pipe with each light emitting device having a "p-n" junction wherein the axis of at least a portion of the vapor cavity intersects the plane of the "p-n" junction.

In a second embodiment, the present invention is a light emitting apparatus comprising a heat pipe having an evaporating end and a condensing end, a light emitting device mounted on the evaporating end of the heat pipe, and a cone of light emitting from the light emitting device wherein the light ray along the cone axis moves in a substantially parallel and opposite direction, a substantially perpendicular direction, or a direction between substantially parallel and opposite and substantially perpendicular to the thermal energy moving along at least a portion of the vapor cavity axis.

In a third embodiment, the present invention is an apparatus comprising an electrically conductive heat pipe and a light emitting device mounted on a tip of the heat pipe wherein the heat pipe provides electricity for the light emitting device and transports heat from the light emitting device.

In a fourth embodiment, the present invention is a light emitting device. The device comprises a substrate having at least one heat pipe and a light emitting device mounted on the substrate wherein heat generated by the light emitting devices travels in a substantially opposite direction from light emitted.

In a fifth embodiment, the present invention is a device for providing light in a predetermined direction. The hand held device comprises a heat pipe with the heat pipe having a first and a second end. A light emitting device is mounted at the first end of the heat pipe. A power supply powers the light emitting device. An activation switch activates the power supply and a hand held housing surrounds at least a portion of the second end of the heat pipe.

In an sixth embodiment, the present invention is a method for curing adhesives on a surface. The method comprises providing at least one light emitting diode mounted to the end of a heat pipe and irradiating said adhesive on said surface with said light emitting diode to cure said adhesive.

In a seventh embodiment, the present invention is a device for curing adhesives on a surface. The device comprises a power supply and a radiation source coupled to said power supply with said radiation source having a radiation output and including at least one light emitting diode mounted to the tip of at least one heat pipe.

In an eighth embodiment, the present invention is a light emitting diode curing device. The device comprises a tubular body having two opposed ends, a wide end and a tip end. A light emitting diode body placed at the tip end with the light emitting diode body having a conductive surface. A heat pipe extends through the tubular body and contacts the conductive surface of the light emitting diode body. A power source is located within the tubular body for powering the light emitting device wherein at least a portion of the tubular body functions as a heat sink.

In a ninth embodiment, the present invention is an apparatus for transporting heat. The apparatus comprises at least one heat pipe with each heat pipe having a first end and a second end. A light emitting device is mounted at the first end of each heat pipe wherein heat generated by each light emitting device is transported in a general direction away from each light emitting device toward the second end of the respective heat pipe.

In a tenth embodiment, the present invention is a device comprising a first circuit layer having a first aperture and a conductive heat spreader layer. The heat spreader is receivable within the aperture of the first circuit layer. At least one light emitting device is secured to the heat spreader layer. A second circuit layer is mounted on the first circuit layer with the second circuit layer having a second aperture for receiving each light emitting device. Circuit traces are formed on the second circuit layer and means for connecting the circuit traces to each light emitting device. The surface area of the conductive patterned circuit material layer can be greater than the surface area of the conductive patterned heat spreader layer.

In an eleventh embodiment, the present invention is a device for directing light energy comprising a transparent media with a refractive index greater than one and a concavity in the transparent media to accept at least one LED. An encapsulating media within the concavity at least partially covers at least one surface of the LED wherein the LED light emits into the transparent media through encapsulating media wherein said light energy is substantially internally reflected by the refractive index difference of the transparent media and air boundary.

BRIEF DESCRIPTION OF THE DRAWINGS

FIG. 6a shows a perspective view of a hand held LED curing device according to the present invention.

FIG. 6b is an expanded view of the tip end of the device in FIG. 6a.

FIG. 7 illustrates a perspective view of a liquid-cooled version of the LED hand held curing device according to the present invention.

FIG. 7a is an expanded view of the front end of the device in FIG. 7

FIG. 7b is an expanded view of the tip end of the device in FIG. 7.

FIG. 8 shows an LED curing device in which heat pipe provides both coolant and electrical connection according to an alternate embodiment of the present invention.

FIG. 8a shows an expanded view of the tip of the device of FIG. 8 with multiple LEDs.

FIG. 14a is a cross-sectional view of the arrayed devices of FIG. 14.

FIGS. 18a, 18b, 18c, 18d and 18e show a perspective view of LED mounted onto various portions of the heat pipe.

FIG. 24 illustrates the LED array assemblies of FIG. 22g being inserted into the circuit board assembly of FIG. 23a.

DETAILED DESCRIPTION OF THE INVENTION

Figure 1A:
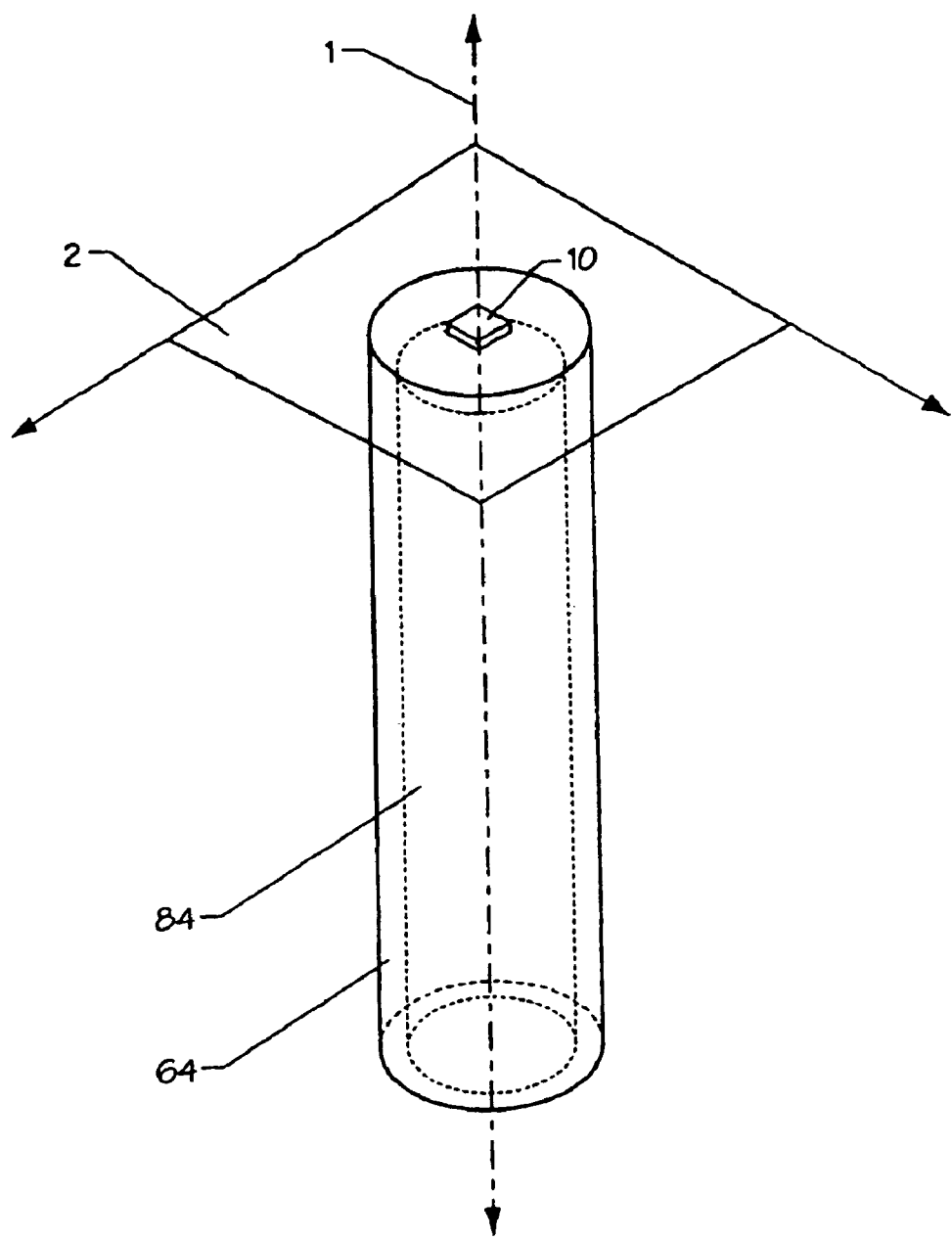
FIG. 1a illustrates a heat pipe vapor cavity axis intersecting plane of "p-n" junction.

The present invention provides high power LEDs and heat pipe technology which allows for ultra-high power density packaging. The ultra-high thermal conductivity of the heat pipe allows for over-driving the LEDs by a factor of 4×, while maintaining junction temperatures well within rated limits. Other attributes include low thermal resistance submount, brightness-maintaining TIR reflector, low cross-sectional area heat sink, and individually addressable high-density chip array. These attributes facilitate the ability to achieve high power densities, even without integral heat pipes, which is especially useful for those applications that do not demand ultra-high thermal performance.

The manner of bonding of the LED device to the heat pipe component as in the present invention minimizes the physical space requirements while taking advantage a pipes' unique rapid heat dissipation capabilities. This allows much more closely spaced LEDs operating at higher power and brightness. Some other features of this heat pipe packaging for LED components include rapid thermal response, variable heat flux, light weight, high reliability and requires little or no maintenance.

In one aspect of the present invention, there is provided a novel means of cooling the light emitting devices preferably at least one LED or resonant cavity LED ("RDLED") or superluminescent LED ("SLLED") or organic LED ("OLED") or flexible OLED ("FOLED") or Flip Chip LED ("FCLED"), or vertical cavity surface emitting laser ("VCSEL"). For the purpose of the invention, we will refer to the LED, however, it is to be understood that other light emitting devices mentioned or known in the art can be used as well.

Wavelengths from 100 nm to 11,000 nm may be used. The most preferable wavelength range is 250 nm to 5,000 nm in the instant invention. Most preferably wavelengths from 35 nm to 900 nm are used.

FIG. 1 shows a tubular heat pipe 64 with the axis 1 of the vapor cavity 81 shown down the center of the heat pipe 64. LED 10 is shown mounted to the tip of the heat pipe. Tip can mean the center end face portion of the heat pipe 64 as shown in FIG. 1*a*, or it might mean the region around the outer wall of the heat pipe and within five heat pipe diameters in length from the very end of the evaporating end of a heat pipe. The LED 10 has a "p-n" junction and this junction forms a plane, the extended plane 2 shown in the drawing. Note how the extended vapor cavity axis 1 intersects the extended plane 2 of the "p-n" junction.

Figure 1B:
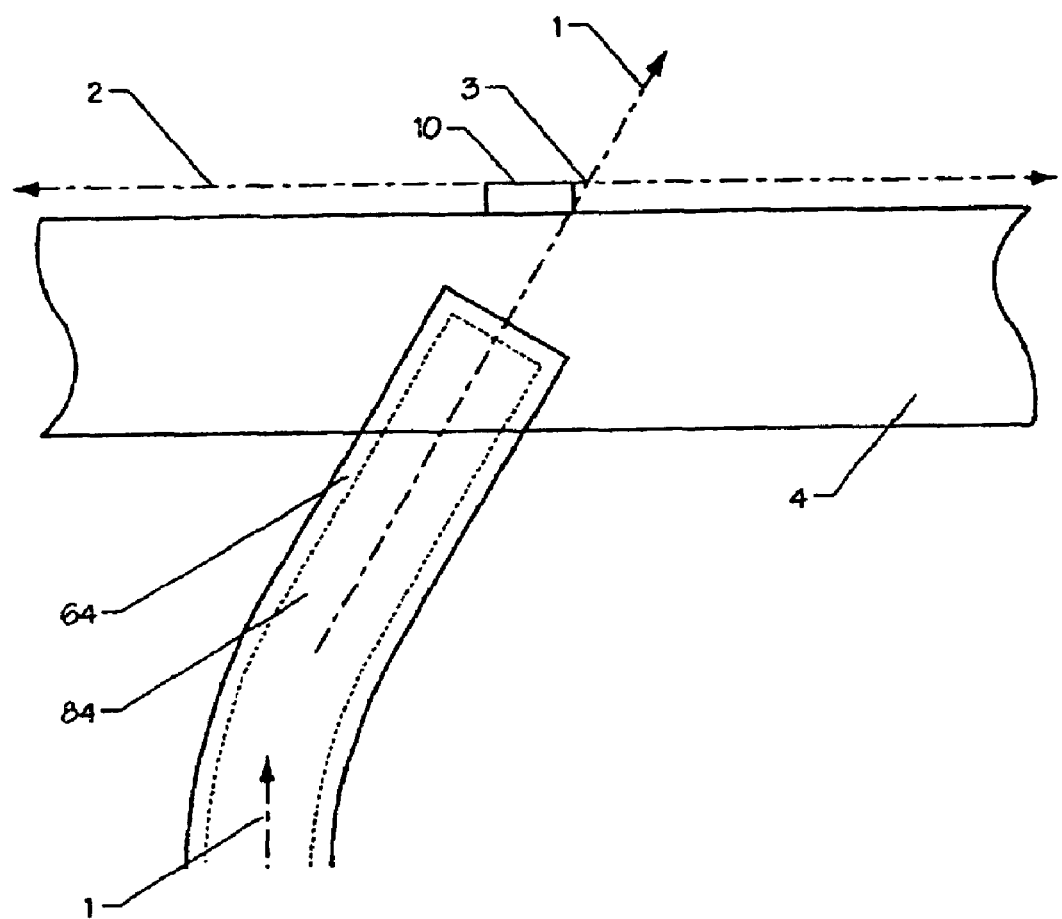
FIG. 1b. illustrates a heat pipe inserted into a heat spreader with vapor cavity axis and "p-n" junction plane shown.

FIG. 1*b* shows the heat pipe 64 inserted into heat spreader 4. The heat spreader 4 can also be called a heatsink, a submount, or a substrate. LED 10 is shown with the plane 2 of the "p-n" junction and the vapor cavity axis 1 intersecting junction plane 2 at point 3. It is understood that any embodiment may have a "p-n" junction containing quantum dots.

Figure 1C:
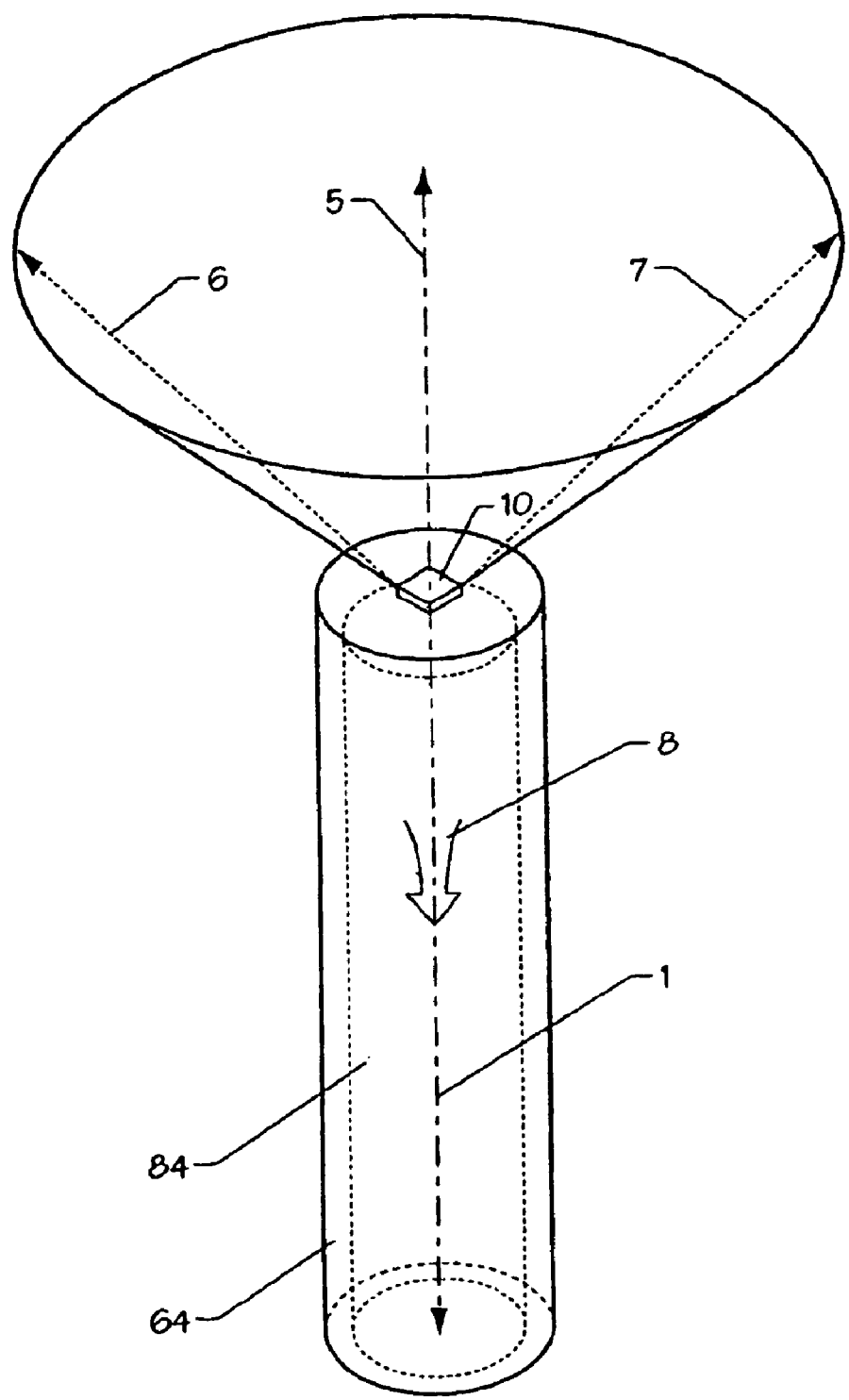
FIG. 1c shows a LED light conical emission with its optical axis co-axial to heat pipe axis.

FIG. 1*c* shows LED 10 mounted on the tip of heat pipe 64. Vapor cavity 84 is shown with vapor cavity axis 1. Optical axis 5 is shown and is the effective light center of the LED 10. The optical axis 5 can also be called the cone axis. The optical axis 5 can be a light ray as are light rays 6 and 7 that are part of a rotationally symmetric "cone of light" emitting from LED 10. The optical radiation pattern of most LEDs is rotationally symmetric about the optical axis. Because the LED chip 10 itself has a physical size and is not a point source, the emitted light does not appear to come from a single location, but a range of locations or a focal smear. The center point of the focal smear should be chosen as the origin of the optical axis 5. Again, the optical axis 5 is shown in FIG. 1*c* also as a light ray emitting from the center of LED 10. If an array of LEDs were shown, the optical axis 5 would be at the center of the focal smear when all of the emitting light from all of the LEDs are considered as a whole. Thermal energy (or heat) 8 is shown moving opposite to the direction of the optical axis 5 light ray and also moving parallel to the vapor cavity axis 1. The optical axis 5 of LED 10 is preferably coaxial with the vapor cavity axis 1.

Figure 1D:
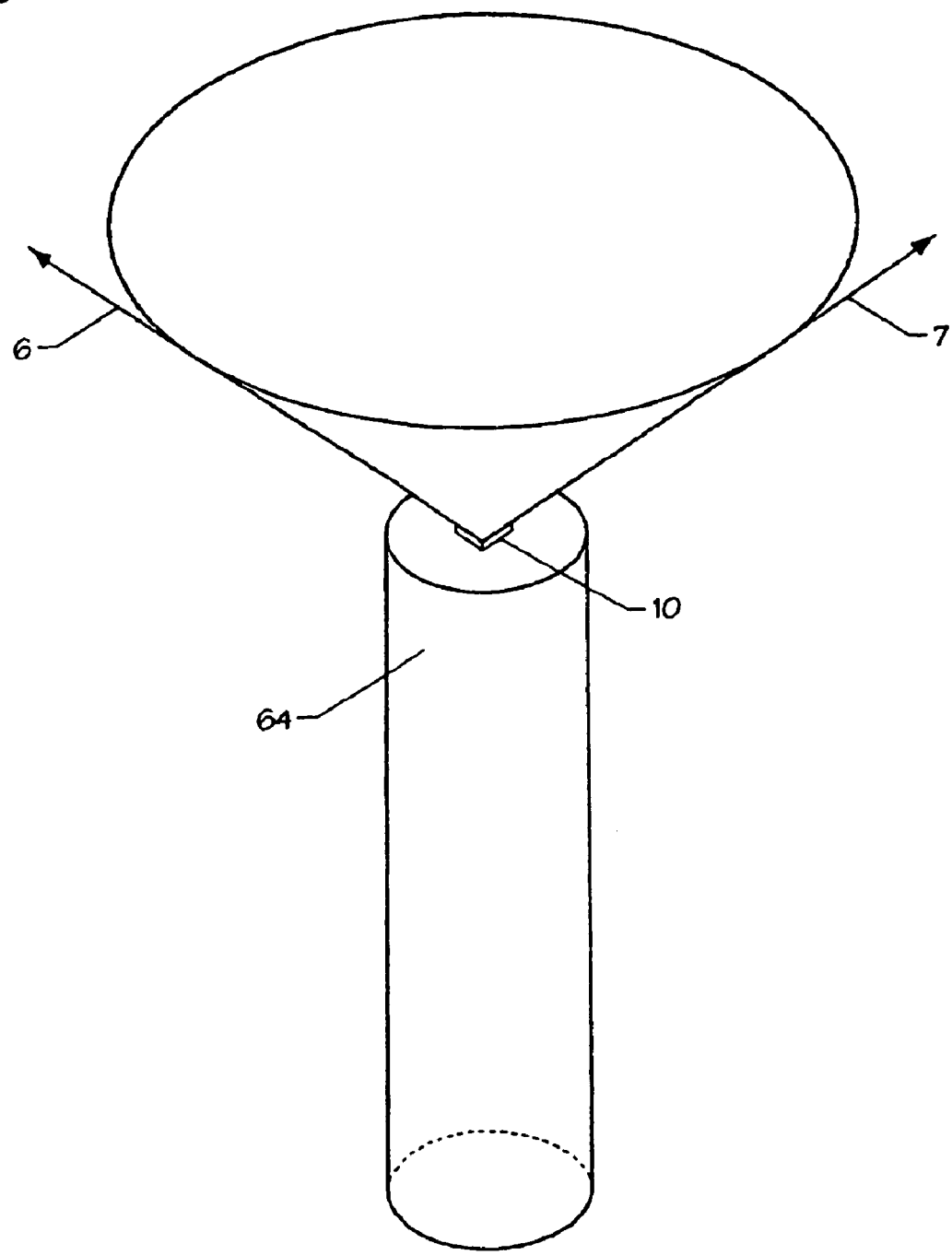
FIG. 1d shows a shaded region of LED light emission and LED on end of heat pipe.

FIG. 1*d* shows a solid model of the cone of light partially bounded by light rays 6 and 7 emitting from LED 10. LED 10 is mounted to the tip of heat pipe 64.

Figure 2A:
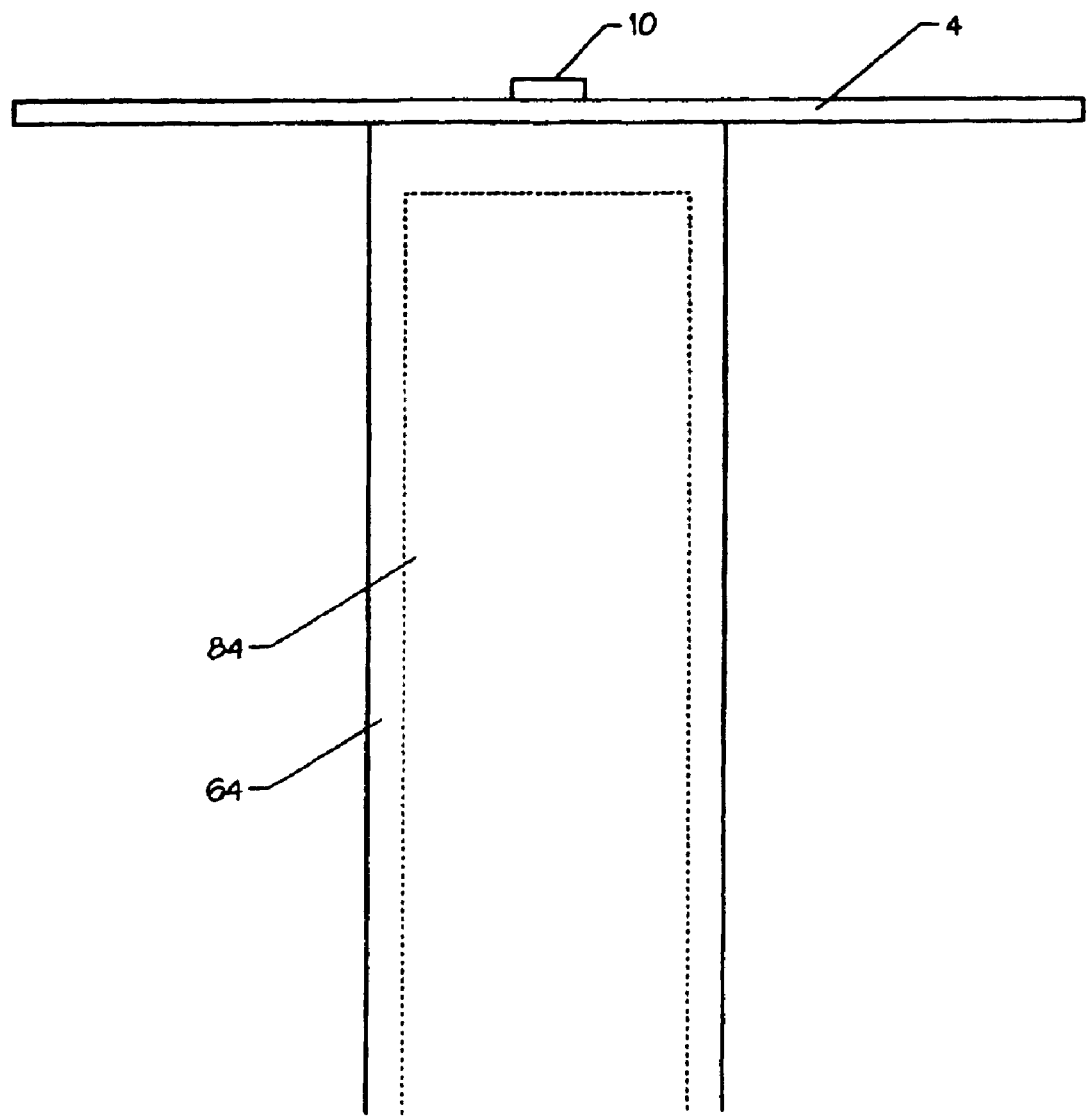
FIG. 2a shows a side view of a heat pipe with a heat spreader mounted flush with the tip of the heat pipe.

FIG. 2*a* shows heat pipe 64 with vapor cavity 84 and an LED 10 mounted on heat spreader 4 which is also mounted on the tip of heat pipe 64.

Figure 2B:
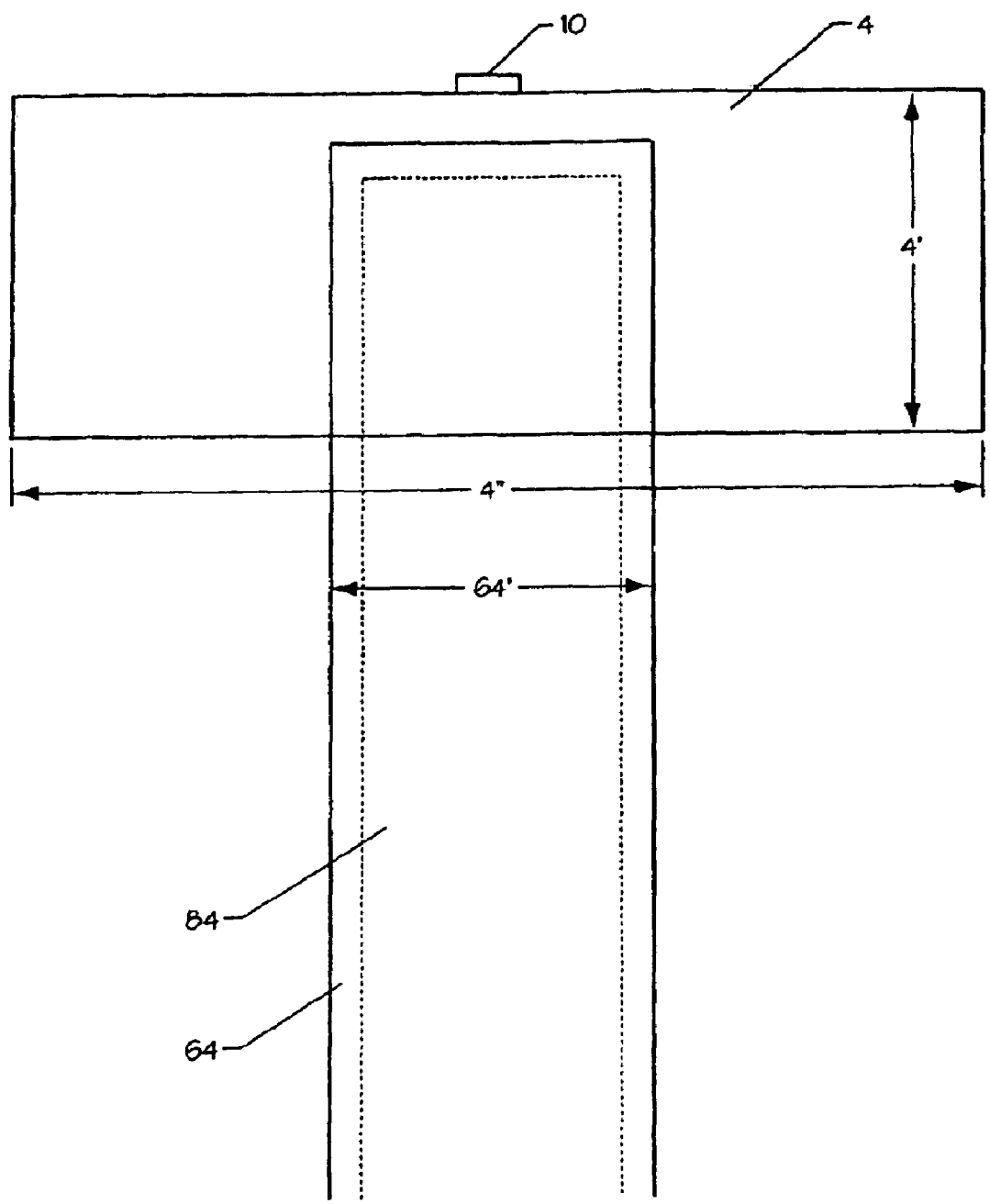
FIG. 2b is a side view of a heat pipe inserted into a heat spreader.

FIG. 2*b* shows a cross-sectional view of heat spreader 4 with the heat pipe embedded in it. The thickness 4' of this heat spreader 4 can be related to the diameter 64' of the heat pipe 64. In the preferred embodiment, the heat spreader thickness is less than one diameter 64' of the heat pipe 64. Also, the length, diameter, or width 4" of heat spreader 4 is preferably less than five times diameter 64' of heat pipe 64 and most preferably less than one diameter 64'. The area of the side of the heat spreader 4 that the LED is bonded to is preferably less than the diameter cross-sectional area of the heat pipe 64. Also, the area of the "p-n" junction is preferably less than the diameter cross-sectional area of the heat pipe 64.

Figure 2C:
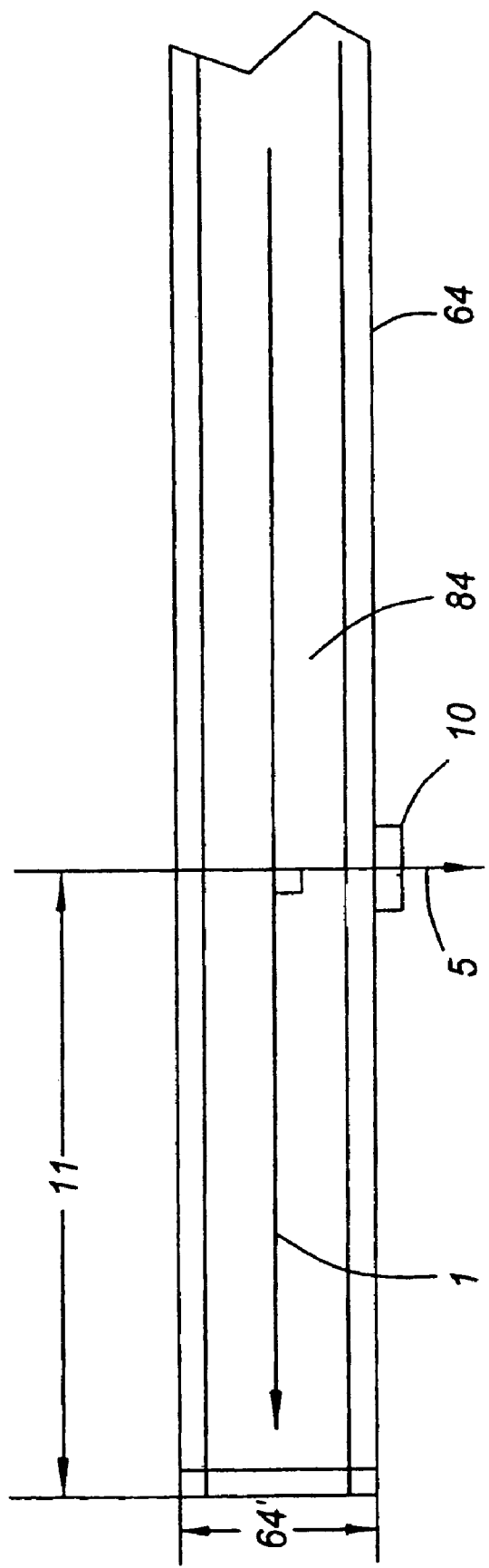
FIG. 2c shows a heat pipe with an LED mounted on the side of the heat pipe near the tip.

FIG. 2*c* shows a heat pipe 64 with vapor cavity 84 and LED 10. The diameter 64' of heat pipe 64 is depicted, and length 11 is shown and corresponds to the distance of the center of LED 10, which is the furthest LED (if multiple LEDs are mounted to heat pipe 64). The length 11 is preferably no more than five times the diameter 64' of heat pipe 64. It is most preferably less than two times diameter 64'. It is understood that by mounting an LED 10 on the side of a heat pipe 64, devices may be configured to get light into confined areas. A hand held curing device could be designed with a chip on the side of a heat pipe to cure coatings on teeth in the confined space between teeth and cheek. The optical axis 5 is perpendicular to the vapor axis 1.

Figure 3A:
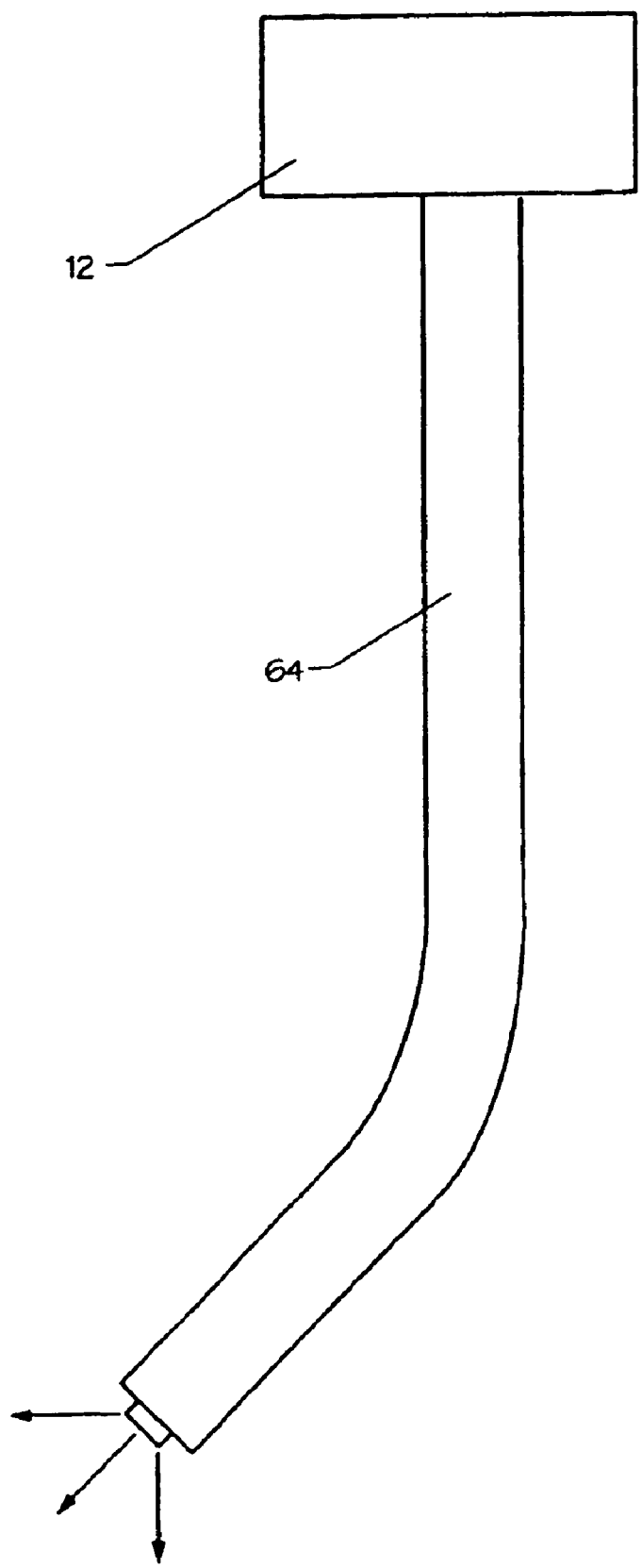
FIG. 3a is a solid state lighting device wherein the heat pipe is mounted in a block that may, in turn be mounted to a wall.

FIG. 3*a* depicts a specialty light application wherein heat pipe 64 is shown with LED 10 mounted at its tip. The arrows depict the direction of light emission. Block 12 may be mounted to a wall or ceiling and not only anchors the heat pipe 64 but also may serve as a heatsink of heat spreader. The block 12 may also be a junction box located in a wall or ceiling. The heat pipe 64 may or may not carry current.

Figure 3B:
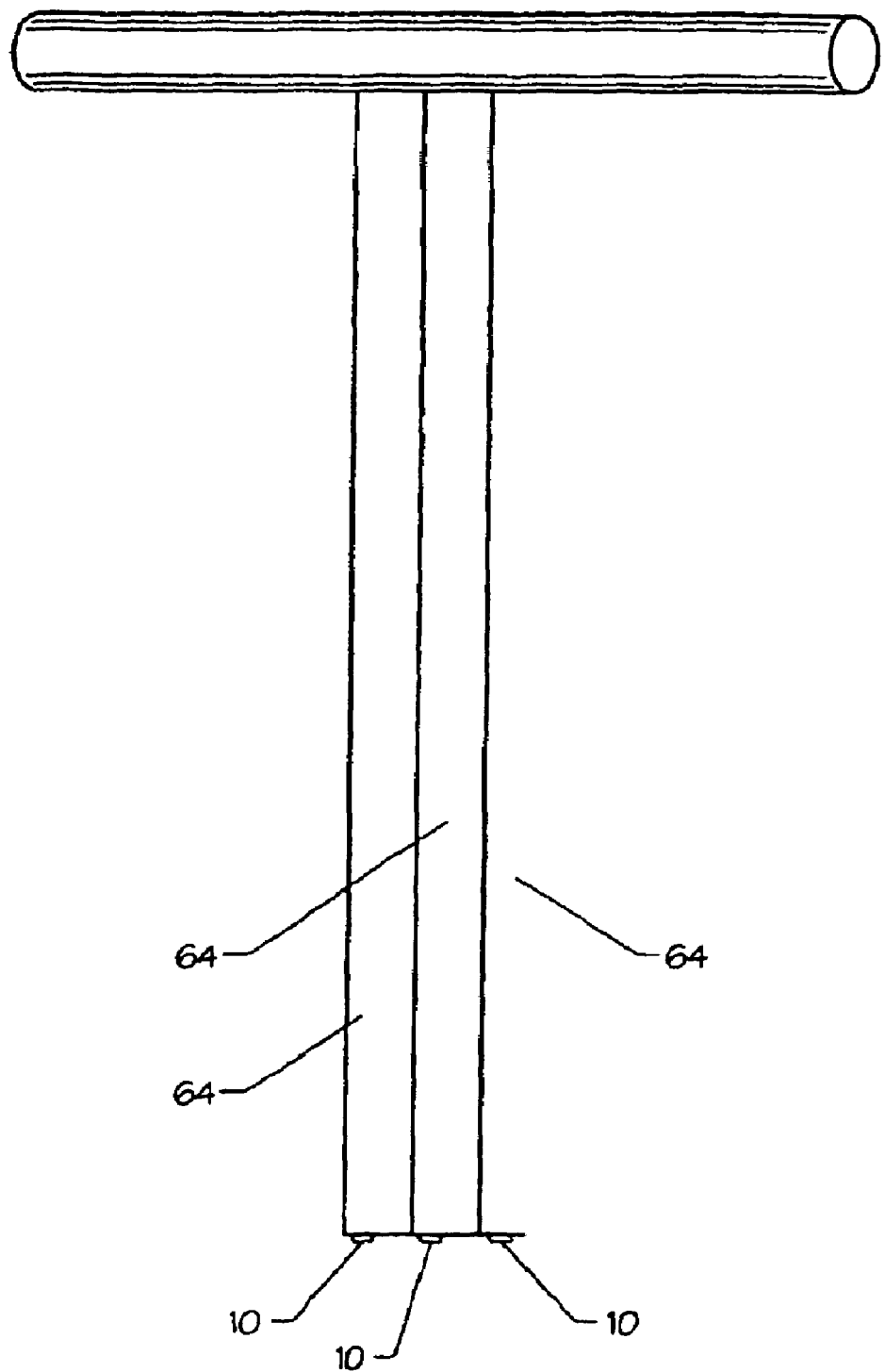
FIG. 3b illustrates a track lighting view with three heat pipes with LEDs on the tips and all three heat pipes are mounted in a cylindrical track.

FIG. 3*b* depicts a specialty lighting fixture in which the heat pipes 64 are mounted on a heatsink/heat spreader that is preferably mounted or is suspended on a wall or ceiling such that heatsink/heat spreader 13 essentially becomes a "track" in a track lighting fixture. The heatsink/heat spreader 13 may also carry electrical current, as can heat pipe 64.

Figure 3C:
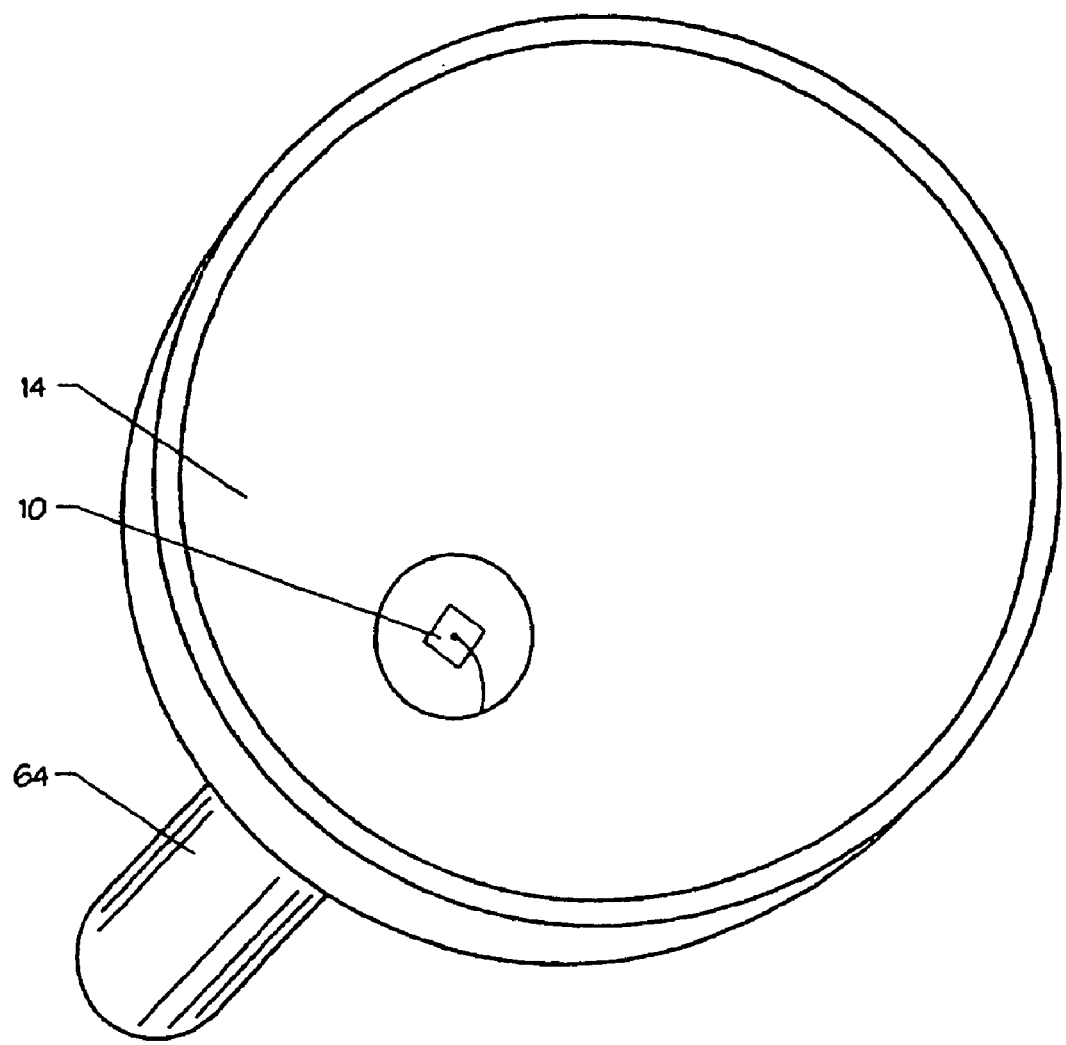
FIG. 3c illustrates a headlight embodiment in which the LED is placed on the tip of a heat pipe and emits into a conical shaped reflector.

FIG. 3*c* shows the headlight (or other light application) in which LED 10 is bonded to the tip of heat pipe 64. LED 10 is surrounded by a reflector 14 that may be TIR, metal reflector, dielectric reflector, faceted reflector, or some combination. The optional wire is shown bonded to the center of LED 10.

Figure 4A:
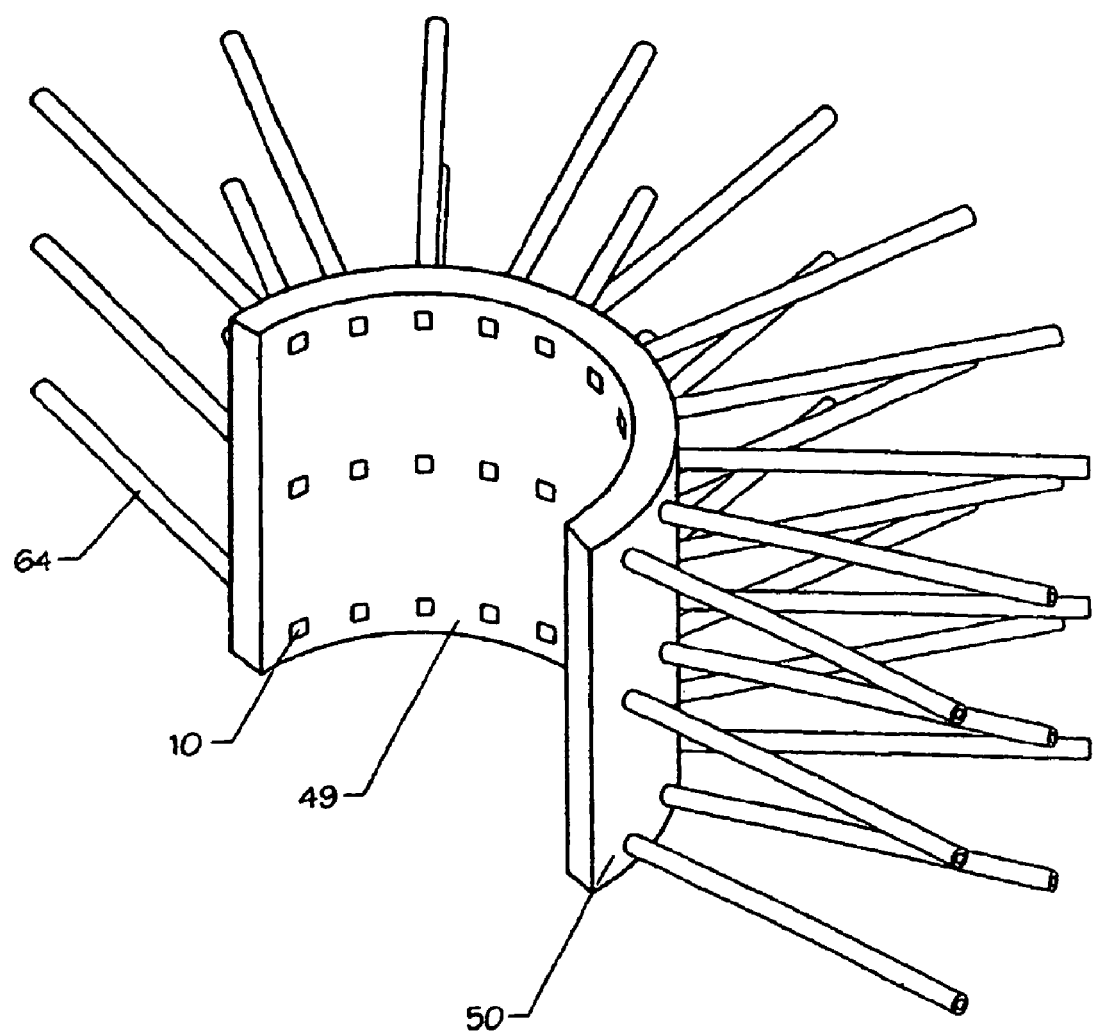
FIG. 4a shows a cosmetic facial illuminating device in which the heat pipes are mounted in the back surface and LEDs are mounted on the front emitting towards the face.

FIG. 4*a* is an LED array according to the present invention. Of particular importance is the concave shape of the surface 99 onto which the array has been mounted. Such a curved array more closely matches the curvature of a person's face than a flat board, and would therefore be a preferred embodiment for the treatment of facial acne or wrinkles. FIG. 4*a* shows the heat pipes 64 protruding from the rear of the curved plate 50. The heat pipes 64 may be substantially parallel to one another, but such an arrangement is not necessarily required; for example, the heat pipes 64 could be oriented so that their "cold" ends are farther apart than their "hot" ends as shown in FIG. 4*a*. The figure depicts light emitted from the array 10 impinging upon a subject person's face.

Figure 4B:
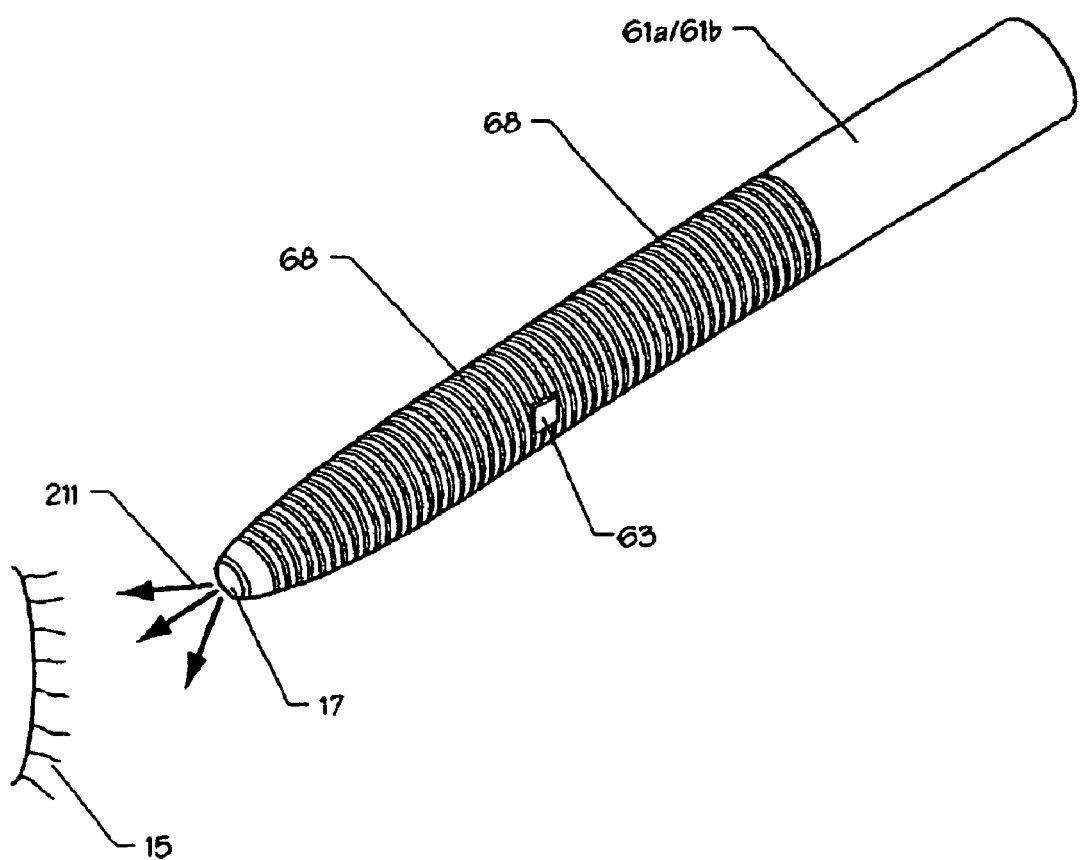
FIG. 4b shows hair removal LED device with hair drawn with light arrows shining towards it.

FIG. 4*b* depicts another light-emitting device incorporating the present invention. This particular embodiment may be used for hair removal applications, and as such, hair 15 is shown in this drawing with light 211 from the present invention impinging on it. This light would most preferably be in the wavelength range from 500 nm to 1600 nm. A visible portion of the spectrum is advantageous so the user may see where the light is impinging. For "home-based" hair removal, careful consideration must be given to user safety and FDA (and other government body) regulations. As such, the utilization of a long-pulse, red wavelength LED 10 (Such as 650 nm) may be well advised. The device may be convectively cooled through the many fins 68 shown in the drawing. It should be noted that the device could also optionally include a gravity- or tilt-type shut-off switch that would prevent the device from being operated in an inefficient configuration for heat dissipation (i.e., with the heat pipe 64 oriented horizontally or so that the LED 10 is above the horizon). A substantially similar device could also be used to treat acne or other epidermal maladies. In such an application, the device may have a lens 17 to further diverge or shape the emitted light (as is true with all the embodiments described herein). It should be noted that the preferred wavelength for acne treatment is in the blue and/or yellow ranges, and that such light could also be used to target and stimulate photoactivated compounds or drugs. This device could also be used as a flashlight. The light might also be used for acupuncture; preferred wavelengths for acupuncture are in the red and/or infrared. Additionally, home-based or medical professional-based treatment for wrinkles with preferably red LED 10 (or laser) light may be employed; such an application would typically utilize an LED 10 with emitting a light wavelength near 590 nm. Very low energy LED light, such as that around 10 mW/cm$^2$ may be effective for wrinkle removal and in the instant invention, a hand held device with the aforementioned LED packaging may be employed. Work in an area somewhat similar to this has been researched and patented by Light Biosciences, Inc. (Virginia Beach, USA).

Figure 4C:
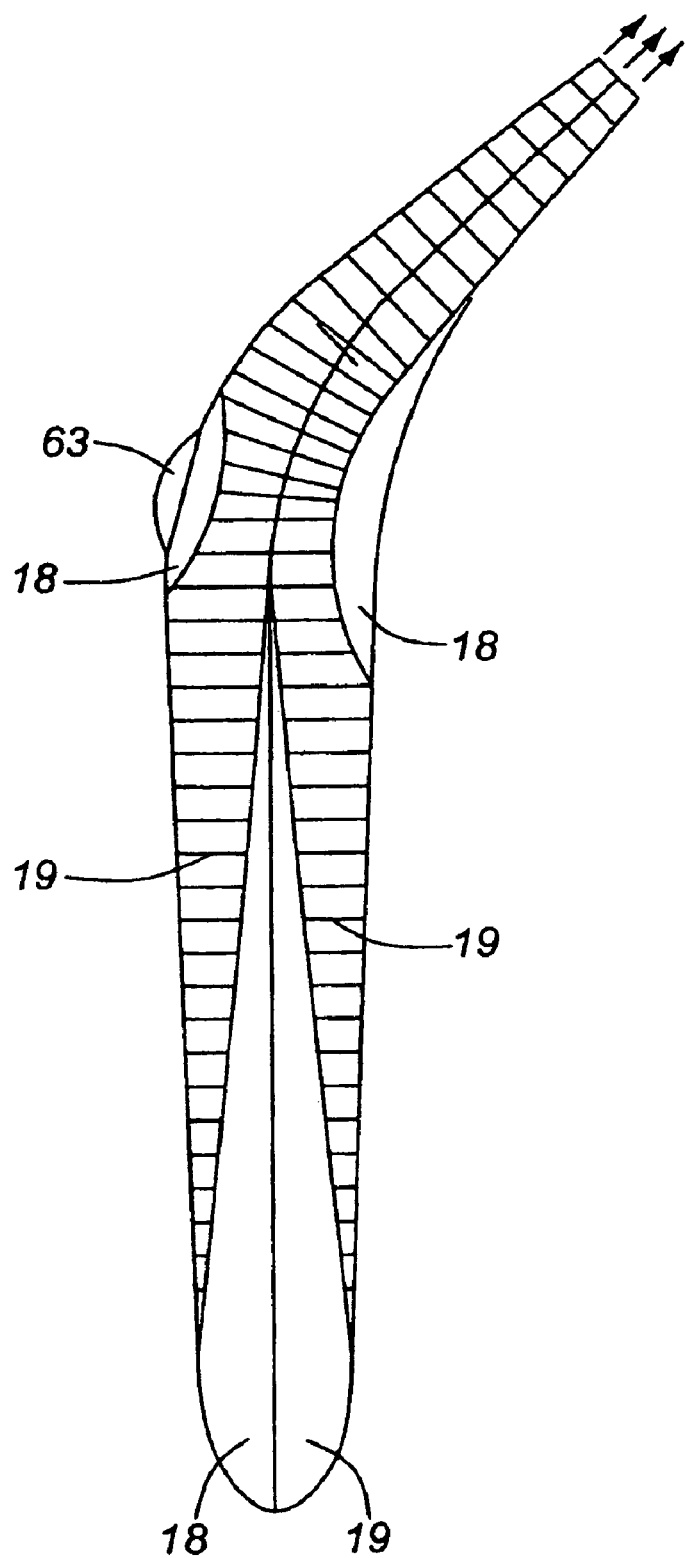
FIG. 4c illustrates a hand held LED device wherein the heat pipe is within the finned heatsink body shown in the drawing and both the heat sink body and heat pipe undergo a gradual bend.

FIG. 4c shows a light emitting device similar to FIG. 4b. The light emission is shown by the arrows. A heat pipe runs the length of the device in the center of the clam shell handpiece. The polymer handpiece (unlined areas) is insert molded with stamped metal finned heat spreaders 19. Switch 63 is shown. Power is supplied by a liquid polymer lithium ion battery that flows around the internal heat pipe and is confined by the polymer wall ID 18 and the insert molded heat spreaders 19. The heat spreaders 19 clamp around the heat pipe and a heatsink compound fills the gap between the heat pipe and the heat spreaders 19. Any embodiment in the instant invention may have stamped heat spreaders (or heatsinks) that "clam-shell" around the heat pipe. Note how the heat pipe is gently bent. This, however; makes it difficult if not impossible to remove the heat pipe for repair of the LED at the tip. The device shown in 4c may be used to cure adhesive, treat acne, or remove wrinkles or hair. It s preferably hand held. This embodiment, as well as all others may be used to "photo-deodorize". The most preferable wavelength is less than 405 in and arrays are preferred.

Figure 5:
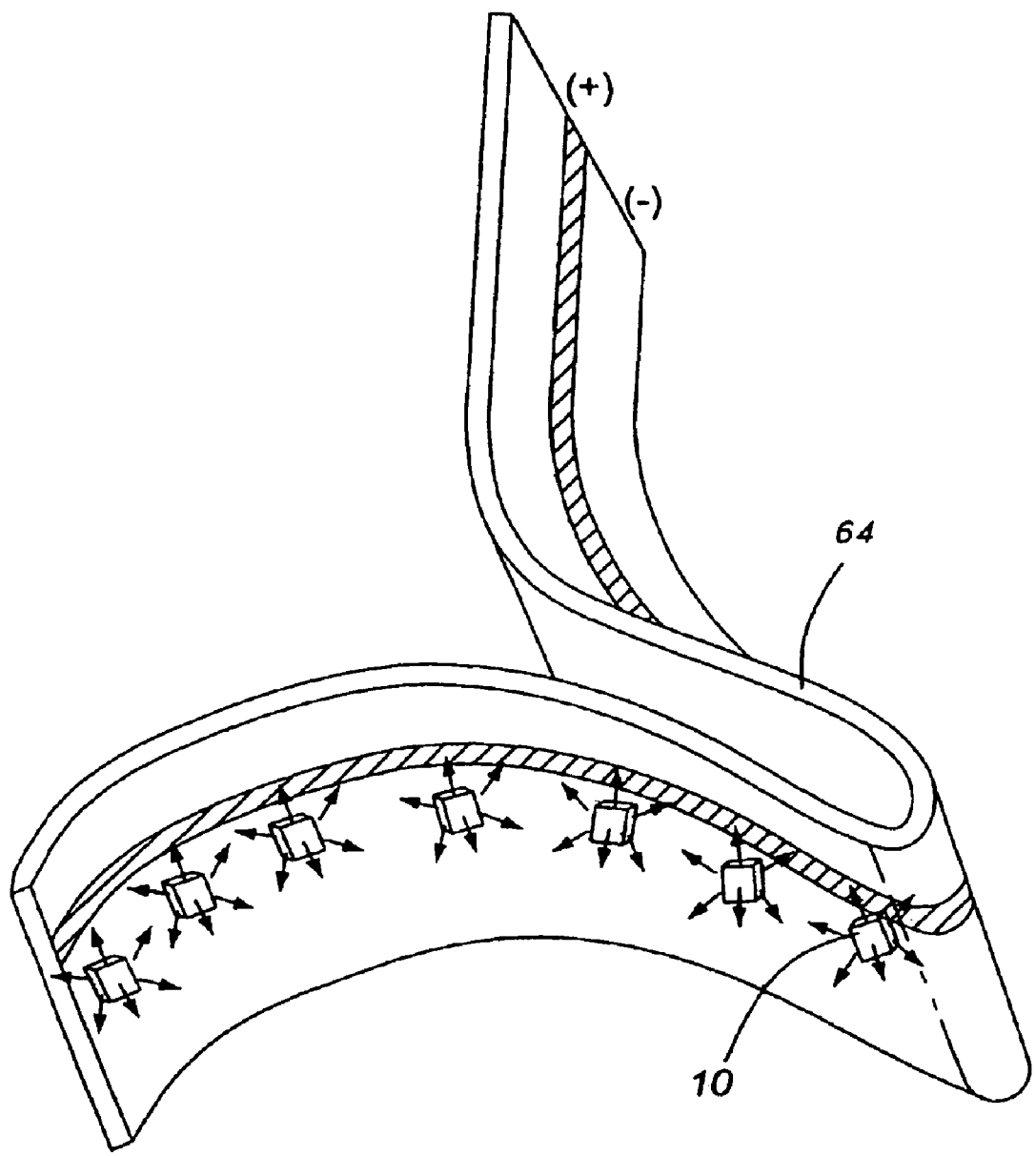
FIG. 5 shows a flattened, flexible heat pipe with seven LEDs arranged in an arch-shape for a teeth whitening application in which the device is inserted in the human mouth.

FIG. 5 shows the LED teeth whitening/gingivival stimulating/breath freshening device wherein thin and flat heat pipe(s) 64 (available from Furukawa Electric, Japan) are employed to transport the waste heat developed by the LED (or LD or OLED) 10. Some of the visible light spectrum shining on gingivival tissue can speed the healing of inflamed or infected gum tissue and may slow down or reverse gingivitis. Short wave length blue light (i.e., approximately 405 nm) is particularly effective. Light emission is depicted by arrows. One or more heat pipes may be bent around a human mouth arch shape. These heat pipe(s) and the LEDs 10 that are encapsulated in a transparent and flexible polymer (not shown, but similar to FIG. 30a). One or more heat pipes may be bonded to heat pipe(s) 10 with conductive glue and may be used to change the direction of heat flow by approximately 90°. This makes the device more ergonomic and these bonded heat pipes may become part of a thermally conductive handle that not only rejects heat to the environment, but also contains batteries. This handle is not shown in a drawing but described herein. Gingivival stimulation may also be accomplished in the yellow, red, or IR spectrum. Short wavelengths, ~405 nm or shorter may kill harmful or odor causing bacteria.

FIG. 5 shows one heat pipe 10 bent around the arch in one continuous piece. LEDs 10 are shown. Also one or more heat pipes (not shown) may be shown bonded to the opposite ends of heat pipe 1035 which then change the orientation of the heat pipe and the resulting direction of the heat flow. The device 10 shown when preferably encapsulated in a transparent polymer may be inserted in the mouth between the teeth/gums and the cheeks. The heat pipe may carry electrical current.

Referring to FIG. 6a, there is shown an LED curing device 60. The device 60 is preferably a hand held LED curing device. In another aspect of the present invention, there is provided a method for mounting and cooling LEDs and devices for same that may be used for curing adhesives or composites and other light source uses. The device 60 includes a tubular wand body 62 made of plastic or metal having two ends a wide end 62a and a tip end 62b which is bent. Please note that the tip end 62b of the body 62 need not necessarily be bent. LED 10 is located at end 62b of the body 62. A heat pipe 64 extending through body 62 is bonded with glue or solder inside the conductor slug 14 preferably of copper of the LED 10, although no cavity or hole need be made in the conductor slug 14. As shown in FIG. 6a, the heat pipe 64 may be modified to "neck" down at the end 62b. Also a flattened heat pipe may be used and the LED is bonded on top of the flattened end. An optional battery pack 61a and 61b may preferably be driven by a wall plug transformer not shown, around middle portion of the body 62. A fan 66 that is approximately 30 mm$^2$ may be located at the end 62a of the body 62. A heat sink 68 preferably of Al or Cu is glued to "cold end" of the heat pipe 64 between the fan 66 and the battery back 61a and 61b. The fan 66 is used to blow air over the heat sink 68 and exhausted through parts (not shown) in the body 62 that most components are mounted in. Switch 63 controls the electrical current to the LED via wires (not shown) connecting the battery pack 61a and 61b to the LED 10. The LED lens 10a is shown surrounded by pambolic reflector 10b and optional additional lens 10c. The heat pipe 64 is a closed container into which a small amount of liquid (working fluid, typically water) is injected under vacuum. The inner walls of the container of the heat pipe 64 are lined with capillary-action material (wicking structure). When a portion of the heat pipe 64 is exposed to heat produced by LED 10, the fluid in the heated portion i.e., hot end of the heat pipe 64 vaporizes picking up latent energy. The vapor flows to the "cold end" of the heat pipe where the vapor 20 cools and condenses releasing latent energy and the condensed fluid is returned by capillary action to the hot end. The heat pipe 64 serves as a heat engine taking heat away from the LEDs 10.

FIG. 6b is an expanded view of the tip end 62b of the device 60 in FIG. 6a. The "pocket" 65 is shown wherein the heat pipe 64 is milled, drilled, molded, etc., in the slug 14 of the LED 10 such that it is only a few 0.001's of an inch greater diameter than the heat pipe 64. High thermal conductivity epoxy is placed in the bottom of the pocket 65 prior to the insertion of the heat pipe 64. The operation of a heat pipe 64 is as discussed above, known by those skilled in the art of heat transfer but has not been used prior to this invention in a hand held LED device 60 for curing or teeth whitening or even flashlights. Also in the prior art, the heat pipe 64 has not been inserted into or onto the slug 14 or submount of an LED 10 as shown, and also not used for the purpose of mounting an LED 10 at the end of a wand 62 having a small diameter of around 8.5 mm Ø. Most LED slugs are glued or soldered to a large PCB board or large, flat heat sink which is incompatible with the application of the LED device 60 described herein. It is understood that the heat pipe 64 could be soldered or glued to the LED "slugs" without the "pocket" 65 or a separate heat pipe could be bonded to the LED.

In the above discussed embodiment of FIGS. 6a and 6b of the present invention, the heat pipe 64 transports heat in a direction that is not substantially perpendicular to the "p-n" junction of LED 10. The end of the device of FIGS. 6a and 6b that includes the LED 10 and reflector 106 mounted on the tip of the heat pipe 64 and surrounded by a sleeve, is bent at 45° about 7 mm from the end of the device. The light is traveling away from the "p-n" junction plane in a substantially perpendicular direction, (if it were collimated) but the majority of the length of the heat pipe, and therefore the direction the heat is transported, is not perpendicular due to the 45° bend in the heat pipe 64. If there were no 45° bend (i.e. straight) the heat would flow in a substantially perpendicular direction to the "p-n" junction.

FIG. 7 shows a liquid-cooled version of the LED hand held curing device 60. By utilizing liquid cooling, the wand 62 (long, slim tube) may be made flexible by using flex liquid carrying tubes. All the devices in this patent application can be used with blue (465 nm) light to active photo initiators or other chromophors or sensitizers in curing adhesives, composites, or other substances, as well as used in devices that may or may not contain light sensitizers, chormophors, or photoinitiators. Other wavelengths from 200 nm to 11,000 nm could preferably be used including "white" LEDs. The LED body 10 is shown with an attached lens 10a. The LED 10 is located at the end of wand 62 that is approximately 8.5 mm Ø and can be flexible, semi-rigid or rigid. Coolant tubes 34 (inlet) and 35 (outlet) are bonded to an optional threaded through hole 67 in the slug of the LED 10. In this way coolant is passed through the LEDs 10 at approximately 2 psi to 50 psi for the purpose of cooling the LED die (not shown, but bonded to one end of the conductor slug 14). The coolant tubes 34 and 35 are attached respectively to the pump 50 which supplies the coolant (i.e., liquid) and a finned heat exchanger 52, which receives the heat. Fan 66 is the drive, electronics for pump 50. Fan 66 passes air over the external fins of heat exchanger 52 and the air is discharged through ports (not shown) in the molded plastic housing of the body 62. No electrical leads are shown for drawing clarity. Battery pack 61a and 61b is shown. The device may be operated strictly from batteries or may have a cord to a wall mounted transformer. The purpose of the liquid cooling is to be able to remove the heat generated by the LED die 10 that is in a very small area and "pump" the waste heat to a larger area, the heat exchanger 52 via the heat pipe 64. Using this technique, LEDs may be driven at higher operating currents and output power than if they were mounted to a-flat heat sink and/or PC board (PCB). Additionally, it is difficult to have a heat sink of PCB out at the end of an approximately 8.5 mm Ø wand that is needed to get into "tight" spaces in an electronic assembly glue curing application or a patient's mouth for curing or whitening. Also very important, is the fact that it is easy to make a "wand" that is flexible if liquid cooling is used to transport heat at high flux from one end of the wand to the other.

FIG. 7a is an expanded view of FIG. 7 wherein the inlet and outlet tubes 34 and 35 respectively, are more clearly shown. These tubes are available from HV Technologies (North Carolina) with a thin spiral or coil wire in the wall for kink resistance. 90° bent tubes 71 and 73 are glued into the through hole 67 in the conductor slug 14 to pass the coolant from the inlet tube 34 into the LED 10 and similarly to send the coolant out of the LED 10 into outlet tube 35. The approximately 8.5 mm Ø tube wand 62 may be rigid or flexible depending on the application. Curing industrial/photonic adhesives could be accomplished by using a flexible "mono-coil" type outer tube that would carry the coolant tubes 34 and 35 and electric wires to the LED 10 at the end. The "mono-coil" would then serve as a sort of replacement for a light-guide for curing equipment. The LED 10 at the end could also be replaced by an edge emitting laser diode or VCSEL. Flashlights, light wands, etc. may use the instant invention because it allows for driving the LED 10 at higher currents than would be possible with just a heat sink, and is especially useful in small, contained areas where it is difficult to cool high power density devices and areas where a flexible light source is advantageous.

FIG. 7b is an expanded view of another embodiment for the instant invention. Here the LED 10 has a coolant inlet hole 75 in the center of the conductor/slug 14 and a feeding inlet tube 34 is shown. The inlet hole 75 is bisected by one or more outlet holes 75a and 75b near the bottom or end of the hole 75. This arrangement allows for lower thermal resistance cooling as the inlet hole 75 serves to "impinge" coolant on the area of the conductor/slug 14 at the bottom of hole 75 that is immediately below the LED "die" (not shown for clarity). The outlet holes 75a and 75b (two more outlet holes are not shown for clarity) allow the heated coolant to escape with minimal back pressure where it is returned via pump 50 to the heat exchanger 62 (or chiller). It is understood that all these embodiments do not necessarily have to be hand held. A "5 W" LED may preferably be driven with two to six times the current with this technology. Multiple arrays or single LED 10 (or laser diode) units may use the same cooling techniques described in the instant invention for static or stationary wall or bench-top units for many applications where a light source of high intensity in a tight space is required beyond just curing and teeth whitening.

In an alternate embodiment of the present invention, there is provided an LED device wherein the LED die is mounted and/or bonded to the tip of a heat pipe, where the heat pipe may have the function of an anode or cathode in addition to its heat sinking and transport functions. This LED/heat pipe invention has broad applicability when used with UV or visible LED packages and/or individual die or combinations of each. Some of the applications include displays, specialty lighting, outdoor lighting, architectural lighting, UV lamps for curing adhesives, spectro-fluorometers, photo-catalyst activation, high resolution optics, space communication, short range optical communication, counterfeit detection, chemical detection, medical applications, teeth whitening, teeth bleaching, germ killing, erasing EPROMS, lithography, decomposing toxic substances, air purification, and countless other applications.

Referring to FIG. 8, there is shown the heat pipe 64 having an average range of the diameter of preferably between 3 mm and 6 mm and average length preferably ranging between 25 mm and 500 mm. The LED chip (of die) 10 is shown bonded to the tip of the heat pipe 64. The heat pipe 64 may be flattened to accommodate the flat die. It is understood that packaged LEDs, i.e., presoldered to heat sinks or slugs could also be used. If the conductor slug 14 is used it may have a female contour in it to accommodate the end of the heat pipe 64. The heat pipe 64 itself may be the electrically charged anode 11 and a wire bond may be made on top of the LED die as shown in FIG. 8 to make the cathode wire connection 12. These functionalities could also be reversed. In this manner, the heat pipe 64 provides an electrical connection to the LED 10 in addition to cooling the same. The heat sink 68 may be bonded to the condensing end of the heat pipe 64 and an optional fan 66 to blow air serving as the cooling medium over the heat sink 68.

In FIG. 8a the heat pipe/heatsink is shown with multiple LED dies 10. They may be connected in electrical series or parallel or be individually addressable. The dies 10 may emit one or more centered wavelengths A shaped, molded or potted polymer or glass or ceramic lens 81 is shown and it may encapsulate the LED dies 10 and is preferably made from a UV degradation resistant polymer. The arrows 82 depict the light emission from the LED(s) 10. Element 84 depicts a vapor cavity that extends down the center of the interior of the heat pipe 64. It is substantially parallel to the outside diameter sides of the heat pipe 64. The LED cathode and anode surfaces ("p-n" junction) are substantially perpendicular to the heat pipe vapor cavity 84 axis of the heat pipe 64 which is substantially straight and unbent. The heat pipe 64 may be bent in many different shapes for many lighting applications.

Figures 9, 9A:
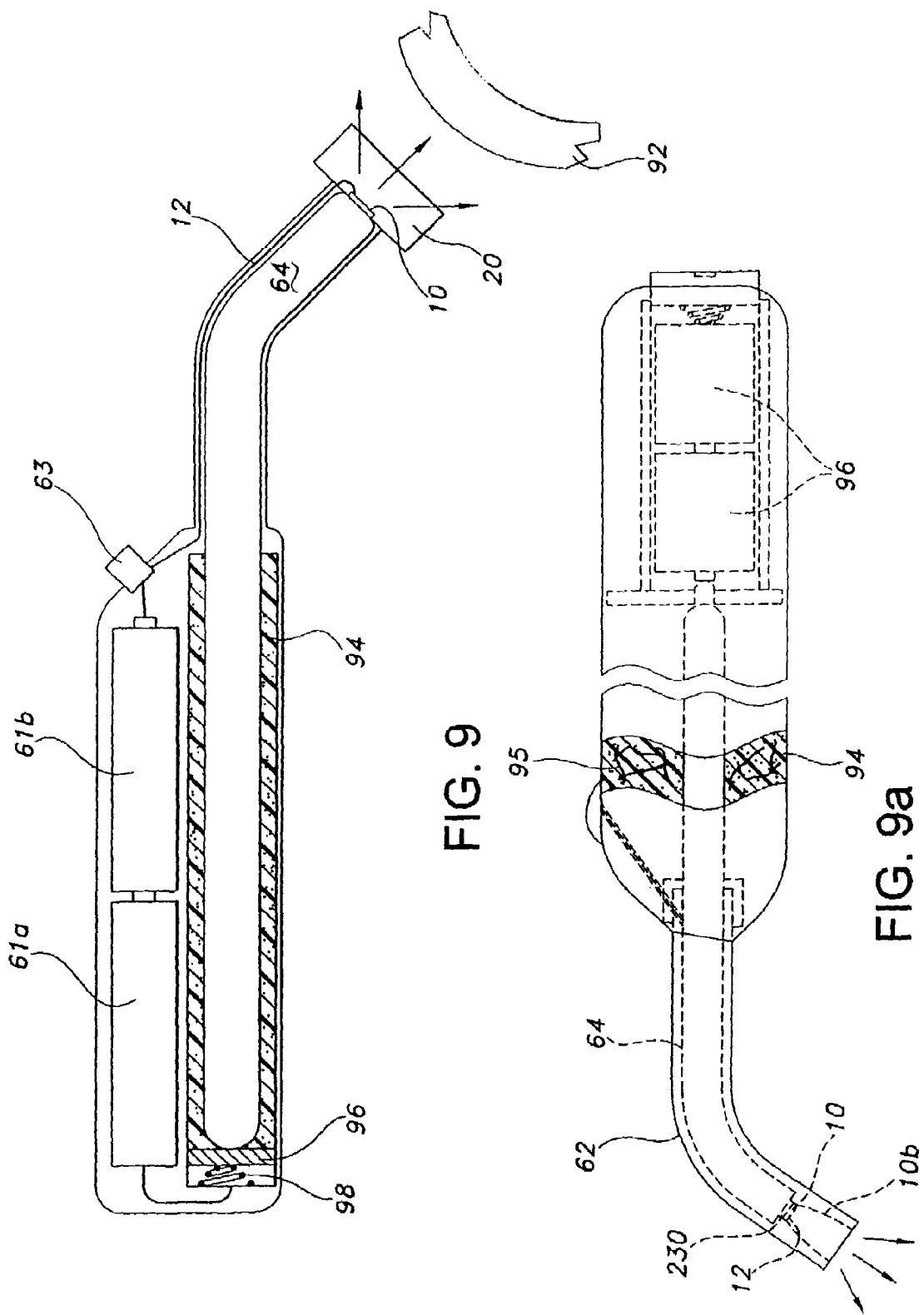
FIG. 9 is a perspective view of an alternate light-emitting device that is cooled by a phase change material.
FIG. 9a shows an adhesive curing device in accordance with an embodiment of the present invention.

FIG. 9 is a hand held LED curing device 60 having a plastic housing that incorporates at least one LED die 10 or at least one pre-packaged LED device that is bonded to the evaporating end of a heat pipe 64. Cathode wire, 12 is bonded to the cathode side of the LED die (not shown). Element 20 is a transparent material that is preferably a UV resistant potted or molded polymer as discussed and shown earlier in FIG. 2. Again, element 63 is the electrical on/off switch. Element 92 is a surface including a gel material that preferably contains hydrogen peroxide, and also preferably a photosensitizer, photoinitiator, or chromophor that the actinic light from the LEDs "activate". Element 94 is a phase change material that is preferably a paraffin material which is placed between heat pipe 64 and the rest of the part of the device outside the heat pipe 64. When the LEDs 10 are turned on, the waste heat will flow down the heat pipe 64 and melt the paraffin 94 after a predetermined approximate time. The paraffin 94 will melt, i.e., change from solid to a liquid and expand and "break" the electrical circuit that is formed between the batteries 61a and 61b (which may have a different orientation than shown, i.e., upside down) the electrically conductive piston and spring 98, the electrically conductive (preferably water filled copper) heat pipe 64 (which, in essence becomes the anode), the LED die 10 (or pre-packaged LED device) and the cathode wire 12. This phase change will help conduct heat away from the condensing end of the heat pipe 64. In this case, instead of fan, paraffin 94 will absorb heat from the heat pipe 64. Furthermore, paraffin 94 absorbs heat energy without raising temperature when it melts and cools down. Again, this process works best for short duty cycle application. The novelty of this embodiment is the ability to rapidly transport heat from the LED 10 through a heat pipe 64 past the batteries 61a and 61b and to a forced convection cooling (or also non-forced convection in another embodiment). For short duty cycle applications the heat pipe 64 (preferably porous) can be surrounded by a phase change material, such as paraffin, to absorb heat as will be described in greater detail with reference to FIG. 9 below.

FIG. 9a shows an adhesive curing device embodiment of the present invention. As in other embodiments, a CVD Diamond heat spreader 230 as shown in FIG. 19, is optionally positioned between the LED 10 and the heat pipe 64 in the wand tube 62, which is anodized. If the anodized wand tube 62 is not used, the heat pipe 64 can preferably be covered with ~0.002" thick polyester shrink wrap. Here, the heat pipe 64 functions as the anode 11 to the LED 10. LED 10 is optimally soldered to the CVD heat spreader 230 which in turn is conductively glued to the end of the heat pipe 64. Cathode wire 12 is bonded to the LED 10 and the parabolic reflector 10b. As in other embodiments, a phase change material 94 (usually paraffin) can preferably be in communication with the heat pipe in order to further dissipate the heat being generated by the LED 10 and transported along the length of the heat pipe 64. Here, the phase change material 74 is also in communication with copper wool 95, which further dissipates heat throughout the phase change material 74 due to the high thermal conductivity of the copper wool. This embodiment is shown to include lithium batteries 96 but, as in other embodiments power could instead be supplied to the device of the present invention using a power cord of some kind.

Figure 9B:
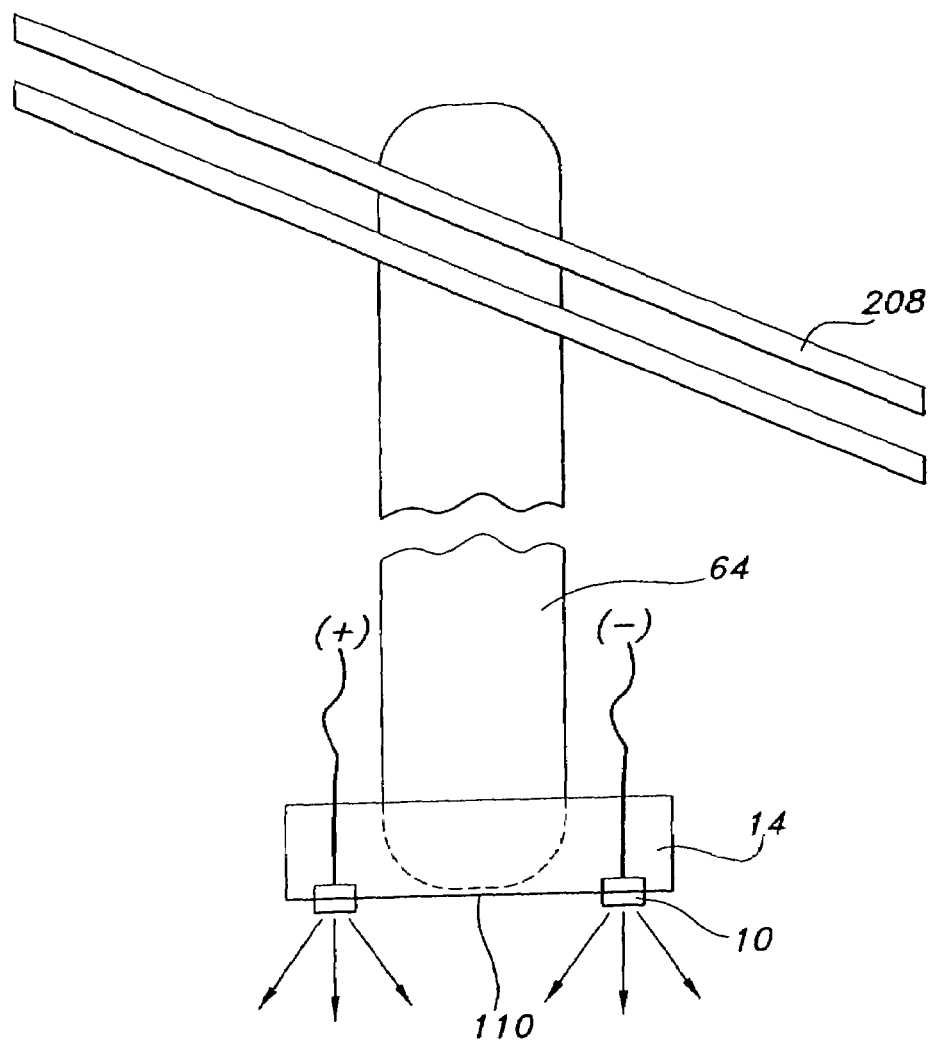
FIGS. 9b and 9c illustrate a device including multiple LED way with detachable fins according to an alternate embodiment of the present invention.
Figure 9C:
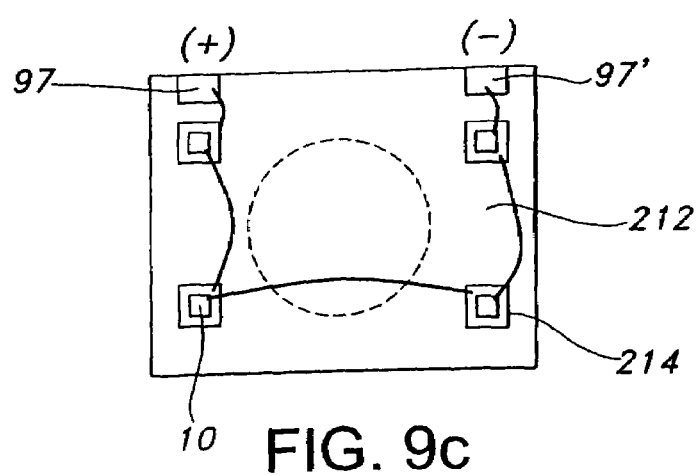

FIGS. 9b and 9c depict an LED array for use in general lighting or in ultraviolet curing applications. This embodiment is composed of a number of LEDs 10 disposed upon a slug 14 with a blind hole into which the heat pipe 64 is fixably and/or detachably inserted. Fins 208 as more clearly shown in FIG. 12a are optionally included. Fins 208 are preferably bonded with solder 110 or a high thermal conductivity glue. The fins 208 further dissipate the heat transferred from the LED 10 to the heat pipe 64. The LEDs 10 are attached to the slug 14 via bond pads 214 via bond wires 212 as more clearly shown in FIG. 14b, and may be electrically powered in series, in parallel, or as individually addressable entities. The number of LEDs 10 that may be used in this type of an embodiment is limited only by the size of the slug 14 and the heat transport capacity of the heat pipe 64 in combination with any other heat dissipation mechanism (such as the fins 208). It is easy to envision an embodiment wherein the single heat pipe 64 is replaced by a number of separate heat pipes of similar or varying size, all of which are in communication with any number of LEDs 10 via a single slug 14. It is noted that two fins 208 are shown but more than two fins 208 are possible. Positive 97 and negative 97' gold contacts wrap around the edge of the slug 14. Also note that LEDs 10 are shown in series, but may also be in parallel.

In another embodiment, the device of the present invention is preferably used in architectural lighting fixtures or in UV curing applications where the heat pipes are located in different orientations wherein the hot end has the LEDs and the cold end is in a heat sink. The heat pipe in these embodiments is somewhat analogous to the function of a light pipe or lightguide except that it transports heat instead of light, and the source of light is at the output tip of the heat pipe. Also disclosed is the automobile headlight embodiment with heat pipe, reflector, LED, and heat sink. Small headlights or even tail light, dashboard, or other areas can be illuminated and the heat transported to an area that is bigger, for the heat sink. This is a remote lighting application using the heat pipe instead of a lightguide or light pipe.

In an additional aspect of the present invention, there is provided a device used to cure UV inks and coatings and adhesives. The device includes an array of large area UV (or visible) LEDs that are mounted on heat sink(s) which are cooled by an array of (circular or flat) heat pipes that are themselves cooled by one or more fans as described in detail below.

Figure 10:
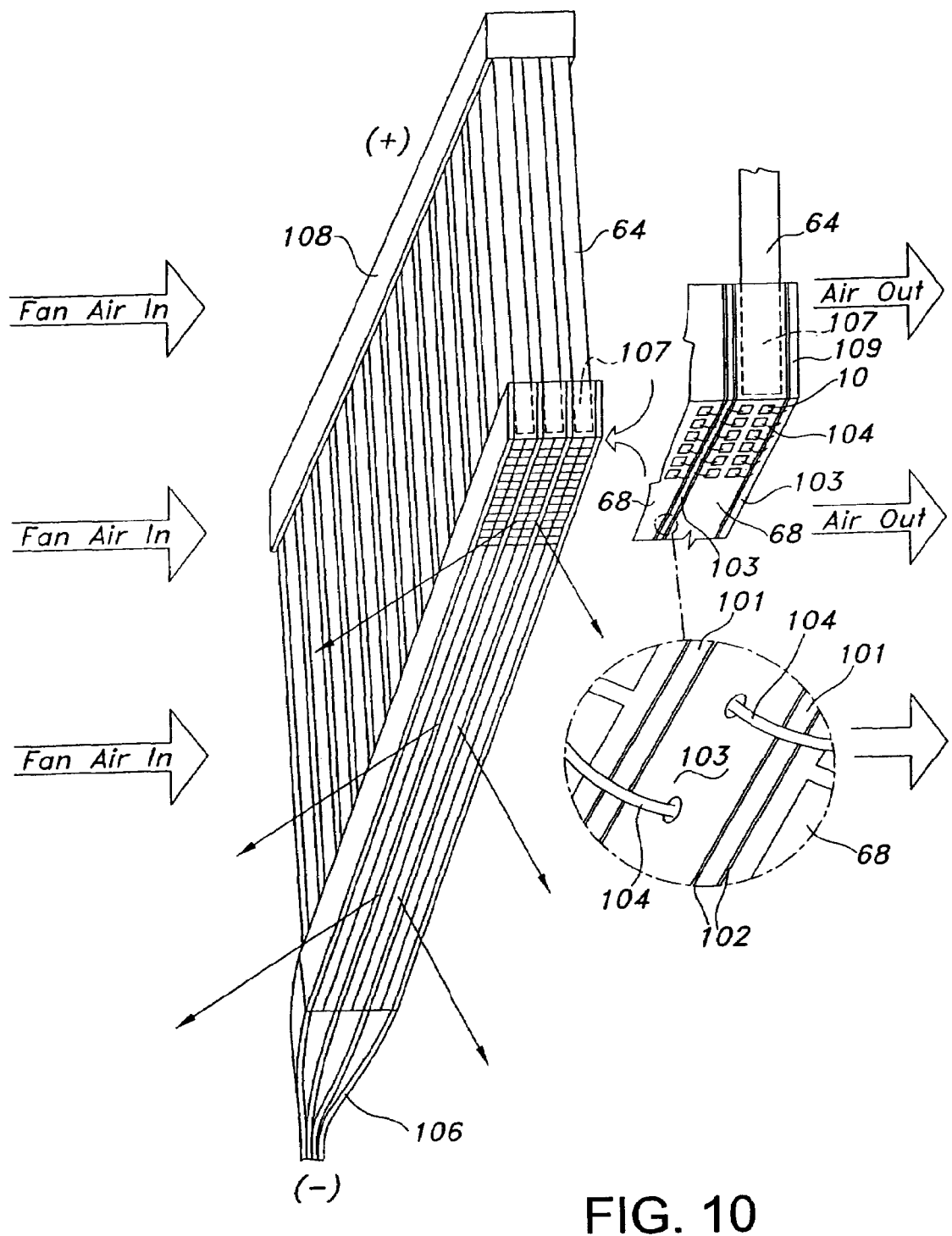
FIG. 10 shows a device having an array of large area UV or visible LEDs mounted on multiple sinks and cooled by an array of heat pipes according to an alternate embodiment of the present invention.

Referring to FIG. 10 there is shown a device 100 having an array of LEDs 10 which are soldered to one or more heat sinks 68, preferably formed of copper. The heat sinks 69 are electrically isolated from each other by thin strips of Kapton 101 or other non-conductive material that have thin layers of adhesive on both sides 102 and a layer of copper foil 103 sandwiched in between. Each LED 10 has a wire bond 104 that attaches to the copper foil 103 of the heat sink 68. All copper foil layers 103 are brought to form the cathode common electrical connection. For every approximately 11 mm of electrode length them are three approximately 3 mm Ø blind holes 107 drilled in each electrode 109 (only one of 90 are numbered). An approximately 200 mm long by 3 mm Ø heat pipe 64 is inserted with an electrically conductive compound in each hole 107. The heat pipe condensing (cold) ends are inserted in a top plate 108 and attached with an electrically conducting compound such as conductive epoxy. This top plate 108 serves as the common electrical anode connection. Depending on the design of the LEDs the polarity of the electrical connections can be reversed or modified. The current path as shown, is through the top plate 108, down the heat pipes 64, through the electrodes 109, through the LEDs 10, through the wires 104, and out through the copper foil 103. It is understood that electrodes 109 could be monolithic with circuit "traces" for a cathode connections, or they could be electrically isolated from the heat pipes 64 and the LEDs 10 could be bonded directly to the heat pipe tips (ends), which is most applicable if there is a through hole (rather than blind bole) in electrodes 109.

Glass may be ion beam sputtered over the LEDs 10 for index matching purposes. Gold may be electroplated onto the copper surfaces for ease of wire bonding and die bonding. A single point, diamond-turned, fly-out pass may be made over the bonded three electrodes, 109 to create a small, flat, die-bonding surface. Lastly, a glass plate (cover slide) may be placed over emitting LEDs 10 to protect them. The glass may be hermetically seated and have a sub-wavelength structure on it for anti-reflection purposes. Also, flat plates (thinner than the top plate) can be installed to increase surface area. Preferably one or more 100 mm fans on each side of the heat pipe array cool the heat pipes in a push me-pull me arrangement. The optional flat plates can be oriented parallel to the airstream (from fan(s) or blower(s)). It is to be noted that in FIG. 10, the LED 10 repeat down length of device in groups of six and only 18 LEDs of approximately 540 LEDs are shown for drawing clarity. However, different quantity and sizes of LEDs 10 may preferably be used.

The heat pipes are preferably oriented vertically so that the wicking action is enhanced by gravity. The heat pipe (or heat pipes) may have an additional bonded heat exchanger (or heat sink) with fins surrounding it (for added surface area) or it may be stand-alone (no bonded heat sinks or fins). When an array of heat pipes are employed each heat pipe essentially becomes a "pin" in a so called "pin-fin" array heat sink to dissipate thermal energy from the LEDs over a large area. The heat is taken in by the heat pipe 64 at the end where LED is placed and spread out in the entire surface area of the heat pipe which preferably is between 2-8 mm in diameter. In the preferred embodiment, the heat pipe transports the heat away from the "p-n" junction of a diode in a direction that is substantially perpendicular to the junction. It must be stressed that because heat pipes can be bent in most any shape or form, it must be understood that the heat pipe could transport heat in a direction that is not substantially perpendicular to the junction. The vapor cavity in the heat pipe may have only a portion that is nearly perpendicular or nearly parallel to the "p-n" junction. Also, only a portion may be nearly perpendicular or nearly parallel to the emitted light from a light emitting device. The aforementioned word "nearly" may be substituted with "substantially" Also, the term "heat" can be used interchangeably with "waste heat", "thermal energy", etc. One or more heat pipes (arrays) cooling one or more, light emitting devices (arrays) may be of small (preferably less than 2" square inches) or large (preferably more than 2" square inches) dimensions thus used for a variety of medical and industrial uses such as curing adhesives or hair/wrinkle removal or teeth whitening. For curing adhesives, an apparatus similar to FIG. 10 is ideal for all applications that a microwave (electrodeless) lamp is currently used for. These microwave lamps are currently available from Fusion, Inc. (Garthersburg, Md., USA).

The inner diameter ("ID") along the length of the heat pipes is comprised of a hollow vapor cavity 84 as shown earlier in FIG. 8. The light from the LEDs is generated at the "p-n" junction which is epitaxially grown in layers on a preferably GaN wafer which is diced into chips. The chips may be bonded to the electrodes "p" side down. Other wafer types are SiC and sapphire. Other means for forming "p-n" junctions other than epitaxial may be employed. Different styles and sizes and manufacturers of LEDs may be substituted for those described and depicted in the figures. As discussed earlier, the cold ends of the heat pipes 64 can be cooled by a coolant (liquid or gas). The electrodes 109 could also be liquid cooled and have internal channels therein.

In an additional aspect of the present invention, there is provided a novel LED packaging scheme and process for making same which results in a very simple, inexpensive and compact package. This advantageously allows the rapid transport of thermal energy away from a high energy density heat source such as an LED chip, to a very large surface area heat sink while minimizing the size of the heat source and the frontal, cross-sectional area of the heat sink surrounding it. This fast thermal transport most preferably allows the operation of LED chip(s) at a threefold to fivefold (or more) increase in power over standard packaged chips while keeping the operating (junction) temperatures well within rated limits. Also, since brightness can be defined as the "power per solid cone angle of light," when increasing the chip power while maintaining the same cone angle, brightness is increased. This invention combines high brightness LED chips and highly effective heat pipes in a novel packaging scheme and process for making same which results, not only in the ability to operate the LEDs at unprecedented brightness, but also unprecedented cost per watt. Essentially, one chip is outputting the power of three to five chips (or more), not in the area of three to five chips, but in the area and cone angle of a single chip, with minimal heat sink area consumed around the periphery of the chip. This small frontal cross-section results in the ability to use compact and efficient lenses and reflectors that can take advantage of the chip's brightness in the most efficient, effective and space saving way possible. The devices depicted in this application may contain at least one infrared ("IR") die and the emitted light may be used for curing adhesives or coatings by heat instead of the more common UV or visible photoinitiated chemical reaction. The LEDs may be used individually or in array form with one or more heat pipes either in a unit that is hand held, fixed, or some combination of both. The present invention most preferably combines mainstream IC packaging technology, circuit board technology, and power LED technology in a novel configuration that provides solutions to a broad array of solid state lighting products. These include devices for hand held light curing, photodynamic therapy (PDT), specialty lighting and outdoor or indoor displays.

Some other applications include photocatalyst activation, spectrofluorometers, space and short range optical communication, counterfeit and chemical detection, medical, germ killing, erasing EPROMS, lithography, decomposition of toxic substances, air purification, and countless other applications. All these applications and devices advantageously utilize the primary attributes of the technology which is high brightness and power in a very compact and cost effective package. The LEDs may be used individually or in array form with one or more heat pipes either in a un it that is hand held, fixed, or some combination of both.

Figure 11:
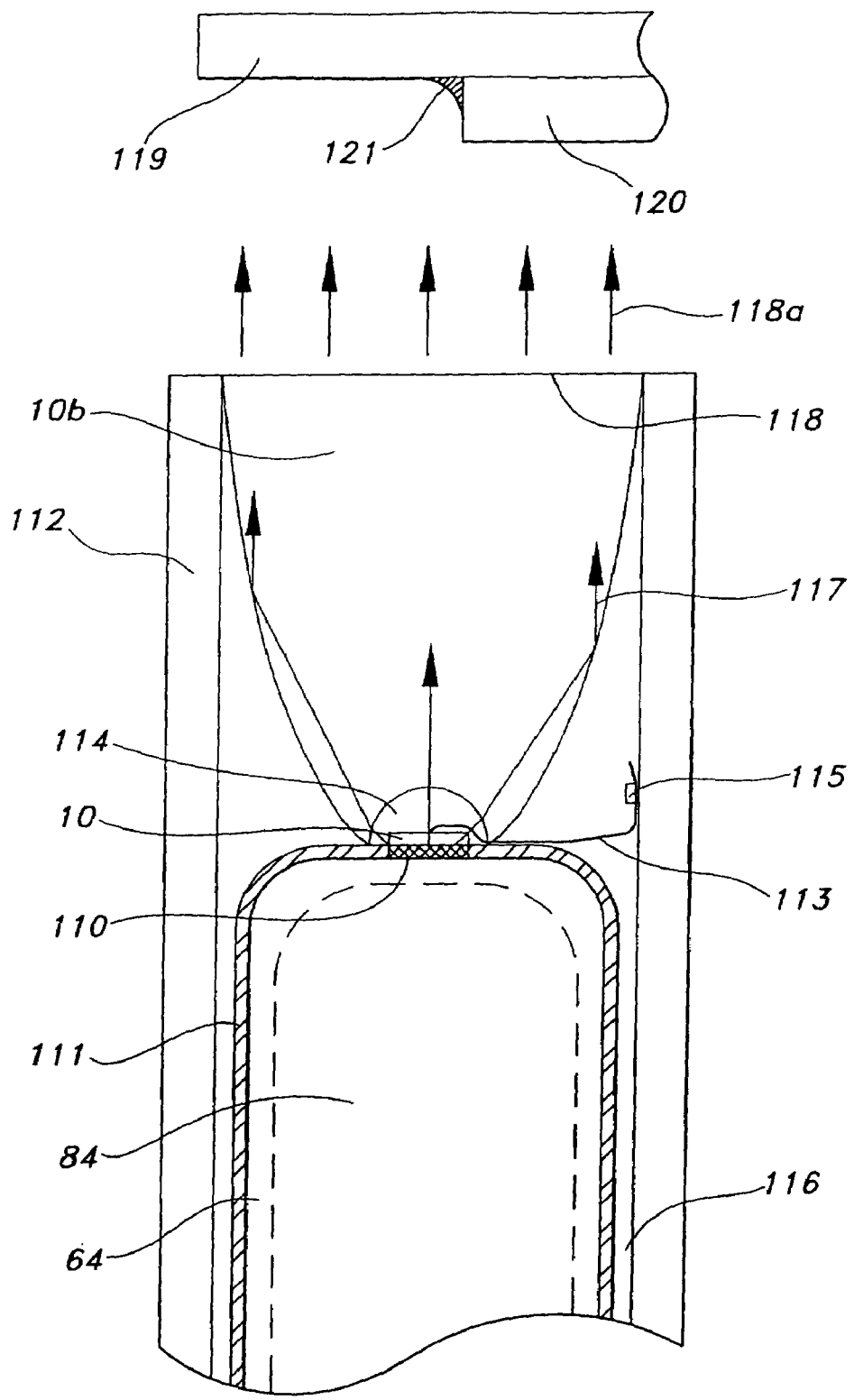
FIGS. 11, 11a, 11b, 11c, 11d, 11e and 11f illustrate various embodiments of a novel packaging of LEDs and heat pipes according to the present invention.

Referring to FIG. 11, there is shown a LED 10 bonded to the tip of at least one heat pipe 64. The LED(s) 10 is (are) affixed to the heat pipe 64, by a solder or an adhesive 110 such as indium or tin, lead/tin, or gold/tin that is preferably electrolytically deposited to the heat pipe 64. The solder process may use flux or be "fluxless". The square (or other geometrical shape) is defined by an exposed and developed area of the electrophoretic photoresist 111. The flux process must be compatible with the photoresist. This photoresist layer 111 also acts as a dielectric (insulating) layer. The heat pipe 64 is adhesively bonded to the inner diameter of tube 112 comprised of conductive material, preferably aluminum. The tube 114 may be anodized and it can act as the cathode to the device when the wire 113 is bonded or mechanically affixed to it in an electrically continuous manner. The diamond-turned or injection molded elliptical or parabolic total internal reflection ("TIR") reflector 10b is placed over the LED 10. It has an index of ~1.53. The TIR reflector may be a Dielectric Totally Internally Reflecting Concentrator (DTIRC), a Compound Parabolic Concentrator (CFC), an Elliptical Concentrator (EC), a Compound Elliptical Concentrator (CEC), or a Compound Hyperbolic Concentrator (CHQ). All of these may have flat or curved exit apertures. If curved, an aspheric surface may be employed. If flat, a diffractive surface may be employed. These reflectors may be comprised of a low melting point moldable glass. These reflectors also have the unique ability to mix multiple wavelengths that may be emitted from multiple light emitting devices into a homogeneously mixed beam of light. We refer to this unique attribute, as a "color mixing TIR" reflector. The space for the LED 10 is an integrally molded, concave female preferably hemispherical surface 114 that is filled preferably with a high index silicone polymer or other transparent material. This high index polymer may preferably be ~1.6 or greater. The refractive index between reflector 10*b* and the surface 114 can preferably add optical power and bend light rays to stay within the critical angle for TIR. An anti-reflection (AR) coating may be ion beam sputtered (or other process) on the plane (or curved) emitting surface of the TIR reflector 10*b*. The vapor cavity 84 of the heat pipe 64 is shown and is only approximated. In the preferred embodiment of the invention, the heat pipe 64 of a conductive material, preferably copper, may act as the anode (although it could be cathode or even electrically neutral or some combination of all three). A conduction path can be traced from the batteries (not shown), through the heat pipe 64, through the solder 110, through the LED 10, through the wire 113, into the insulated sleeve tube 112, and back to the batteries (not shown) through the electrically conductive heat sink(s) (not shown) after passing through a switch (not shown). The wire 113 is bonded to the inner diameter of the insulated sleeve 112 with a small dot of electrically conductive adhesive 115. FIG. 11 depicts only one LED die 10 but multiple LEDs 10 at the same or multiple or varied wavelengths may be employed. The dielectric layer 111 electrically insulates the electrically active heat pipe 64 from the electrically active sleeve 112. The sleeve may be desirably anodized aluminum with an unanodized spot underneath glue dot 115 so as to form a current conduction path from the wire 113 to the tube 112. A small gap 116 may or may not exist and it may be filled with a material such as thermally conductive or thermal insulating adhesive. This may be advantageous if the tube 112 and heat pipe 64 are bent near the tip at an angle of approximately 30° to 45°. The wick structure 127 shown in FIG. 11*f* is preferably small, axially extruded grooves but it may be a screened-wick or sintered (powdered) metal wick. Sometimes the heat pipe may be oriented such that the hot side is down (ungravity-aided wick) and in such instances the liquid fill may be decreased at the point of manufacture to reduce the likelihood that "flooding" may decrease heat transfer due to boiling inefficiencies because the LED is at the lowest possible point (i.e., center of tip of heat pipe). An AR coating or sub-wavelength structure may be employed on the exit aperture 118. LED light emission is depicted by arrow(s) 117 which are shown undergoing TIR at the reflector wall/air interface. Light emitting from aperture 118*b* is depicted by arrow(s) 118*a*. The light 118*a* is then impinging on the example application of two blocks 119 and 120 with light cure adhesive. The light is of sufficient intensity to "cure" the adhesive 121 and the two blocks 119 and 120 will be affixed together by the cohesive strength of the adhesive 121. The adhesive curing device in FIG. 11*a* may be used to cure "surface coatings" such as UV clear coats, conformal coatings, etc. The device may also be used to cure "solid-body" objects such as those found in stereolithography processes or casted or molded objects. Examples of these "solid-body" objects are the bases and/or ear molds for hearing aids as well as countless applications involving photochemical curing of molded objects in transparent or open molds.

The LED 10 bonded onto or near the tip of at least one heat pipe 64 simultaneously maximizes the rate of heat transfer away from the LED chip 10 and minimizes the frontal cross-sectional area of the heat sink 68 or submount or heat exchanger. The light emitting 82 from the LED junction(s) 10 preferably travels in a direction that may be substantially opposite to that of the waste heat that is transported axially down the length of the vapor cavity 84 of the heat pipe(s) 64 and away from the junction(s). The light from the device may emit into a shaped volume that is substantially opposite to a shaped volume of material which the heat is dissipated in or transported to. The plane that separates these two volumes may be the "p-n" junction plane (the transition boundary between p-type and n-type materials in a semiconductor) and/or it may be the plane that the epitaxial "p-n" junction is bonded to. Because the heat preferably is not distributed over a large radial distance, but rather a large axial distance, close spacing of LED or LED assemblies (or an array of assemblies) as well as their associated optical systems (lenses, reflectors, etc.) and heat exchangers may be spaced closely together. This results in high power LED devices and/or assemblies that are more compact, lightweight, and inexpensive to manufacture than conventional devices.

It has not been shown in the previous art to place a heat source such as a diode (or other high energy density semiconductor device) on the tip of a heat pipe because it has been considered sub-optimal. The reason for this is that it has been thought to be best practice to place the heat pipe into a larger heat sink with the heat source bonded to this heat sink so as to allow the heat sink to spread the heat around and along a larger surface area of the heat pipe. The problem with this is that there is generally more material between the heat source and the heat pipe and the heat must travel through this excess material to reach the heat pipe itself, as well as travel around the circumference of the heat pipe. Also, the heat will spread both toward and away from the cold (heat exchanger) and because the source is not at the tip of the hot end, all this imparts a great deal of thermal resistance between the heat source and the heat exchanger. Also, if a small high power density device (like a diode) is placed near the wall of the heat pipe it can "dry-out" i.e., deplete the wick structure of fluid of a localized area. By placing the die, such as a light-emitting diode 10, on the tip of the heat pipe 64, as shown in FIG. 11, there often is not a functioning wick structure immediately below the die, and so dry-out may be less of an issue. Most importantly, a full 360° heat spreading around the heat pipe 64 is easily accomplished in a radially and circumferentially uniform manner, thereby decreasing the likelihood of dry-out as thermal energy moves along the wick structure. The LED 10 (heat source) is at the hot (evaporating) end of the heat pipe 64 at the furthest possible point from the cool (heat exchanger) end of the heat pipe. The cool end is also known as the "condensing" end. Additionally, if the heat pipe 64 is at an angle so that the heat source at the tip is closer to the ground than the cool (heat exchanger) end, then the heat source has the benefit of being fed coolant (i.e., water) that is aided by the force of gravity as discussed above. This coolant may pool or form a reservoir that is a ready source for the wick structure due to evaporation that consumes liquid from the wick structure. This process decreases the likelihood of the dry-out phenomenon. Lastly, by bonding the heat source directly to the heat pipe 64 without a heat spreader or heat sink there is one less thermally resistive bond line for the thermal energy to travel through before reaching the heat pipe 64.

Figure 11A:
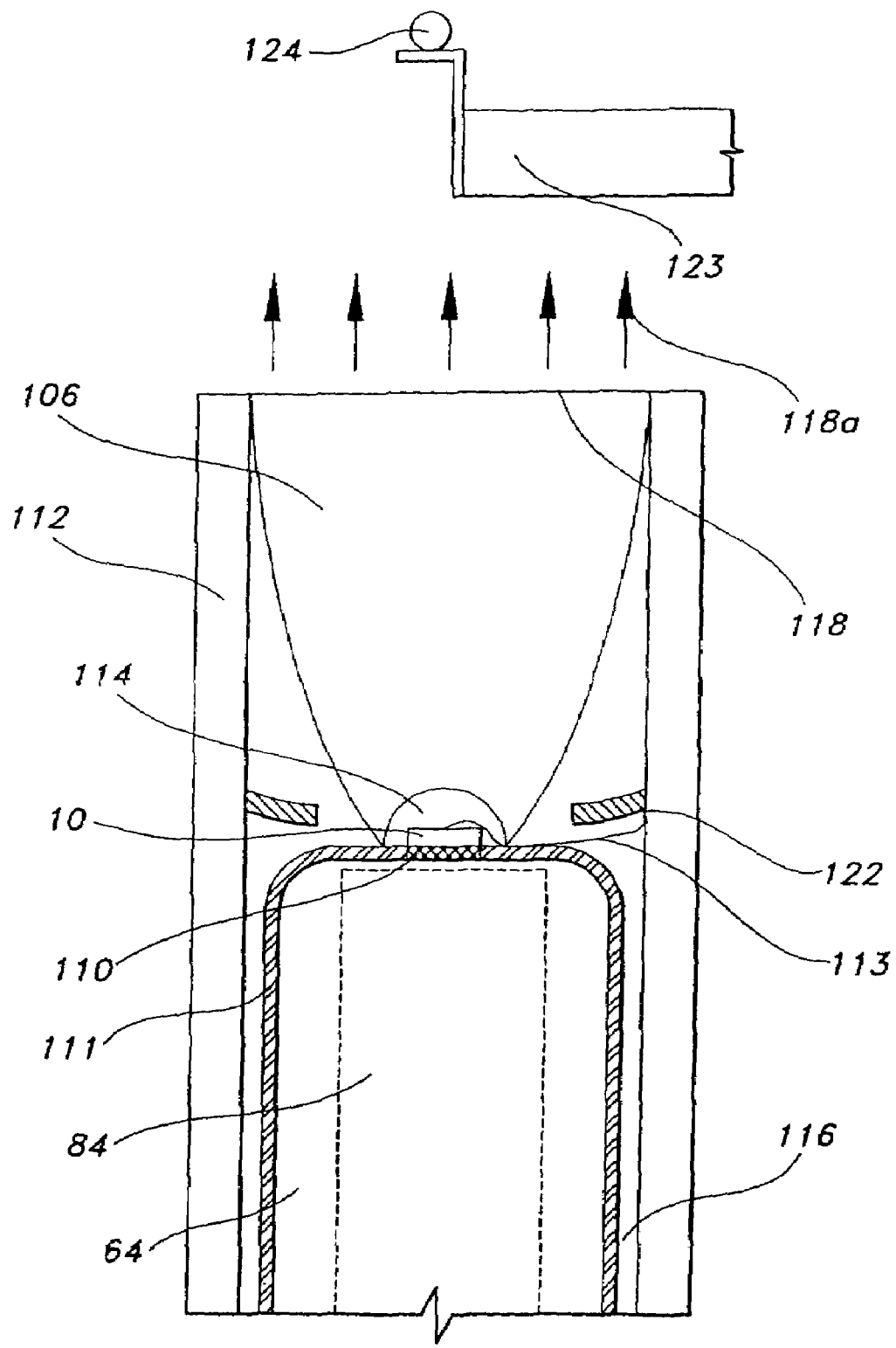

FIG. 11a is similar to the structure shown in FIG. 11, further including electrically conductive washer 122 that wedges the wire 113 against the inner diameter of the sleeve 112. Incidentally, the sleeve 112 may be plastic with a metal conductive strip adjacent to washer 122 or it may be a conductive metal with an electrophoretic coating to protect it from the environment. The electrophoretic coating would have a bare spot where the washer 122 contacts the sleeve 112. Similar to FIG. 11, light emitting from the exit aperture is depicted by arrow(s) 118. In the example application the light 118 is shown impinging on surface mount device 123 and its lead with solder bump 124 as shown in FIG. 11a. The light may have an IR wavelength (could also have UV, visible, or other). In this application, the solder bump 124 will reflow from the heat of the light 118. The solder bump 124 may instead be a light cure adhesive bump or a heat cure adhesive bump, and may or may not have a solder or flux component in it. The LED light (as in all embodiments) may instead be emitting from a laser diode. If the light is emitting from a laser diode, it may preferably be focused to a very small spot. A visible component of light (perhaps from an LED) would be preferred if the actinic light was invisible (i.e. UV or IR). This nearly point source of light may be used for other applications, as well as for heating, surface modification (i.e., ablation, etc.) or photo-chemical reaction, etc.

Figure 11B:
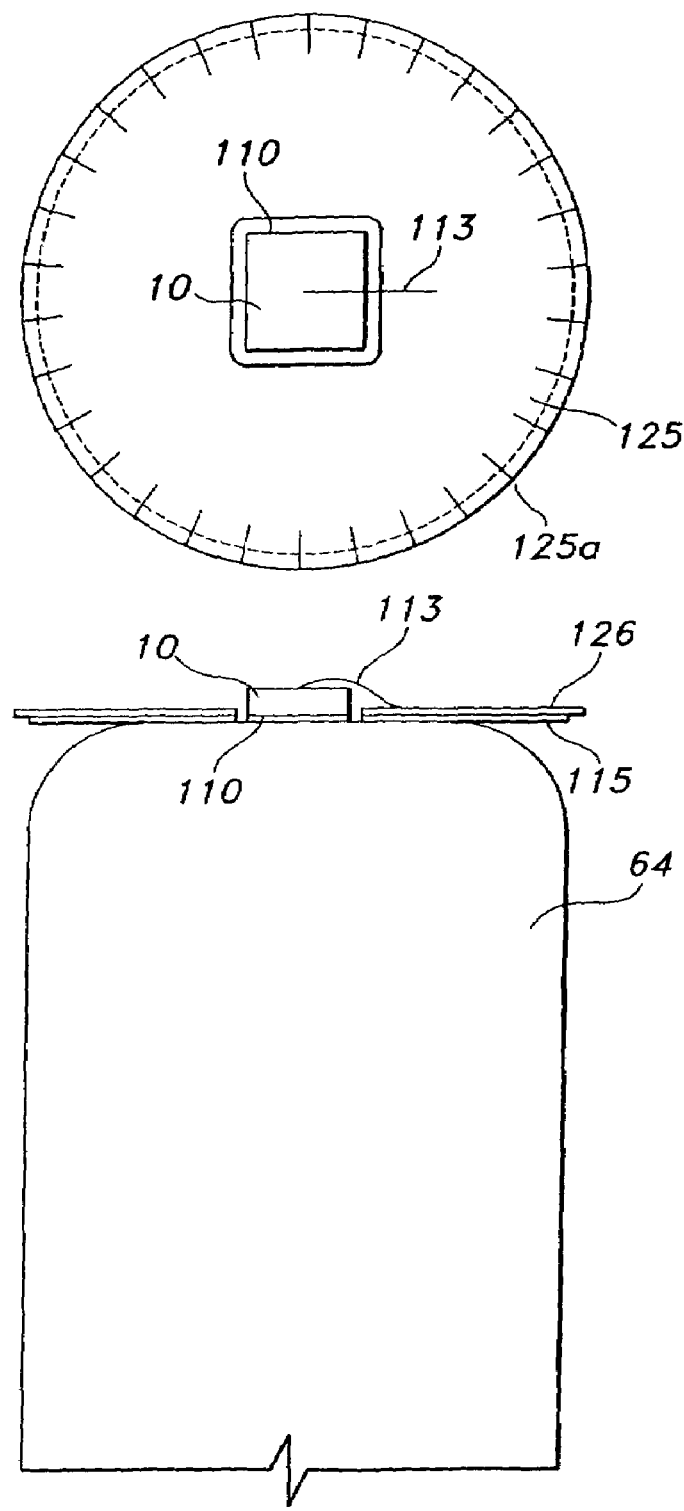
Figure 11C:
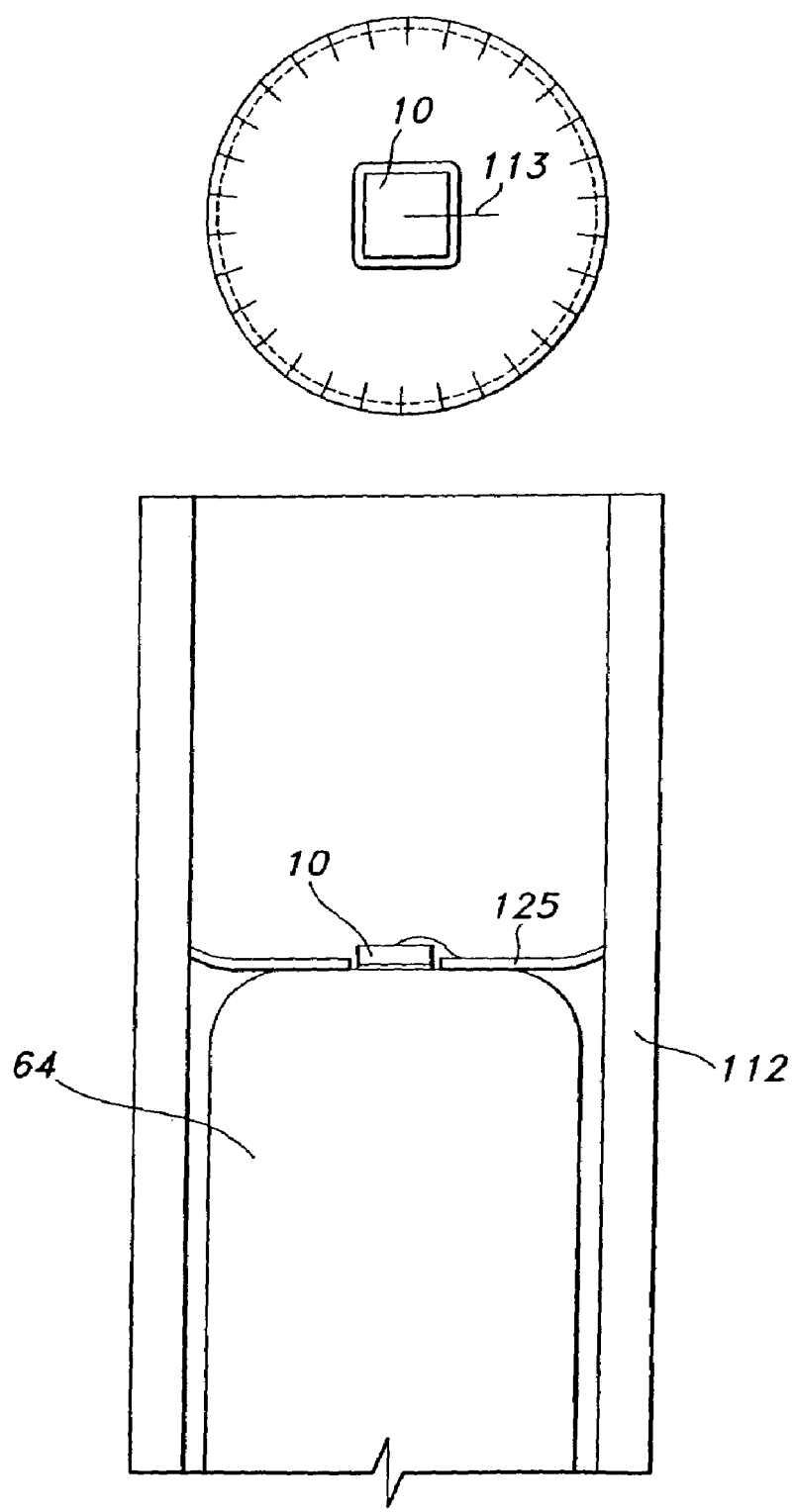

FIG. 11b depicts another embodiment of the invention for mounting the LED(s) 10 in the center of the heat pipe 64. The Kapton or other non-conductive material ring 125 is coated preferably with copper on the top surface 126 of the ring 125. The ring 125 has a shape, preferably a square shape cut out in the center which allows for proper die positioning when an external sleeve just bigger than the heat pipe 64 diameter is positioned around it. A solder reflowing operation may be undertaken and when the solder 110 (that may be already coated on the bottom of the die 10) is reflowed, the ring 125 will keep it centered on the heat pipe 64. The wire 113 that is bonded to the center of the die 10 is also bonded to the top 126 of the ring 125. The conductive copper (or other conductive material) on the ring 125 has perforations 125a that allow it to bend into a myriad of "fingers" when a conductive sleeve 112 in FIG. 11c is brought into contact with it, thereby forming a current conduction path from the heat pipe 64 up through solder 110 and die 10, through the wire 113 into the copper surface of the LED 10 and then into the sleeve 112 of FIG. 11. An adhesive such as glue 115 may exist below or on ring 125.

FIG. 11c is similar to Drawing 11b, except that the conductive sleeve 112 is making contact with the conductive ring 125. The sleeve 112 may be anodized aluminum except a small area may be masked during the, anodizing operation to allow an exposed electrically conductive area that can contact ring 125. Instead of anodizing, an electrophoretic coating may also be employed.

Figure 11D:
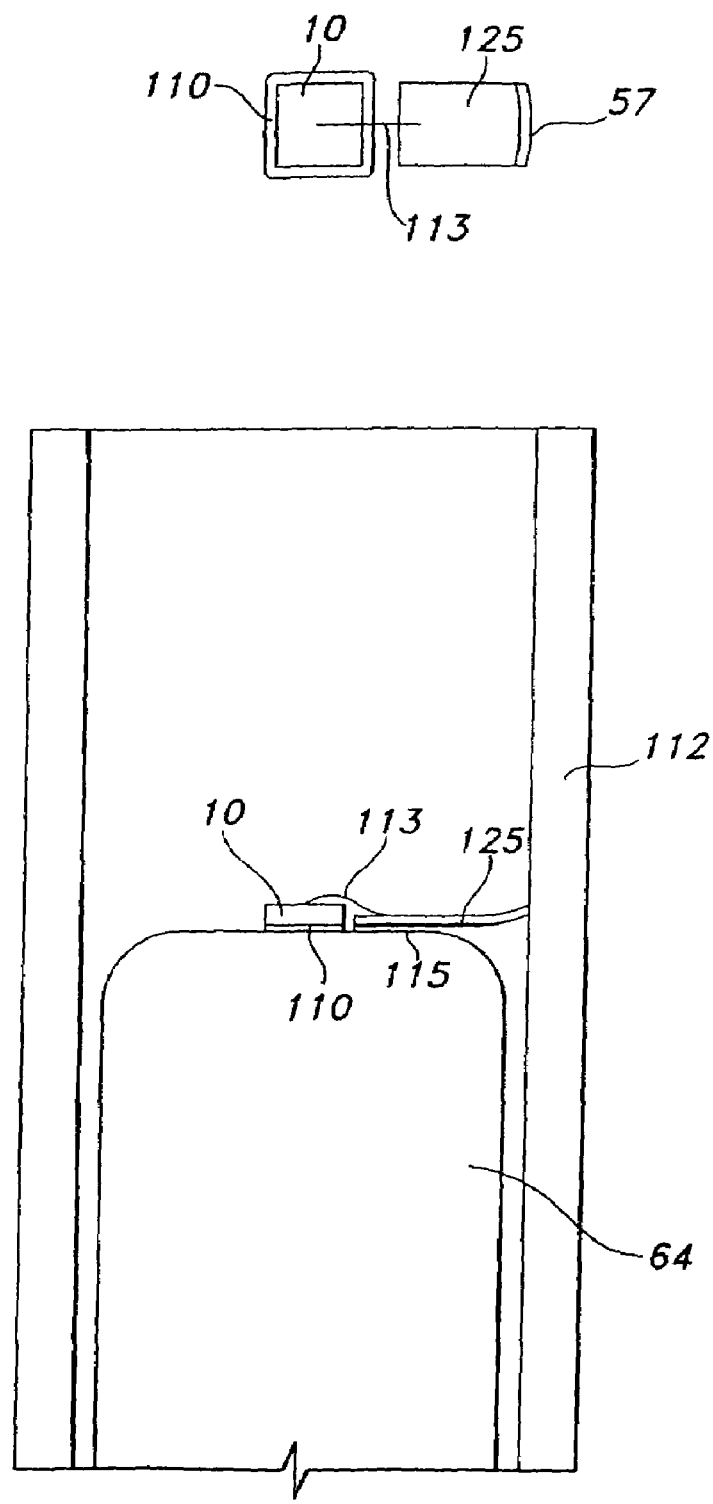

FIG. 11d further depicts the heat pipe 64 with the solder 110 and the LED die 10 on top and in the center of the heat pipe 64. The wire 113 is bonded to the center of the die 10 and also is bonded to die top of the copper strip or Kapton ring 125 that has an adhesive section 115 between it and the heat pipe 64. The current connection between the die(s) 40 and the sleeve 112 is made when the copper strip/Kapton ring 125 contacts the sleeve 112 which is connected in a current conduction path to the battery(s) or power supply (not shown). The die 10 may be centered by a manual or computer driven die bonder or a pick and place machine, with or without machine vision. This is true with all die(s) depicted in this invention.

Figure 11E:
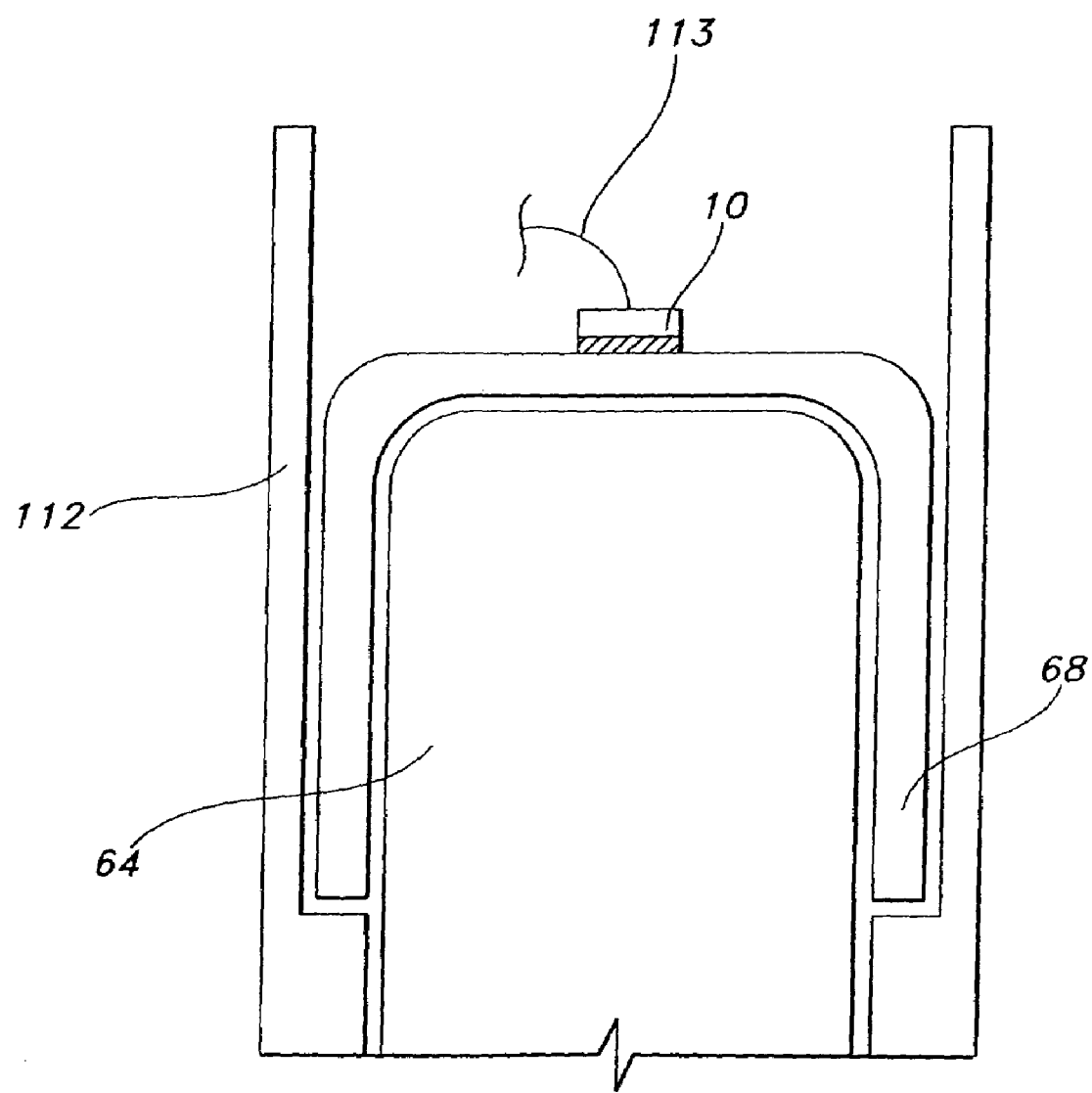
Figure 11F:
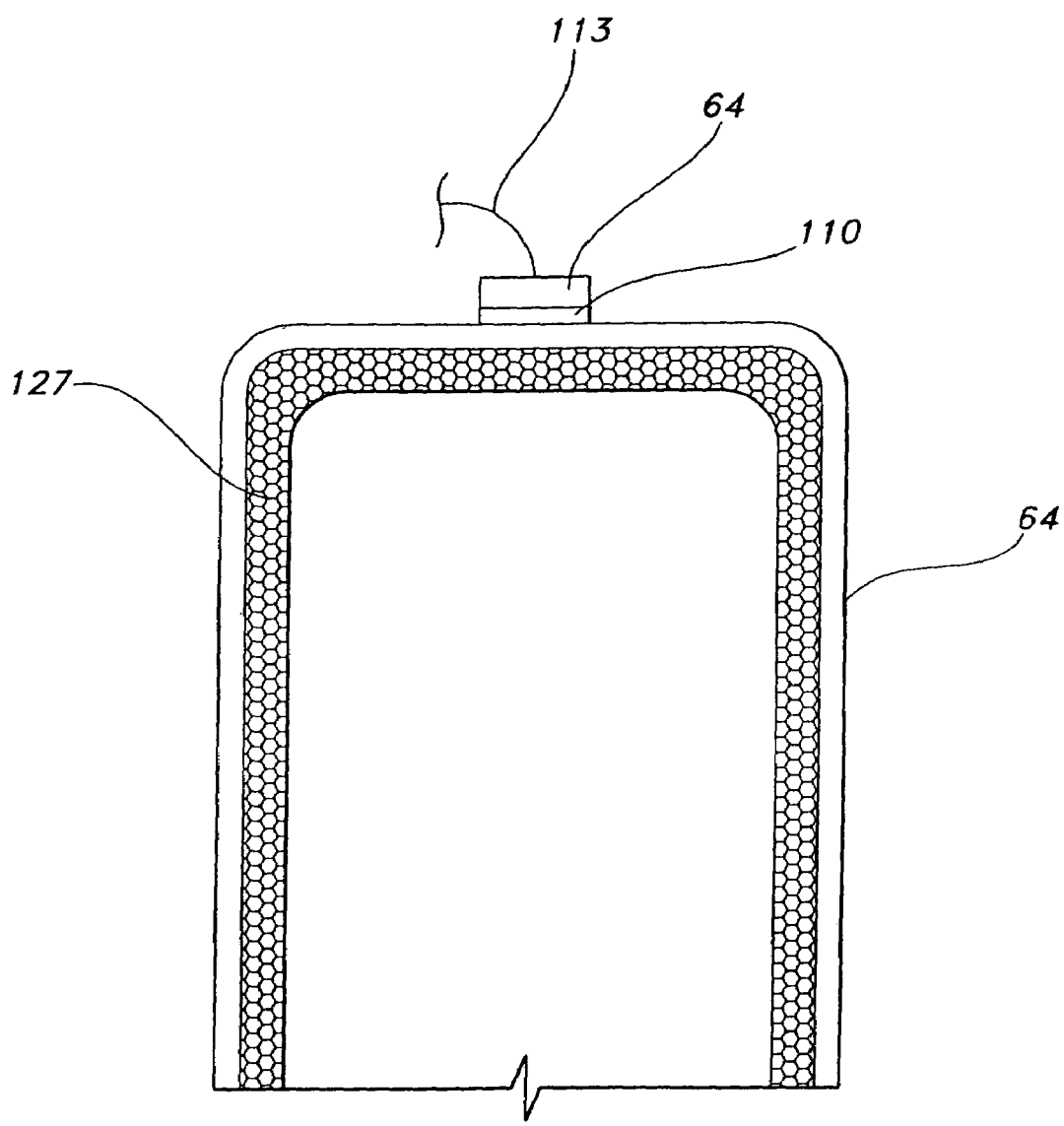

FIG. 11e shows the sleeve 112 as a separate heat sink 68. The LED 10 is shown with attached wire 113 mounted on the tip of the heat pipe 64. The sleeve 112, the heat sink 68 and the heat pipe 64 may preferably be electrically isolated from each other and may be any polarity, of neutral, or a combination of polarities. They may also carry electrical traces that can be individually addressable and traced to individual dies.

FIG. 11f further shows the heat pipe body 64 with sintered wick structure 127. In this application, the wick structure 127 is shown with a full coverage of operation wick structure, not only along the inner diameter circumference walls, but also completely covering the tip body surface under the die 10 at the hot end of the heat pipe 64 shown in this drawing. The solder 110 or conductive epoxy is shown as well as wire 113 which is bonded to die 10. If a thermosetting adhesive exhibiting a high thermal conductivity such as one disclosed in U.S. Pat. No. 6,265,471 is used, it is preferred to first deposit silver (Ag) to both the die 10 and surface of the substrate (or any two contacting surfaces) it is bonded to as this greatly decreases the contact thermal resistance (interfacial resistance) because the patented formulation of the adhesive allows fantastic heat transfer between silver-silver connection and worse performance with contact between other material.

Figure 12:
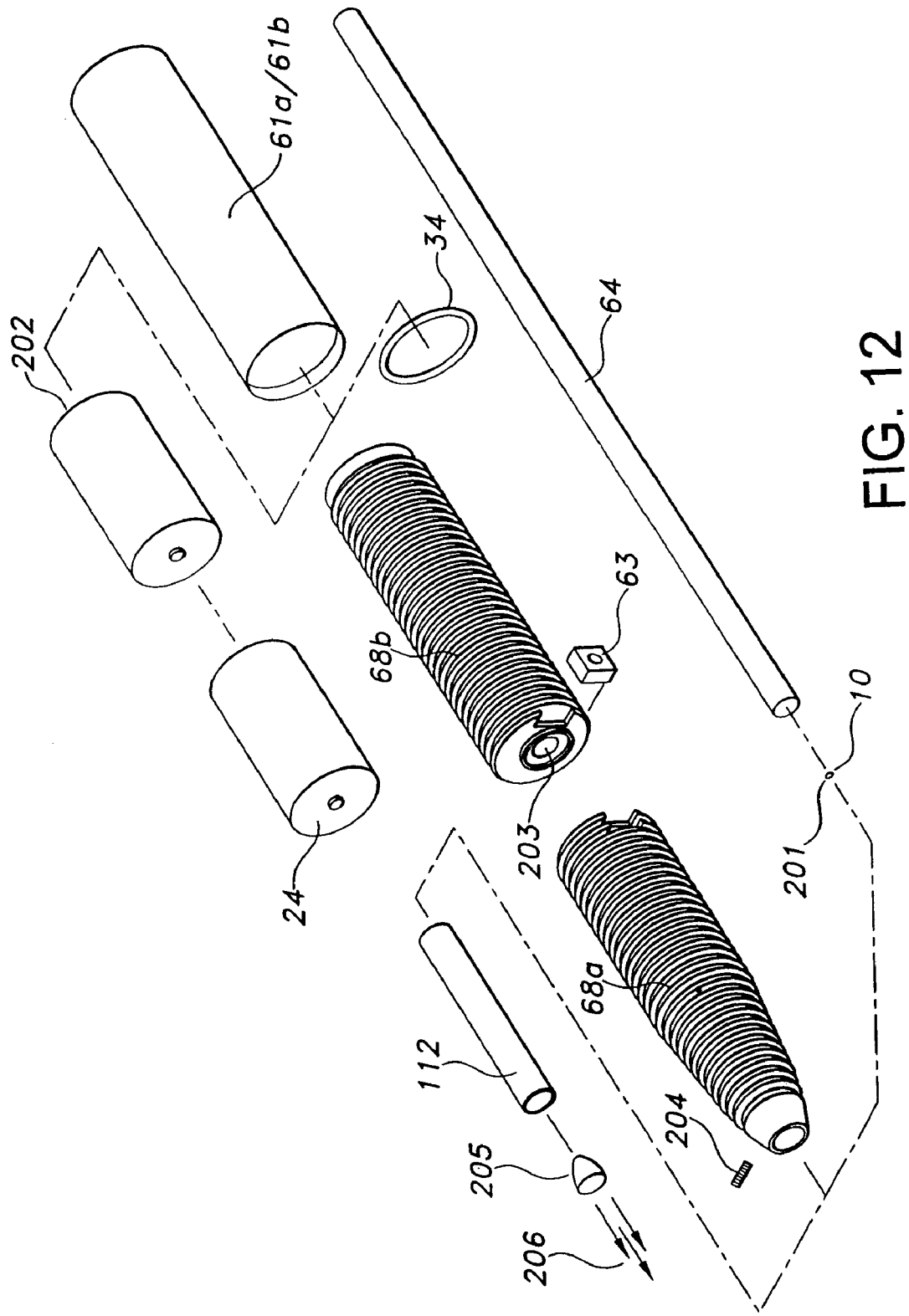
FIGS. 12, 12a, 12b, 12c, 12d and 12e illustrate various embodiments of the LED/heat pipe assembly according to the present invention.
Figure 12A:
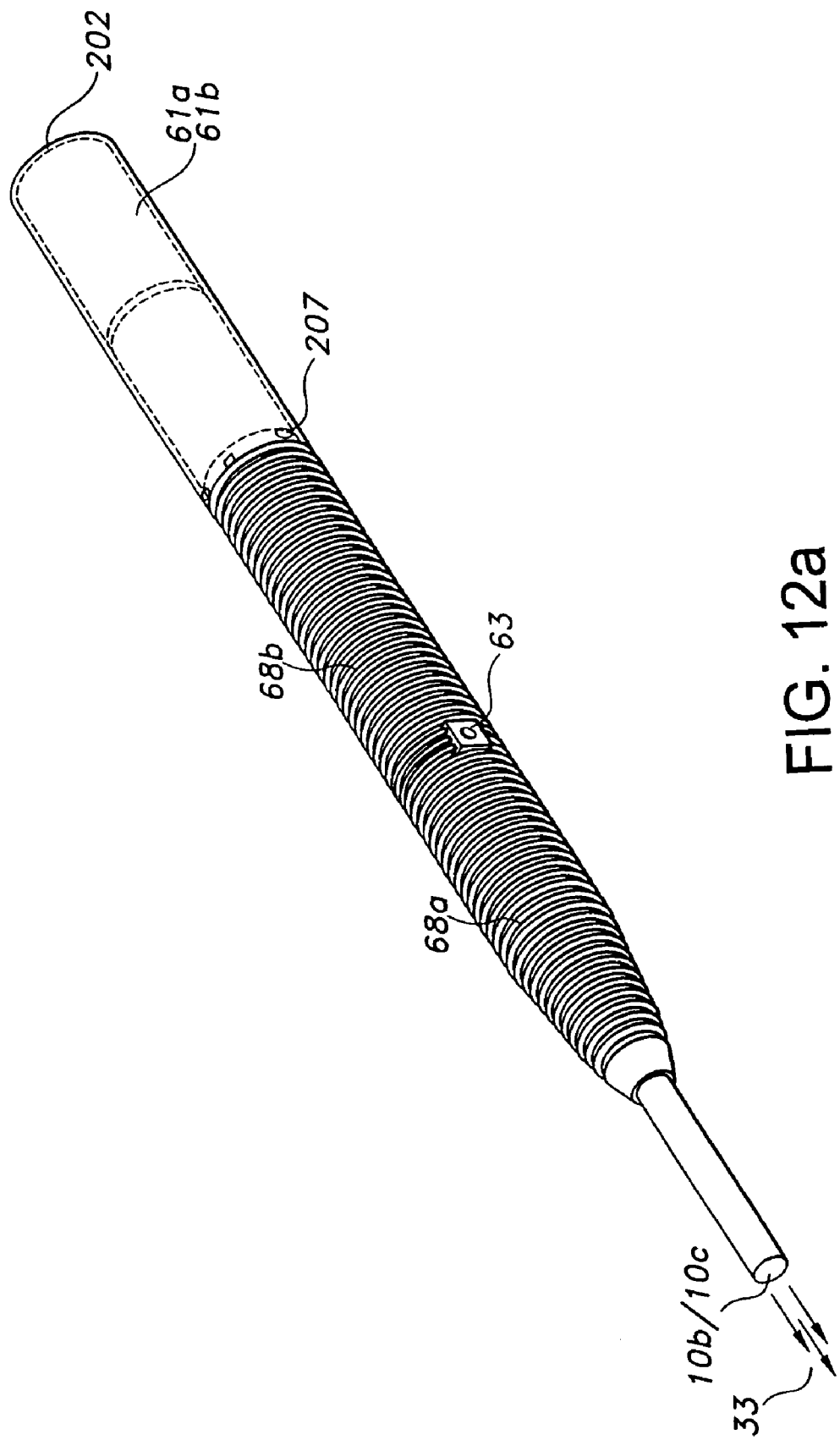

FIG. 12 shows an exploded view of the LED/heat pipe assembly as it is assembled into one or more heat sink 68 with battery pack 61a/61b. The heat sink is actually two electrically isolated heat sinks 68a and 68b that when "shorted" by switch 63 complete an electrical circuit from the positive battery lead that contacts the tip opposite the LED 10 of the copper heat pipe 64, through the LED 10, solder and wire path 201, through the sleeve 112 into the cone section of the heat sink 68, through the closed switch 63 into the bottom section of the heat sink 68, through the battery pack 61a/61b and into the, cathode end of a battery (or batteries) 202. The two heat sinks 68 may preferably be anodized aluminum or some other conductive material that may be electrophoretically coated with a non-conducting polymer. The two heat sinks 68 may be bonded together with non-conducting adhesive (not shown) and the heat pipe 64 through hole 203 may be filled with an electrically insulating, but thermally conductive compound. The heat pipe/sleeve assembly may be held in place in the heat pipes by a simple set screw 204. The hole 203 is simply a long hole through each heat sink 68a and 68b that accommodates the heat pipe 64 and it may or may not have a dielectric layer. The fins 219 shown in FIG. 12b on the heat sink(s) 68 may be either radial and/or at an angle in relation to the heat pipes and/or they may be axially disposed.

The light from the LED 10 emits through a transparent dielectric concentrator 205. The light emission direction is shown by arrows 206. The most preferable embodiment contains one high power LED 10 on the end of the heat pipe. However, multiple LEDs to can be used at one or more cantered wavelengths, Also the LED(s) may preferably be mounted on a small heat sink or heat spreader that is in turn mounted near or on the end of the heat pipe. Multiple heat pipes may also be employed. Individual or arrays of lenses may also be employed. If the lens is a reflector it may be faceted or it may have smooth walls. It may be totally internally reflecting or it may be a metallic or dielectric coated wall or polished wall reflector.

FIG. 12a shows the light emitting diode 10 through reflector/lens 10a/10b. The sleeve 112 (not shown) is electrically connected to heat sink 68a. Switch 63 completes the electrical circuit between electrically conductive heat sink 68a and heat sink 68b. Battery pack 61a/61b is also electrically active (current carrying) and its function, beyond containing the batteries is to connect the cathode end of the battery 202 in the heat sink 68b. Also, O-ring 207 is shown and is attached at the connection of the heat sink 68b and battery 202 to seal out water and to provide a smooth (tactile) feel during the thread rotation action. The light emitting device 10 shown in to FIG. 12a may preferably be powered by an electric cord. The device may be convective cooled through the many fins 208 as will be shown in FIG. 12b. The device may have a gravity or tilt-type shut-off switch as will be shown in FIG. 12c within the hand piece shown to prevent the device from being operated in a substantially non-gravity aided wick orientation. The orientation switch may be of MEMS type construction and could switch on or off depending oil any chosen orientation. The device could also be used in an acne (or other skin treatment) application. In the acne treatment application, it may have a lens to further diverge or shape the emitted light (this is true in all embodiments). The preferred wavelength for acne treatment is in the blue but sometimes other wavelengths are used, such as yellow. The light may preferentially target drugs and/or may be used for acupuncture. Furthermore, the device may further desirably have the heat pipe 68 and sleeve 112 together bent at an angle.

Figure 12B:
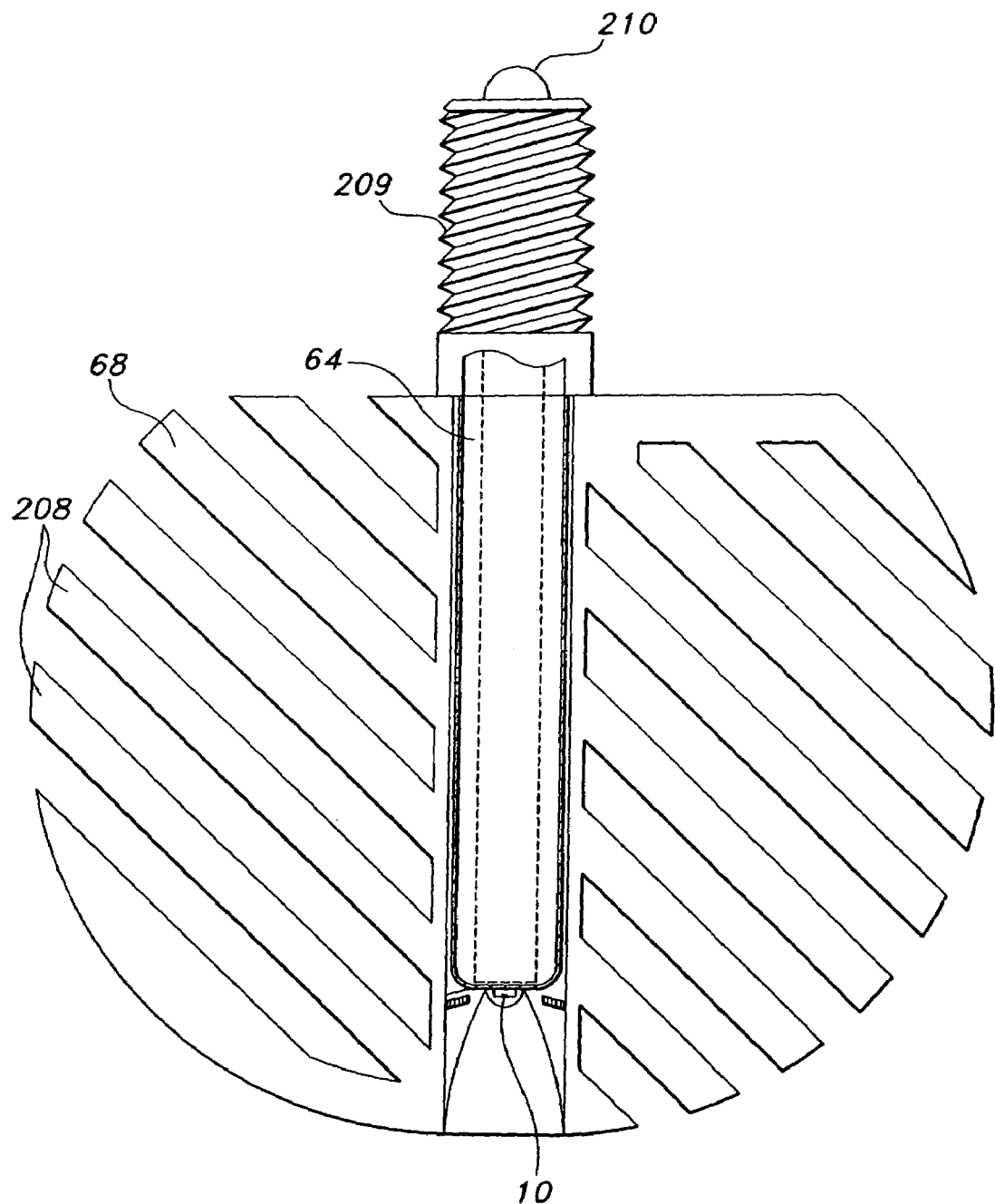

FIG. 12b depicts a solid-state lighting application wherein at least one LED die 10 is bonded to at least one heat pipe 64 which is then further bonded to at least one or more heat sinks 68. In the preferred embodiment, the heat pipe 64 is oriented substantially down or vertical with the LEDs 10 being at the lowest point near to the ground, In this way the heat pipe 64 is said to be aided by gravity. The LED/heat pipe assembly is the same assembly depicted in FIG. 11a, except that the heat pipe 64 is shown bonded in the somewhat spherically shaped heat sink 68 that has fins 208 that may be machined, or most preferably molded in place. If it is molded it may be thixoformed, die cast, permanent molded, or other similar process. These processes facilitate the high volume and low cost that is needed for a solid-state lighting product. All heat sinks 68 or heat exchangers 76 in this application may be molded and may be made from an alloy of magnesium. It is understood that multiple LED dies 10 at multiple centered wavelengths and with heat pipes 64 (that may be bonded in one or more heat sinks) may be used. The LEDs 10 may be electrically individually addressed and individually modulated or they may be an electrical series, parallel, or other electrical connection. Threads 209 on top portion of the heat pipe 64 may be an electrically "active" component and they may facilitate an anode or cathode or ground connection. If the heat sink 68 is dielectrically coated and the threads are uncoated, they may be of monolithic or at least of electrically continuous design. Electrical contact 210 above the threads 209 which is preferably the cold end tip of the heat pipe 64 is either the anode cathode or ground, but is of preferably the reverse polarity of the threads 209 and electrically isolated from it. An electrical circuit could preferably be placed between electrical contact 210 and the power source such as within the threaded area 209 that may step LIP or step down current or voltage. This circuit may be present in any embodiment in this patent application. The device depicted in this drawing could be threaded into a heat sink 68 that may be electrically active and could absorb heat, as well as supply electricity.

Figure 12C:
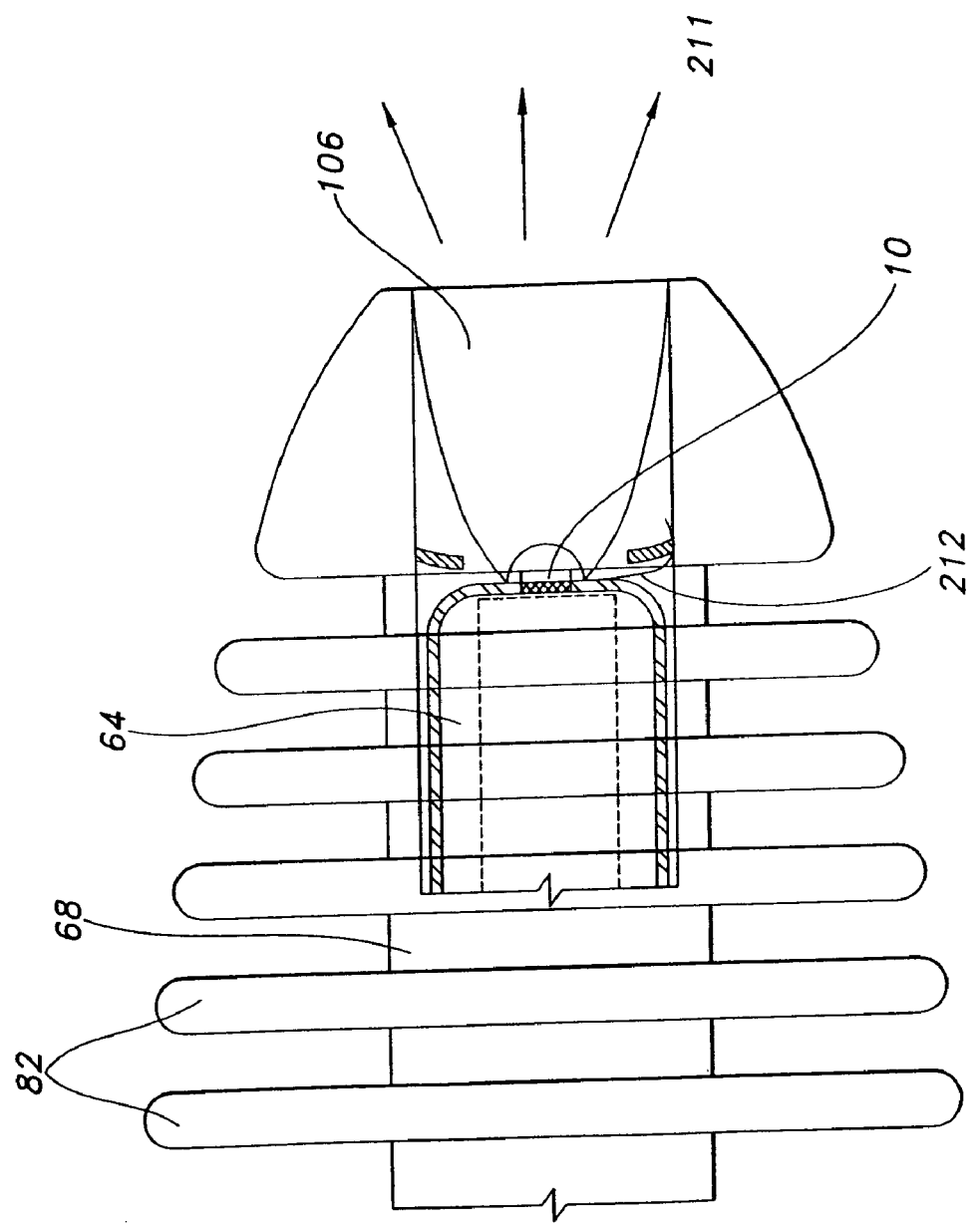

FIG. 12c depicts the front section (light-emitting end) of the light source embodiment of the present invention. This light source may be portable and fit easily in the human hand. Again, like most embodiments in this patent application, a heat pipe 64 (or heat pipes) is (are) used to distribute heat rapidly away from an LED 10 (or LEDs) to much larger fins on a heat sink 68. A reflector 10b is shown and this reflector may be made adjustable in that the cone angle of light 211 may be adjusted by the operator or during manufacture of the light source. Wire bond 212 is shown running from the die(s) 10 to the heat sink 68. The heat sink 68 may be anodized aluminum thereby shielding the operator from potentially adverse electrical shock because anodized (aluminum) is a very good electric insulator. The wire bond 212 obviously contacts a spot on the heat sink 68 that is not anodized (masked during manufacture). The light source 211 may preferably have a rotating battery pack that opens or closes the electrical circuit when rotated approximately one-quarter turn.

Figure 12D:
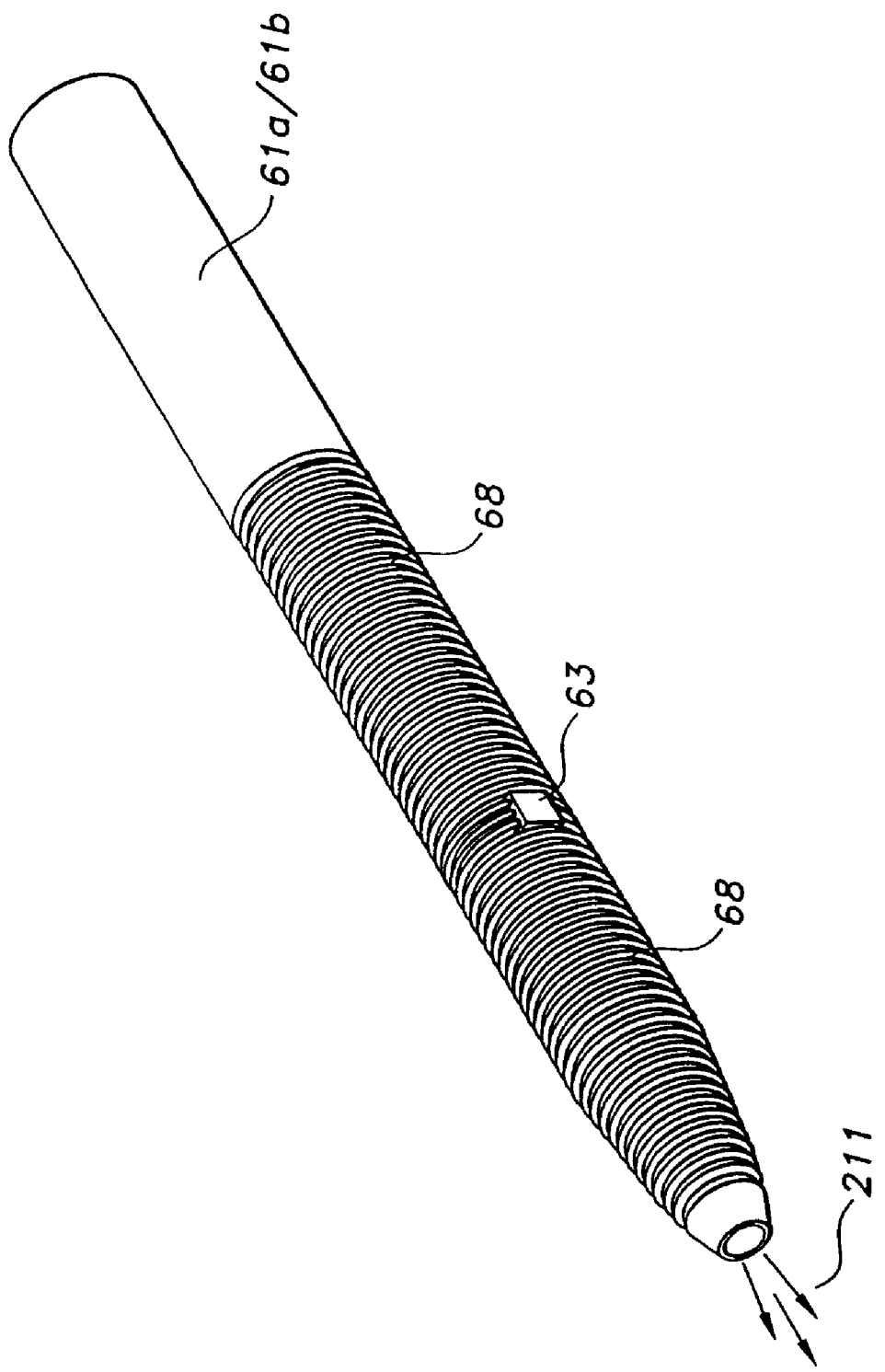

FIG. 12d shows the entire light source whereas FIG. 12c showed only the front section referred as the "nose" section. The LED light is shown emitting light out of the by arrows 211. Heat sink(s) 68 are preferably connected electrically by switch 63. The battery pack 61a/61b preferably is affixed to heat sink 68 by mechanical threads (not shown) in an electrically continuous manner.

Figure 12E:
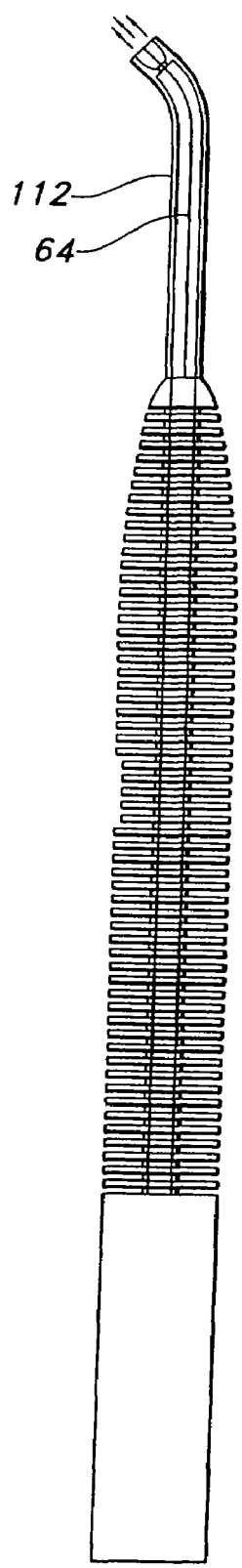

FIG. 12e depicts a heat pipe 64 and surrounding sleeve 112 bent at an angle, could be useful to many of the embodiments described herein.

Figure 13:
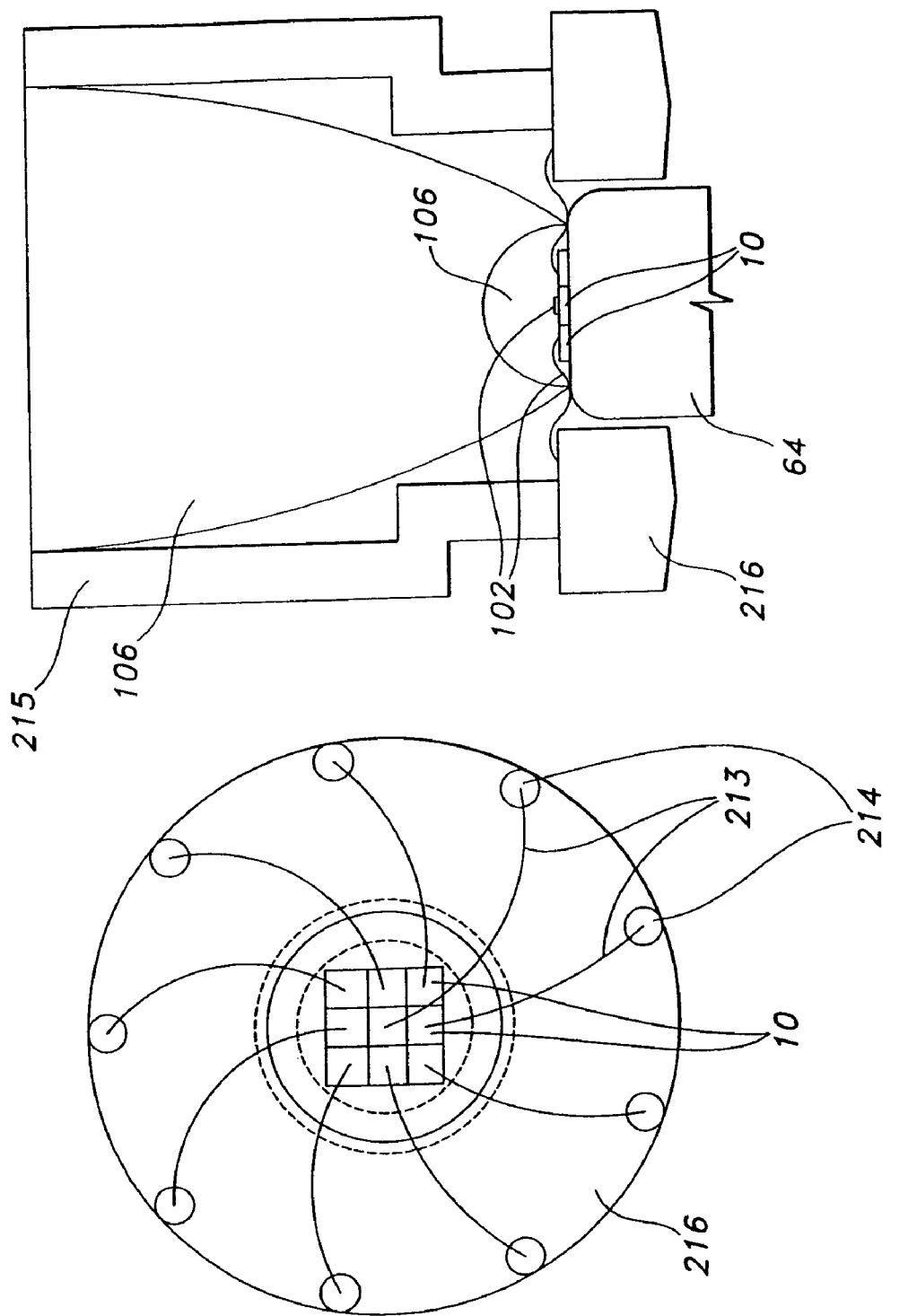
FIG. 13 shows a perspective view of the LED/heat pipe device on a circuit board.

FIG. 13 shows the embodiment of the invention wherein multiple LEDs 10 are bonded to at least one heat pipe 64 and rested on a circuit board 216. The LEDs 10 are individually addressable and at least one wire 213 is bonded to each LED 10 and the other end of each wire 213 is then bonded to electrical bond pad(s) 214. It must be understood that LEDs do not necessarily require wire bonds, because SMT type bond pads may be employed on the LED with the requisite circuitry deposited where needed on the heat spreader. If pulse width modulation (PWM) is employed it is usually advantageous to have the LEDs mounted "n" side up (i.e., "p" would be bonded to heat spreader) because this arrangement is cheaper and more electrically efficient and requires less parts in the circuit. These bond pads 214 are electrically isolated from each other. In this drawing the LED(s) 10 are shown with an electrically active heat pipe(s) 64 although electrically neutral heat pipe(s) may be used in this embodiment as well as any other embodiment in this patent application. The heat pipe 64 may be a common anode 11 and each LED 10 would then be controlled by varying the resistance of a resistor located between the die/wire bond and the power supply cathode. If the heat pipe 64 is a common cathode 12, then the current leading to each die 10 may be modulated directly (i.e., pulse width modulation and/or direct current modulation). This figure depicts a total of nine LED die. Any number of die from one to over one hundred may be employed. Also, any number of centered wavelengths from one to more than one hundred may be employed. Most preferably, wavelengths from the UV to the IR are used, with 400 in to 700 nm being the most preferable. This wavelength range may be used in other embodiments in this application. The TIR reflector 10b is also shown. It is held in place by lens holder 215. The circuit board and/or circuit board holder 216 is shown on which the lens holder 215 is placed. The hemispherical concave-surface 114 in the reflector 10b is shown. It is preferably of a higher refractive index than the material used in TIR reflector 10b so as to allow more light to escape the chip, due to TIR in the chip. Also, light rays may advantageously be bent at hemispherical concave surface due to refraction caused by the differing refractive indices. Aspherical, parabolic, elliptical, hyperbolic or diffractive surfaces may be substituted for the hemispherical surface. The outside diameter of the heat pipe 64 is shown in the drawing by the solid line drawn in a circle on the left. The nine LEDs 10 depicted in the figure may be an assortment of red, blue, and green emitting LEDs. It is understood that instead of three LEDs of each color, only three LEDs total may be used (i.e., one green, one blue, and one red). In the figure, rectangular (or other shape) strips of each of the three primary colors could take up the space of three of the nine squares shown in the LED 10. In other words, each of the three primary colors may take up one-third of the available (depicted) space. This in some way might imply equal impedance for a given die area for each color. Although this might not be true in all cases. Any organic and/or polymer LEDs could be employed in any embodiment of the invention. Red inorganic LEDs may preferably be used that are smaller in area than the blue or green LEDs. Also, due to the human eye's ability to detect different colors at differing apparent intensities (i.e., sensitivity) more red than green, and more blue than green, LED area may preferably be employed.

Figure 14:
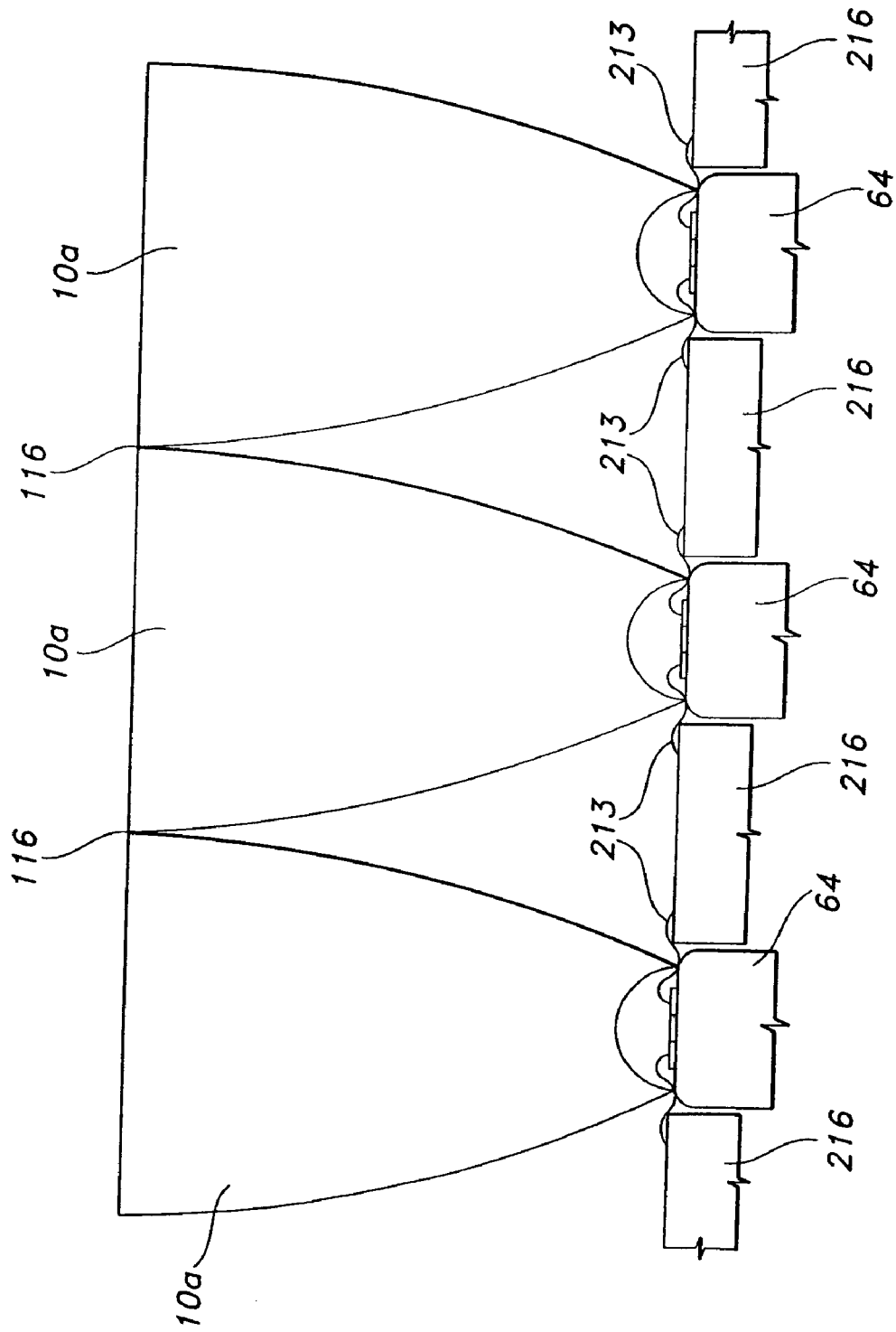
FIG. 14 shows an array formed of more than one device of FIG. 13.

FIG. 14 depicts the device of FIG. 13 in an array formed of more than one device of FIG. 13. Actually, in FIG. 14 an array of only three devices are shown for clarity. Between each heat pipe 64 is shown the circuit board 216. This circuit board may be of the conventional epoxy laminate, and/or it may be of solid conductive material such as aluminum or copper with or without a non-conductive polymer or ceramic layer (laminate). It may also be wholly or partially ceramic, such as BeO, alumina, AlN, or other. Circuit traces such as thin copper or gold or plated gold may connect wire bonds 213 leading from the LED die (or dice). The lenses 10a may touch each other and be circular at the contacting final emitting surfaces or they may be molded into a square shape at the final emitting surface and therefore have no "spacing" between them. Also, a final lens element (or elements) may preferably be employed after the final emitting surface for the purpose of further beam shaping or environmental protection. Additionally, circular holders may be employed around the lenses.

FIG. 14a is similar to the cross-sectional view of arrayed devices of the FIG. 14 with the addition of holders 98 as shown around the individual lenses or reflectors 10a/b. Such holders could be of any shape and size sufficient to support the individual lenses 10a or reflectors 10b.

Figure 14B:
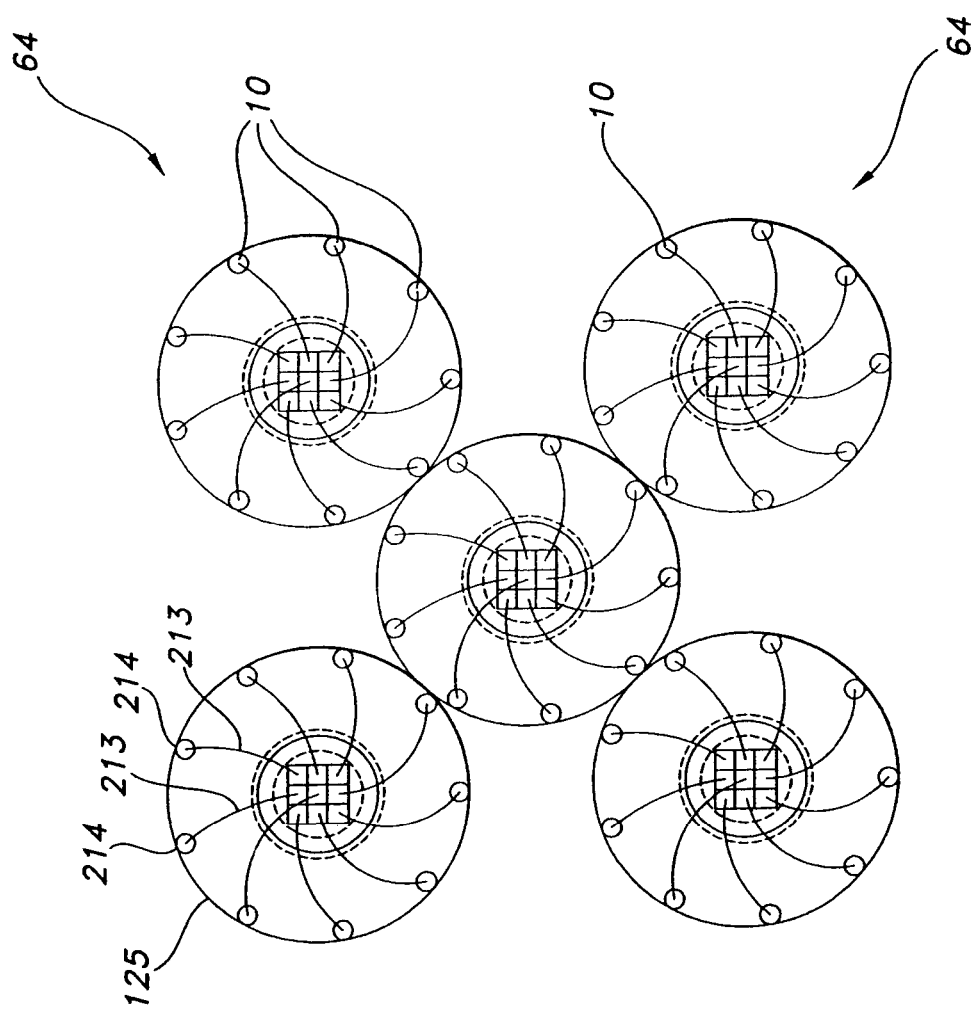
FIGS. 14b, 14c and 14d illustrate devices having multiple heat pipes with different spacing and geometric patterns including multiple LEDs.
Figure 14C:
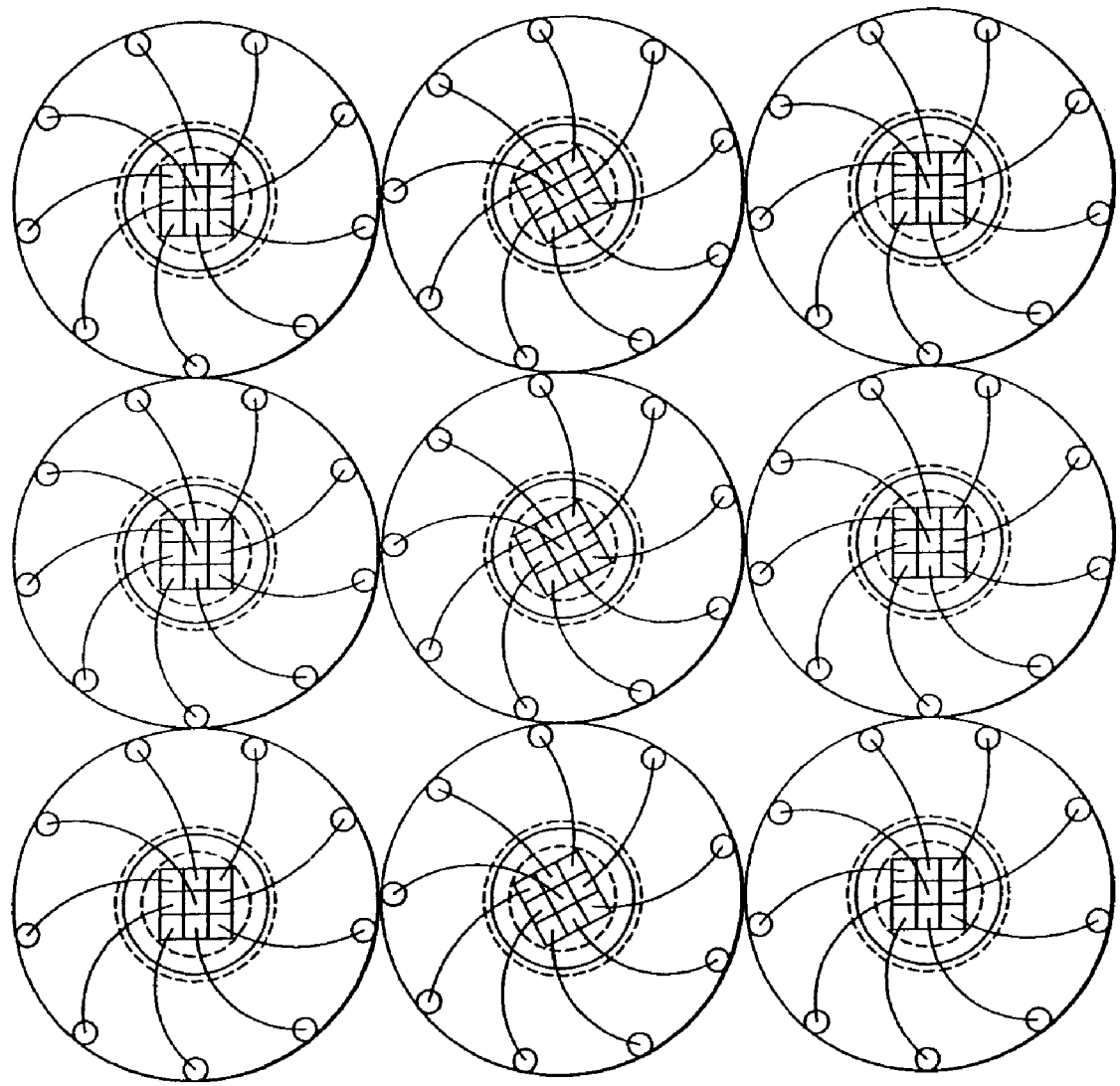
Figure 14D:
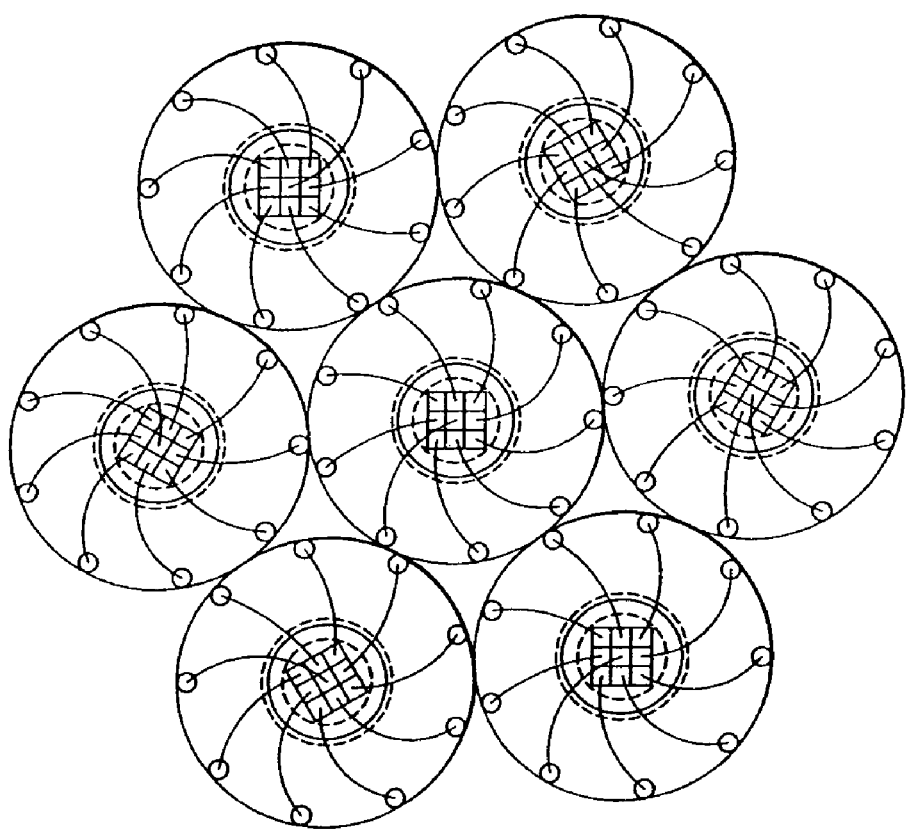

FIGS. 14b, 14c and 14d depict different "pixel" spacing and geometric patterns. A "pixel" in this case is a heat pipe 64 with the nine (or other number) shown LED(s) 10 on it. Each heat pipe itself may be individually addressable as well as each individual LED die on each heat pipe or some other combination. The ring 125 shown around each heat pipe may "nest" in a circuit board as shown in the FIG. 14e. The heat pipes 64 are shown for clarity. The wires 213 are bonded to electrically isolated bond pads 214. When the ring 125 is nested in a circuit board, a means for connecting circuit board traces to the respective bond pads 214 on the ring 125 must be employed. This means may be accomplished by contacts connected by traces and plated through vias. The LEDs 10 may then be controlled by the voltage and currents that are applied to them from the traces on the board (connected to a power source(s)), through the wires 213 and then to the LEDs themselves. The wires 213 may be attached (as in all embodiments) to the die(s) 10 by a wedge, ball, or other bond. Wedge bonding is preferable because the wires stay more parallel to the board surface. Ball bonds can be advantageous in that the wire sticks out vertically from the chip and tends to attract the die encapsulating polymer in a manner that pre-wets the chip and greatly reduces the formation of bubbles as the lens or reflector is slowly lowered over the die(s).

Figure 14E:
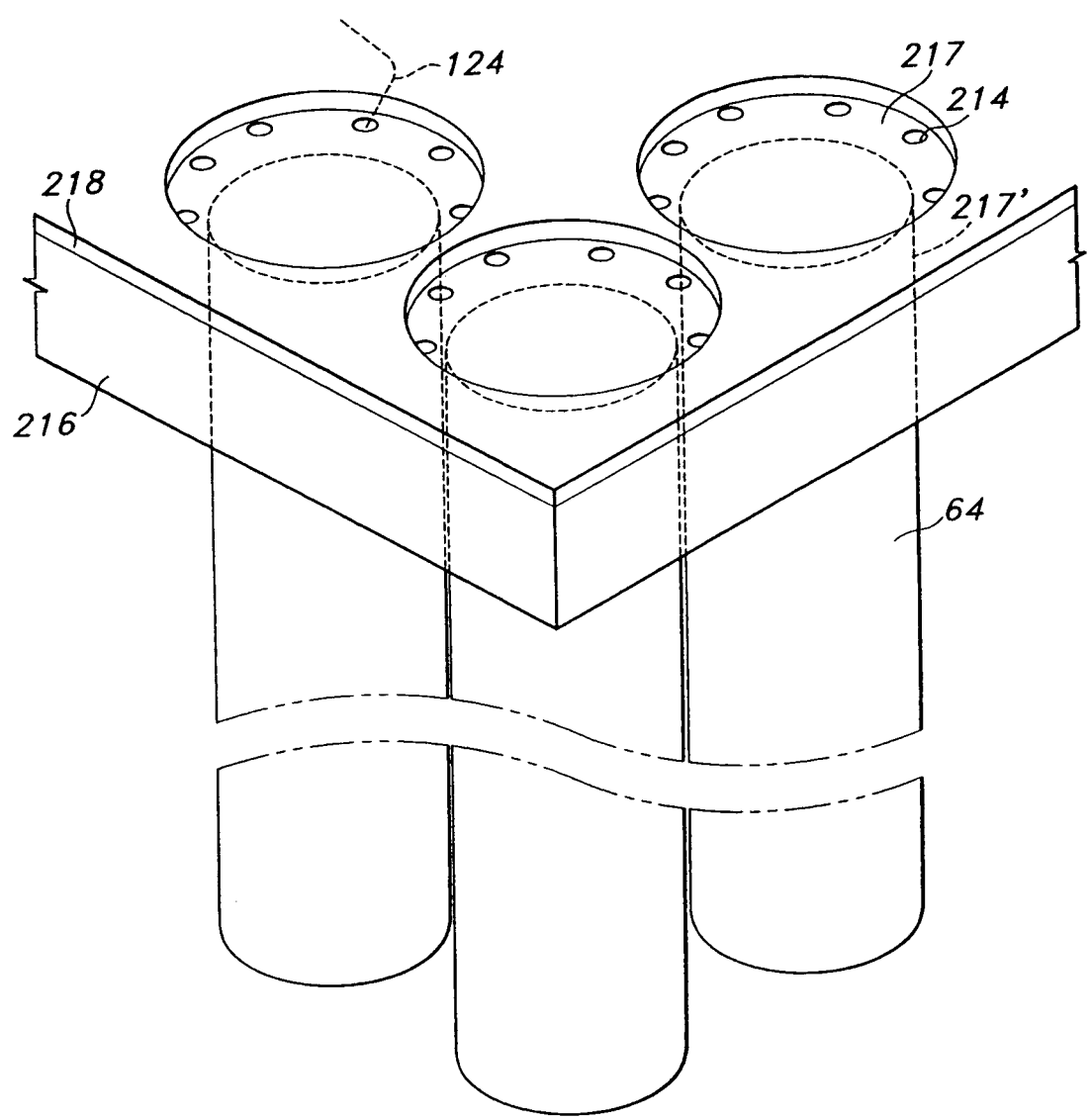
FIG. 14e shows the devices of FIGS. 14b, 14c and 14d placed in the circuit board.

FIG. 14e shows the blind female recesses in the circuit board that accommodate the rings 125 from the devices shown in FIGS. 14b, 14c and 14d. Contacts, vias, and traces are shown. The preferably blind female recess(es) 217 in the board 216 are shown. There are also preferably blind female recess(es) 217' depicted by dashed lines in the board(s) that accommodate the heat pipe(s) 64. There is a thin section of preferably board material that is of high thermal conductivity between the two blind holes or recesses 217 and 217'. In the preferred embodiment, 217 and 217' are substantially co-axial; however this need not be the case. There may preferably exist a board laminate 218 preferably bonded an board 216. In this embodiment of the invention as shown in FIG. 14e, the recesses 217 are actually through hole(s). Bond pads 214 that are aligned in FIG. 14b are shown with circuit traces on board 216. It is important to mention that through wires 213 under bond pad(s) 214 in FIG. 14b are not shown in the figure but must be present in order to make contact with bond pad(s) 214. The rings 125 from FIG. 14b may be square (or some other geometrical shape) and would be accommodated by a like shaped recess 217'.

Figure 14F:
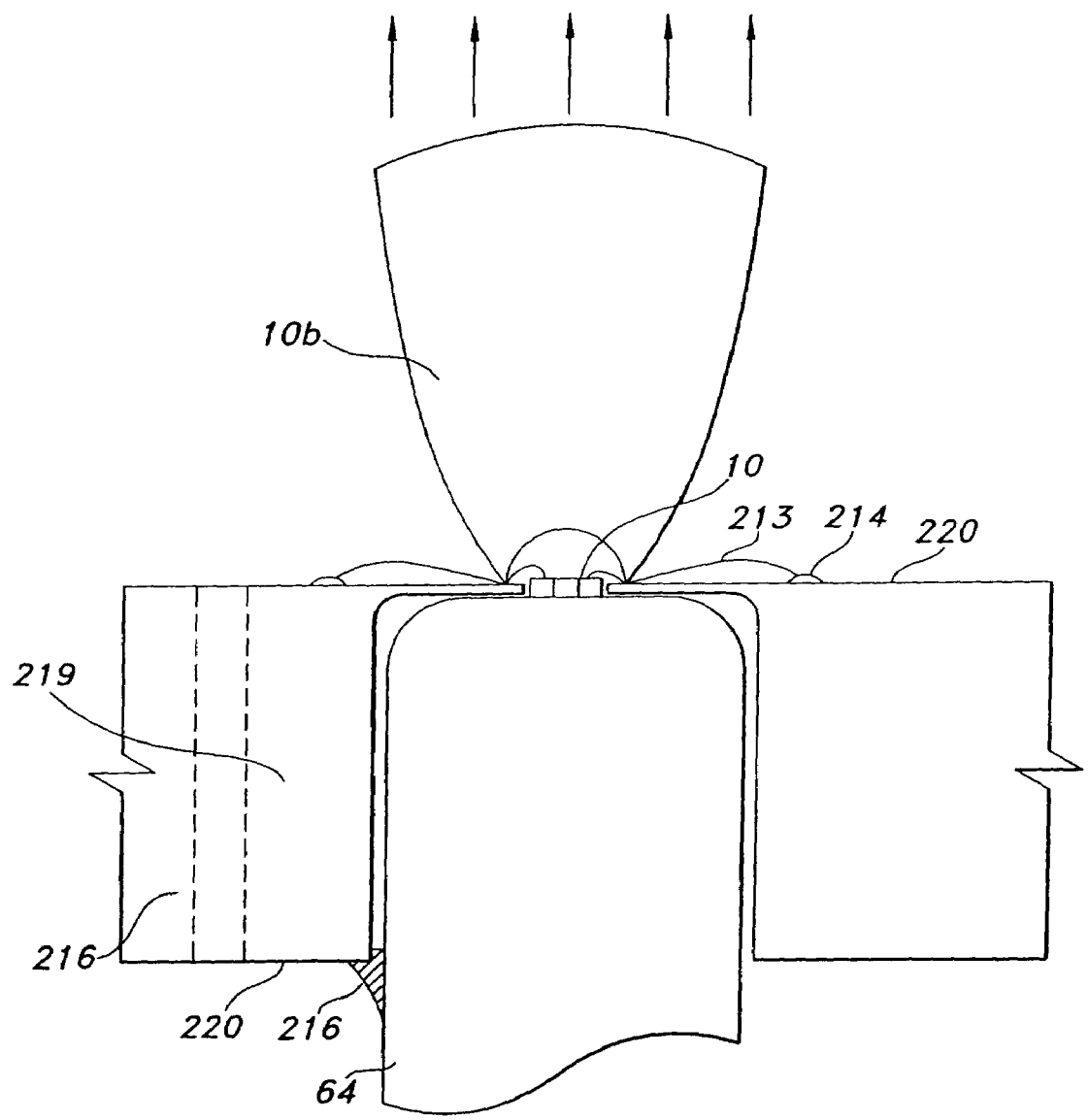
FIGS. 14f and 14g show a device having a single heat pipe including multiple LEDs connected to a circuit board.

FIG. 14f shows a device somewhat similar to the one in FIG. 14b. It shows the heat pipe(s) 64 co-axial to a hole through board 216. Board 216 could be a "ring" similar to the ring 125 in FIG. 14b. The board 216 is shown with a thin wall surrounding the multiple dies 10. In this drawing, the dies 10 are shown in a "p"-side up embodiment. The active epitaxial layer is depicted on the top edge of the die 10. Many different LED or laser diode structures and designs may be employed in all embodiments. In particular, LEDs with an optically resonant structure may be used, as well as LEDs or LDs that utilize "quantum dots". Hole 219 is shown in the board 216 and wires 213 are shown leading from the individual die 10 to their respective bond pads 214 and then to respective circuit traces 220. The heat pipe 64 may or may not be electrically active. If it is active, it may be the common cathode and have an electrical connection to the wire 213 in the board 216. Wire 213 may be conductive adhesive connecting the heat pipe 64 to the circuit trace 220. Reflector 10b is shown. Light emission is shown by the arrows pointed upward. The board 216 may be affixed to a larger board with hardware or some passive locking arrangement to that individual LED/heat pipe assemblies may be changed as they wear out or technology warrants. Assemblies with multiple LEDs at multiple centered wavelengths in or near the visible spectrum as depicted in this figure and embodiment as well as others in this patent application are ideal for automated stage light assemblies, due to their compact, light weight, and high optical power, which may preferably be computer controlled to change color, intensity, hue, etc.

Figure 14G:
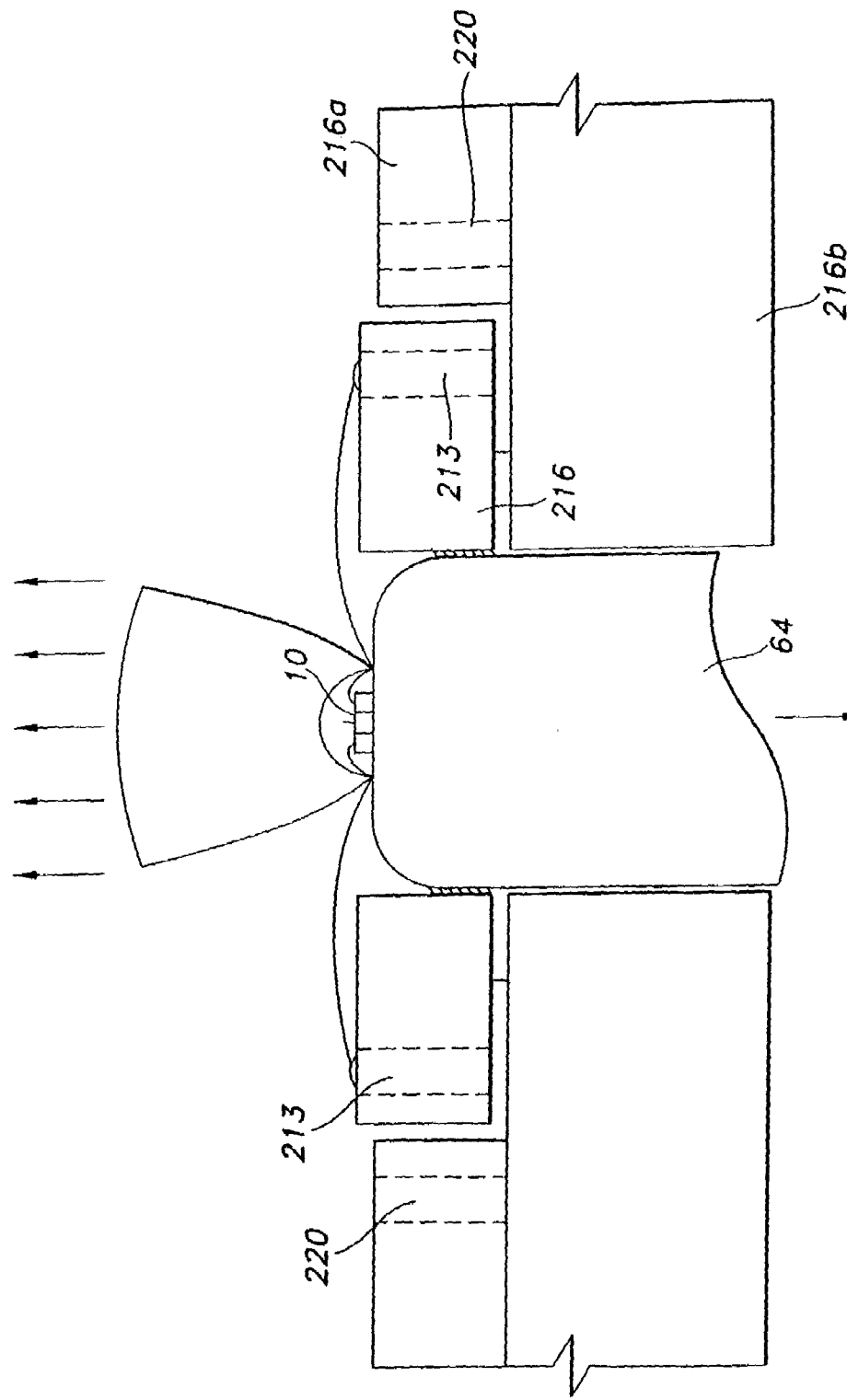

FIG. 14g shows heat pipe 64 inserted in a through hole 219 of board 216. Reflector 10b is shown with LED dice 10. A two part laminated board with traces between the layers is depicted as top layer 216a and bottom layer 216b. Wires 213 in board 216 are shown as wires making electrical continuity between the traces 220 sandwiched between layers 216a and 216b and the traces 220 on top of 216. It should be noted that layers 216a and 216b, comprising the circuit board 216, are optional in that the light can function without a circuit board 216 and another means of connecting wires from a power supply to the bond pads 214 can be employed in various applications, for example, stage lighting. Again, fins may preferably be attached to the heat pipe 64 to employ convection or forced air cooling.

Figure 15A:
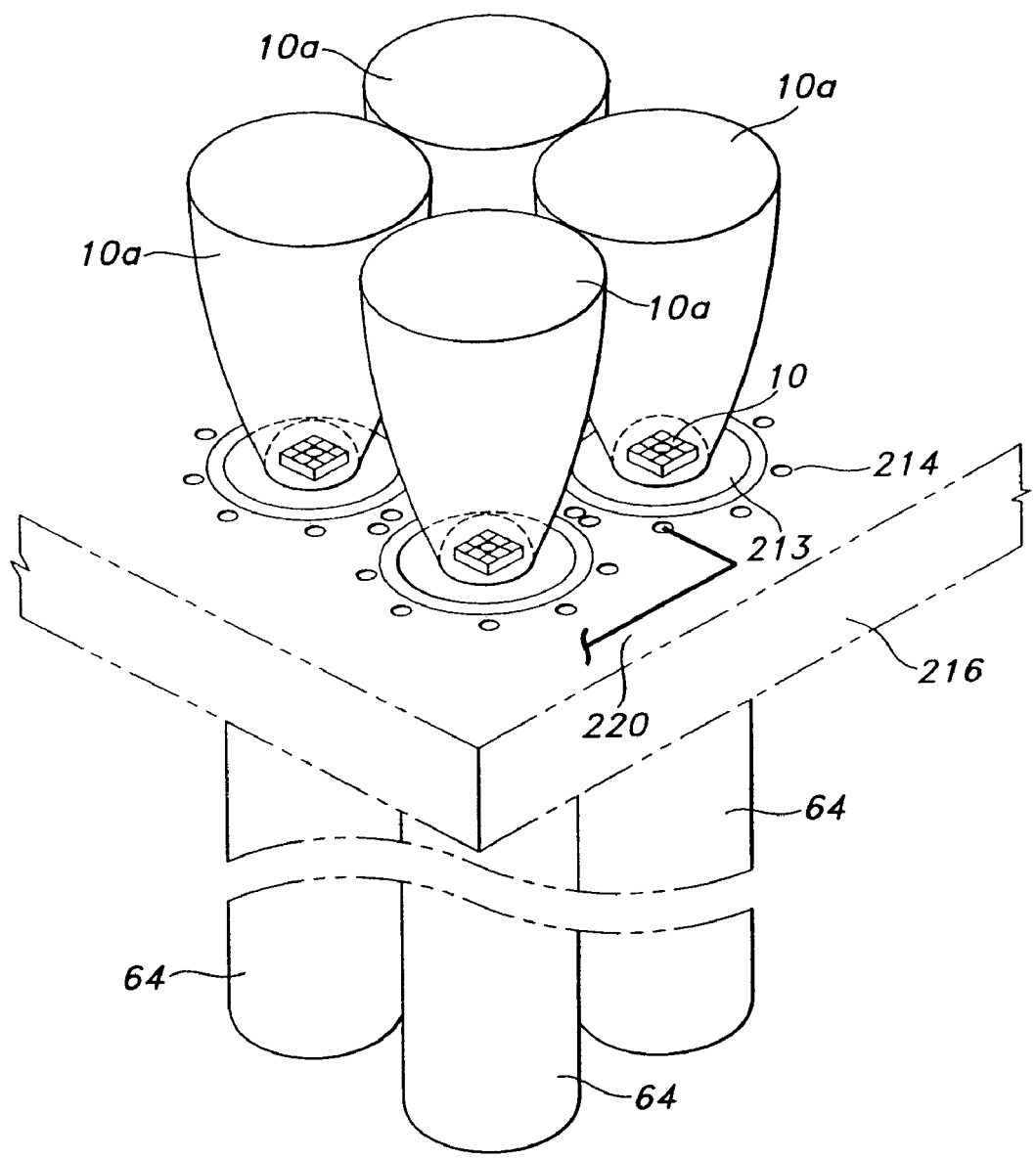
FIGS. 15a and 15b illustrate a perspective view of multiple LEDs on heat pipes arrayed on a circuit board.

FIG. 15a shows four "pixels" (LED(s) on heat pipe devices) that are arrayed on a circuit board. Only four devices (each considered a "pixel") are shown in this drawing for purposes of clarity. Actually, all array of pixels such as 48 by 64, or 48 by 32, or 24 by 16 for example may be employed. Examples of pixel spacing preferably might be center to center spacing of 12 mm, 18 mm, 23 mm, 35 mm or 50 mm. These full-color video displays can desirably bring television-like quality to billboard size screens that may be used for advertising or other purposes. Provisions for adjustment for uniformity, dimming, brightness, hue, color space conversion and gamma correction may be employed. A portion of the circuit board 216 is shown. On the tip of the heat pipe 64 nine individually addressable LEDs 10 are shown. Each of those LEDs 10 have a wire that connects to a bond pad 214 on the circuit board 216. Please note that in this embodiment there is not a separate ring 125 as shown in FIGS. 14*b*, 14*c*, and 14*d*. The wires 213 in this embodiment lead from the separate LEDs on the heat pipe(s) to separate, permanently affixed bond pads 214 on the circuit board 216. Only one wire 213 in the entire drawing is shown, for clarity, as well as only one abbreviated circuit trace 220. It should be, obvious to those skilled in the art to connect individual wires from individual LEDs to individual bond pads, and then these bond pads to appropriate circuit traces to light up the LEDs. Note how the multiple heat pipes 64 form a "pin-fin" type heat sink. All of the circumferential surface area of the heat pipes is used to conduct heat to the ambient air that flows either by natural or forced air convection between the pins (a.k.a. heat pipes) and the heat pipes may have fins attached in any orientation to further increase surface area. The space between the heat pipes allows air (or other medium) to circulate and cool the heat pipes. The fins could actually be all monolithic in a honeycomb-type design wherein the bare heat pipes slide into holes in the all monolithic honeycomb heat sink. This heat sink maybe made of any thermally conductive material, and it may or may not be forced air cooled. If the fins are not monolithic, but are joined to heat pipes, they may be at a 45° angle (or so) to the heat pipe orientation, as well as at an angle (or so) to the horizon to facilitate naturally convective flow of air because heat will rise up through the fins and draw cool air in behind. Also, the, air will be forced to impact the fins more directly than if the fins were mounted perpendicular (vertical) to the horizon. As in all embodiments in this application the heat pipes may have some other working fluid than water or may have some other substance added to the water. In the alternate flashlight embodiment, for example, alcohol (glycol, methanol, etc.) may be added to protect from freezing. Also, other materials, such as aluminum, could be used instead of, or in conjunction with copper for the body (wall) or heat pipes. Lenses 10*a* are also shown. These may be of the TIR variety or refractive, diffractive, reflective, or a combination. When the LEDs 10 on one of the heat pipe 64 are turned oil in some combination. The pixel can be thought of as "on" or "active". In general, each heat pipe's LEDs would be some combination of individually addressable red, blue, and/ or green LEDs. As in all embodiments in the application "white" LEDs may be employed. By computer and/or algorithm control of the pixels, full motion video can be seen from some distance from the array of pixels when they are shining (emitting light in a direction) towards the viewers. Of course, an array might be used for other purposes such as curing glue or would healing or other medical applications. It must be understood that the board that the LEDs and heat pipes are mounted to may be curved instead of flat and this particular embodiment would be useful for some cosmetic applications where a curved board may surround the human face with the light shining on the skin to reduce wrinkles or blemishes, etc.

Figure 15B:
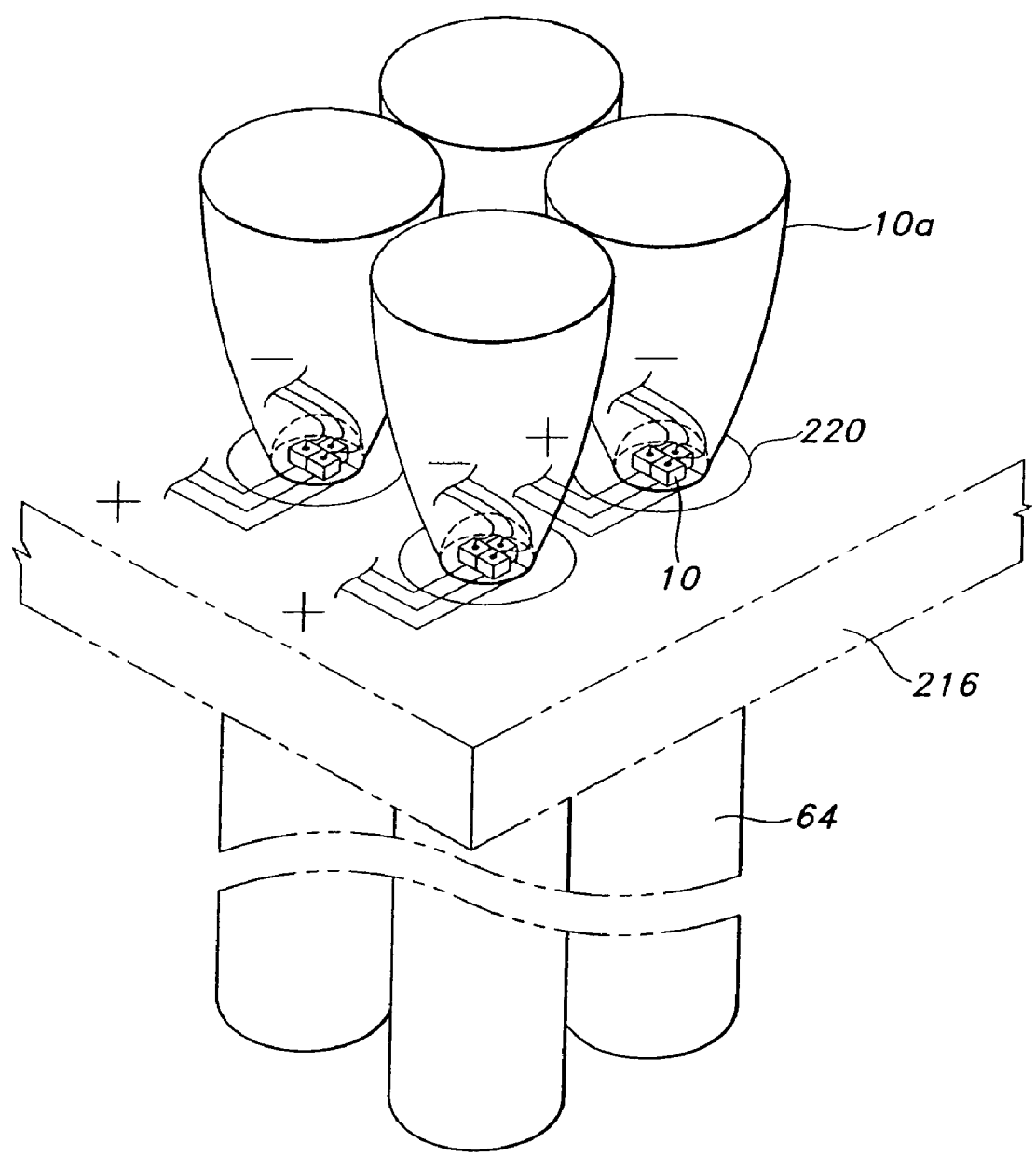

FIG. 15*b* an array of heat pipes 64 that are inserted and bonded in blind holes in a board 216. The blind holes 221 are more clearly shown in FIG. 15*c*. The board 216 may be a printed circuit board or simply a plate of metal (or other conductive or non-conductive material) with circuit traces 220 leading to the LEDs 10. A "group" of three LEDs are shown in this drawing for clarity. One or more LEDs, at one or more centered wavelengths may be used. This drawing also shows only three LED "groups" (the fourth is hidden), four lenses 510*a* and three of four heat pipes 64. It is understood that those few parts are only shown for clarity and that they represent an array of perhaps hundreds that may be on a single board 216 or multiple boards that are in themselves arrayed edge to edge. The heat pipes 64 that are in the blind holes may preferably be bonded into place with a high thermal conductivity adhesive. The blind holes are deep enough that only a thin layer of board material exists between the bottom of the hole (where the tip of the heat pipe will rest) and the top of the board 216 where the LEDs 10 will be bonded immediately above the bottom of the hole. In this way there will be minimal thermal resistance from the LED flip-chip junction, through the thin board material, through the adhesive, and into the heat pipe 64, The circuit trace 220 may be designed such that individual traces lead to LED chip anode bond pads that "p" side down flip-chip LEDs 10 are soldered to, and other traces lead to cathode wire bond pads that the wires from the cathode side of the chips are bonded to. The circuit board 216 is preferably of aluminum for light weight and thermal conductivity. It is preferably anodized to provide electrical isolation form the chip bond pads, wire bond pads, and the traces to and from them. Other thin-film processes may be used to deposit the electrical isolation layer. The board 216 may be made from an aluminum (or magnesium) epoxy or copper epoxy laminate. The arrays depicted in this application may be used for outdoor or indoor displays and signs and entertainment, or architectural lighting in which each "pixel" (LEDs immediately adjacent to a heat pipe or heat pipes) may be individually addressed to affect an image or color change. The arrays may also be used for medical, grow light, or other lighting applications. In these applications, the LEDs 10 may also (but not necessarily) be individually addressed to preferably have intensities at different the cycles more control be made available to the end user.

Figure 15C:
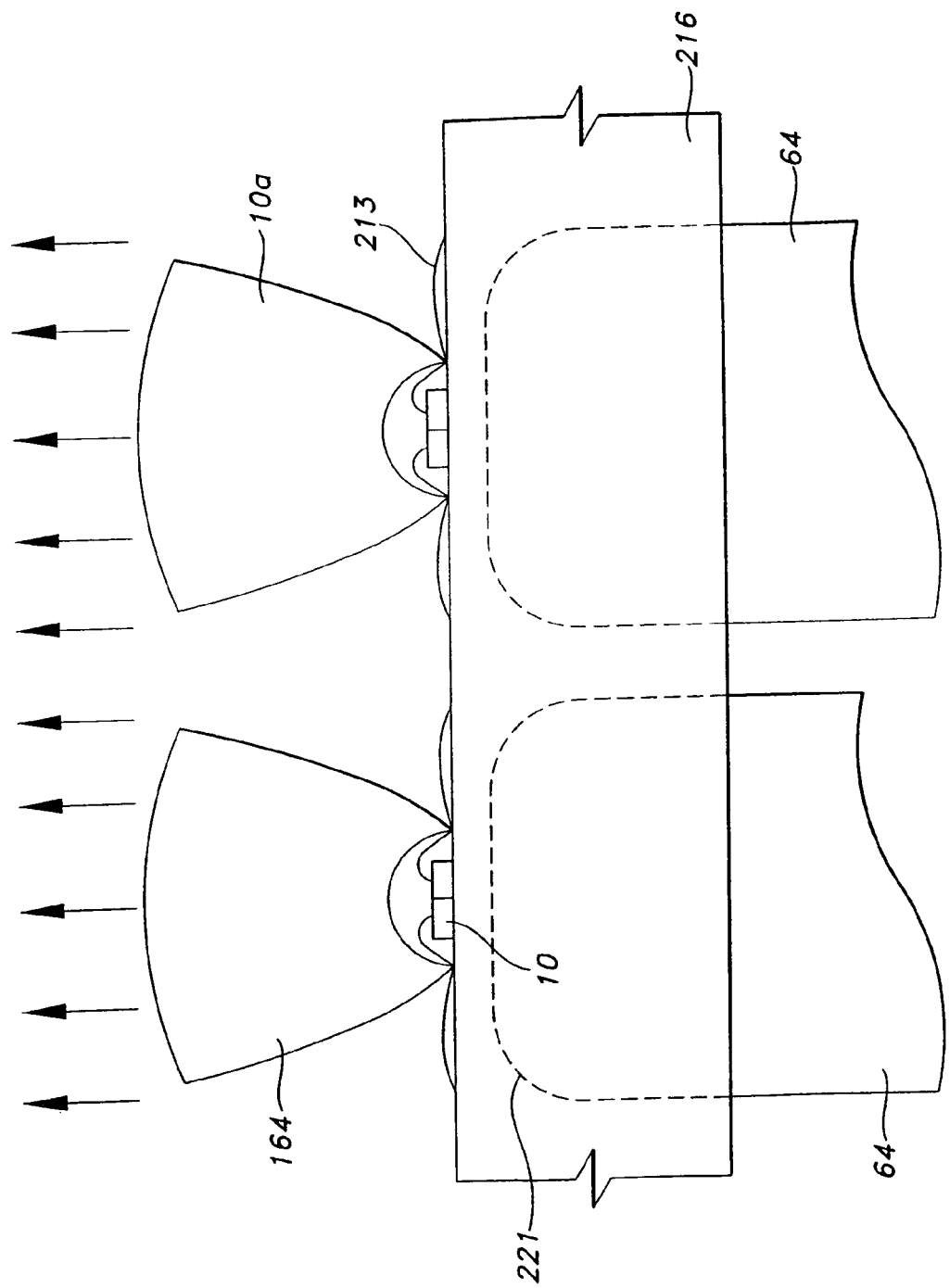
FIG. 15c is a side view of two heat pipes of FIG. 15b in the circuit board.

FIG. 15*c* is a side view of just two (of many) heat pipes 64 of FIG. 15*b* clearly showing the blind holes 221 in the circuit board 216. Only two lenses 10*a* are shown, for clarity and orientation, as well as a few wire bonds 212 and a few LEDs 10.

Figure 15D:
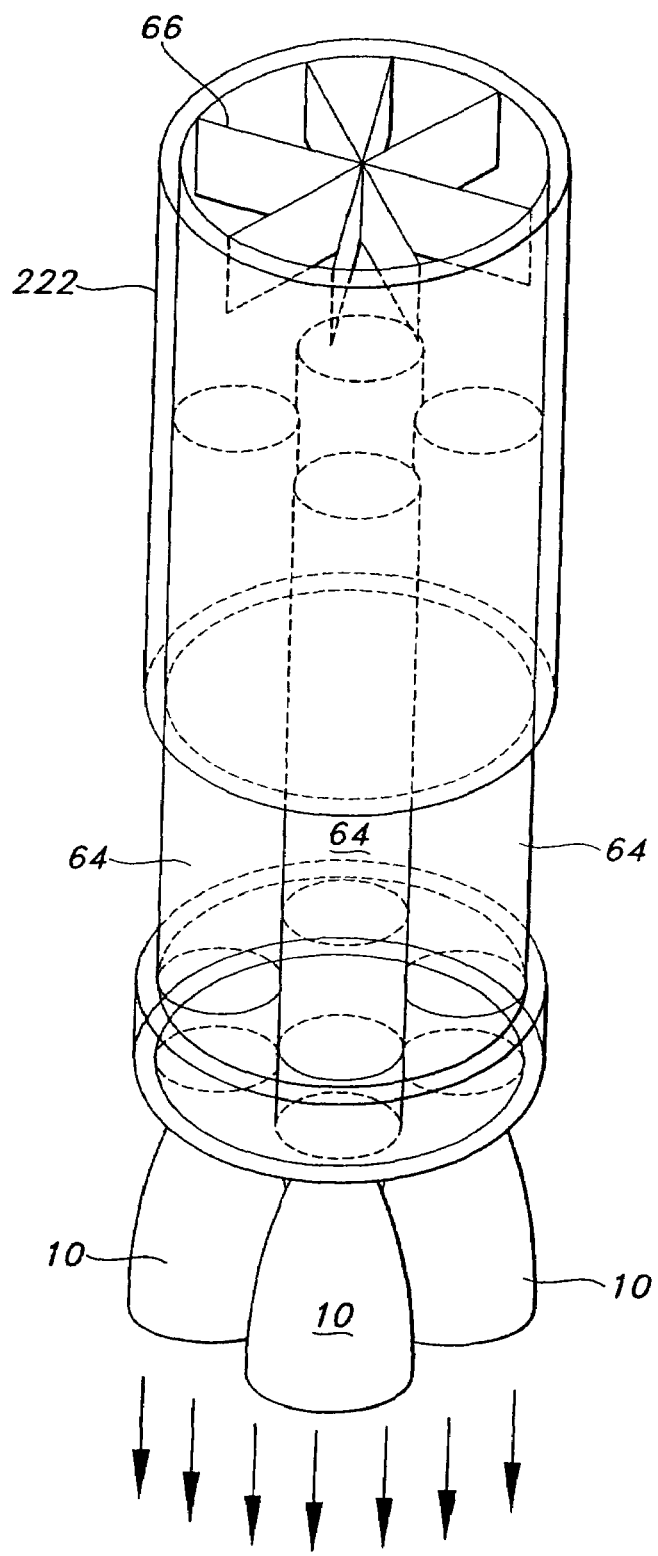
FIG. 15d illustrates a forced-air cooled hand held device according to an embodiment of the present invention.

FIG. 15*d* shows a typical forced-air cooled hand held embodiment of the present invention. It is understood that it may also be fixed or mounted (not hand held) and it might be convectively cooled, i.e. no forced-air. Typical applications might be a grow light (fixed application) or a medical PDT (arthritis) light or hair removal light. Another application may be a hand held acne reducing light at wavelengths most preferably in the short, blue spectrum (i.e., approximately 410 nm) but other wavelengths, particularly in the yellow (around 590 nm) may be used. A fail 66 is shown, with heat pipes 64 and lenses/reflectors 10*a*/10*b* and emitting LED or VCSEL light shown with arrows pointing downward. All the parts as well as the LDs 10 or VCSELs adjacent to the tips of the heat pipes 64 are enclosed in a housing 222. Electrical power may be supplied through an external cord from a power supply or from batteries or from a combination of each or rechargeable batteries. A gravity switch may preferably be employed wherein the switch would only be electrically continuous when the LEDs 10 are pointed substantially towards the ground. This would allow a gravity aided feed in the heat pipe 64.

Figure 15E:
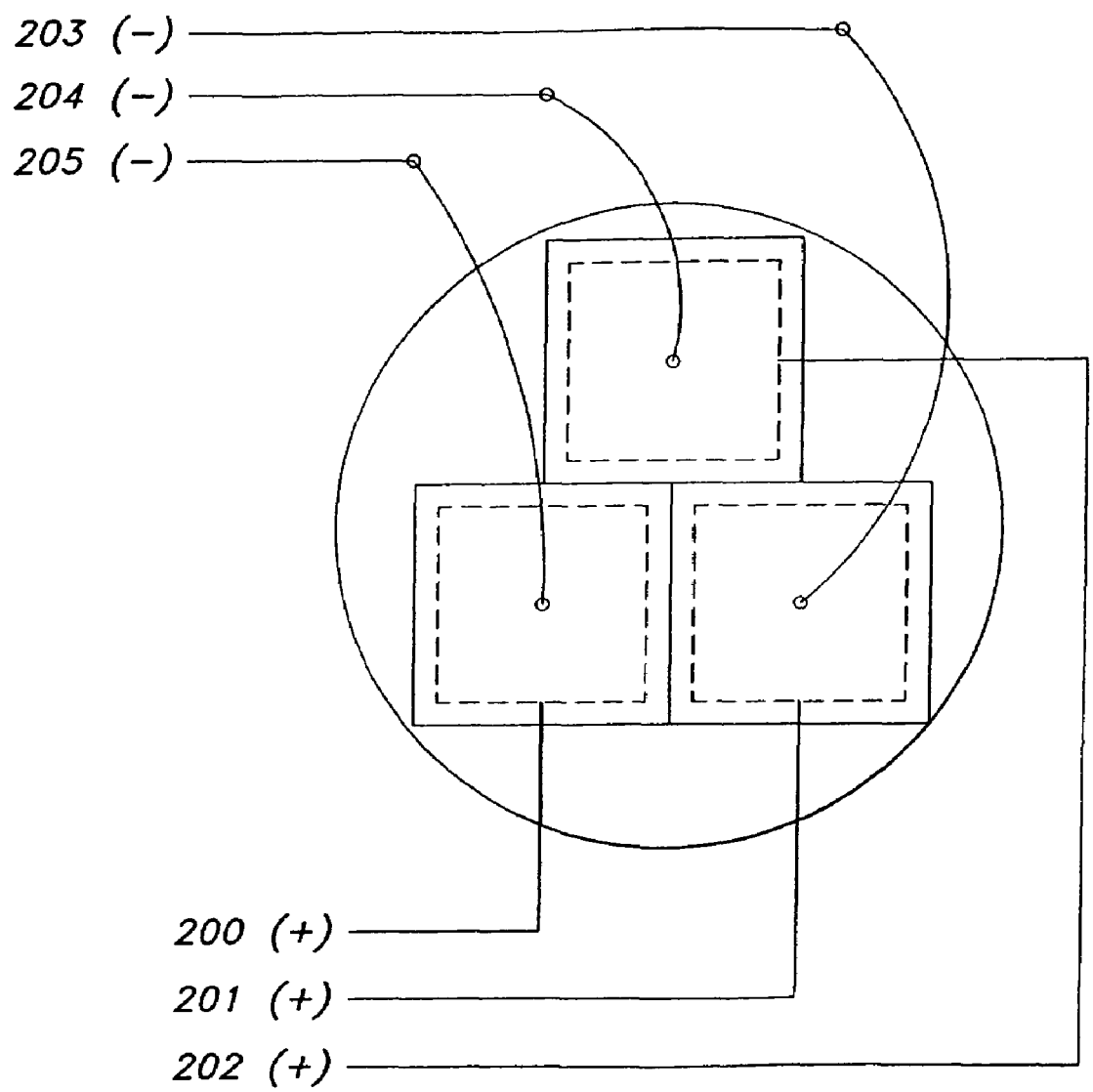
FIG. 15e shows a perspective view of multiple LEDs disposed oil the end of the heat pipe.

FIG. 15*e* depicts an embodiment of the present invention wherein three separate LEDs 10 are disposed upon the and of a heat pipe 64. It is understood that the arrays discussed in this patent application for display or other applications may or may not have a heat pipe 64 immediately below the LEDs 10. The heat pipes 64 could, for example, be only used to transport heat and may be randomly placed below the LEDs 10.

The heat pipes 64 protrude from a circuit board 216 in a direction that may be substantially opposite to the direction of the emitting light. In this manlier, they act as heat transport pins to other broader surface area heat sinks 68 or the outside diameter of the heat pipes 64 themselves which may be used as the heat emission (or heat exchanging) surface area without any additional bonded fins. Again, natural or forced convection may be employed in any embodiment. Also a phase change material (such as paraffin) may be used in any embodiment and may surround the heat pipe(s). The paraffin may have a thermal conduction enhancement material in it such as copper wool or conductive particles. The circuit board 216 that the LEDs 10 are affixed to may be affixed to another conductive (or non-conductive) plate that, in turn, has heat pipes embedded in it.

Figure 16:
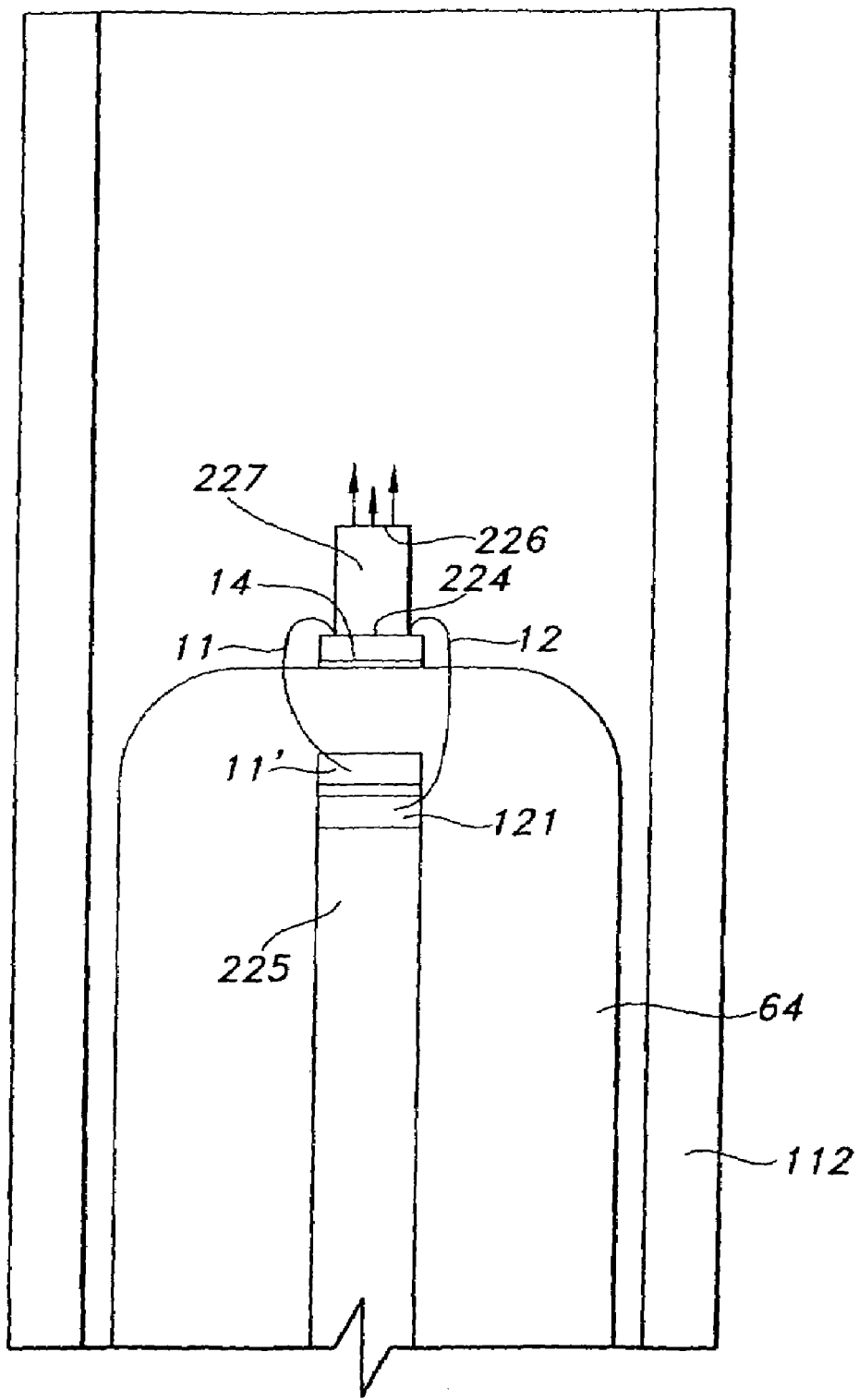
FIG. 16 shows a device where a vertical cavity surface emitting laser (VCSEL) is bonded to the heat pipe in an alternate embodiment of the present invention.

FIG. 16 shows the Vertical Cavity Surface Emitting Laser (VCSEL) embodiment of the instant invention. The drawing shows one VCSEL 224 bonded to the top (tip) of a heat pipe 64. It is understood that ways of VCSELs 224 instead of just one may be bonded to the ends of one or more heat pipes, It is further understood that the VCSELs 224 (or for that matter, edge emitting laser diodes) may be substituted for the LEDs 10 depicted in any drawing or stated in any embodiment in this patent application. The heat pipe 64 is shown within a sleeve 112. The heat pipe 64 and the sleeve 112 may be electrically isolated. Also the sleeve 112 and/or the heat pipe 64 may have a bend in them (0° to 90° or more). This may also be the case in any other heat pipe/sleeve combination shown in any embodiment in this patent application. Anode 11 wire and cathode 12 are shown running from a sub-mount 14 to a low impedance "strip-line" type current/voltage carrying device. This "strip-line" has two thin copper foil type tape anodes 11' and cathodes 12' running down the length of the heat pipe from the VCSEL to the power supply or pulser, The copper foil tapes 11' and 12' are insulated from each other as well as the heat pipe 64 and sleeve 112 (or other environment) preferably by Kapton type tape 225. The VCSEL 224 may be of the high power type (over 1 W) CW or much greater peak powers (over 1 KW). It may be pulsed with short (such as ps pulses) or long (such as ins pulses). The wavelength range may be from the UV to the IR. It may be used by the medical, military, manufacturing, or other industries. It may be used in a battery powered long, cylindrical (with fins) device, for target designation or range finding. It may also be used for telecom communication such as fiberless communications between buildings at eye safe (or other) wavelengths. It may be used indoors or outdoors. It may be used in a variety of medical applications. It is particularly well suited for a hand held device for PDT. The laser light emission with arrows pointed upward is shown emitting from a partially reflecting output coupler mirror 226. The active region and rear mirror are shown mounted to the conductive slug/submount 14. A transparent spacer assembly 227 is shown. Lenses 10a may be desirably employed.

Figure 17A:
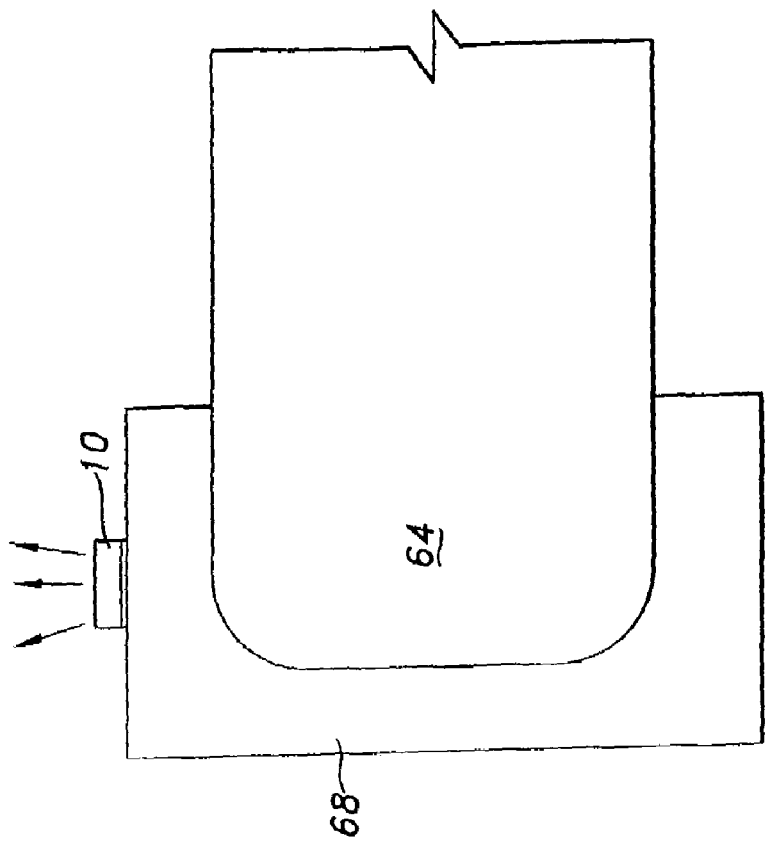
FIGS. 17 and 17a illustrate an exploded view of a heat sink bonded to the heat pipe according to a preferred embodiment of the present invention.
Figure 17:
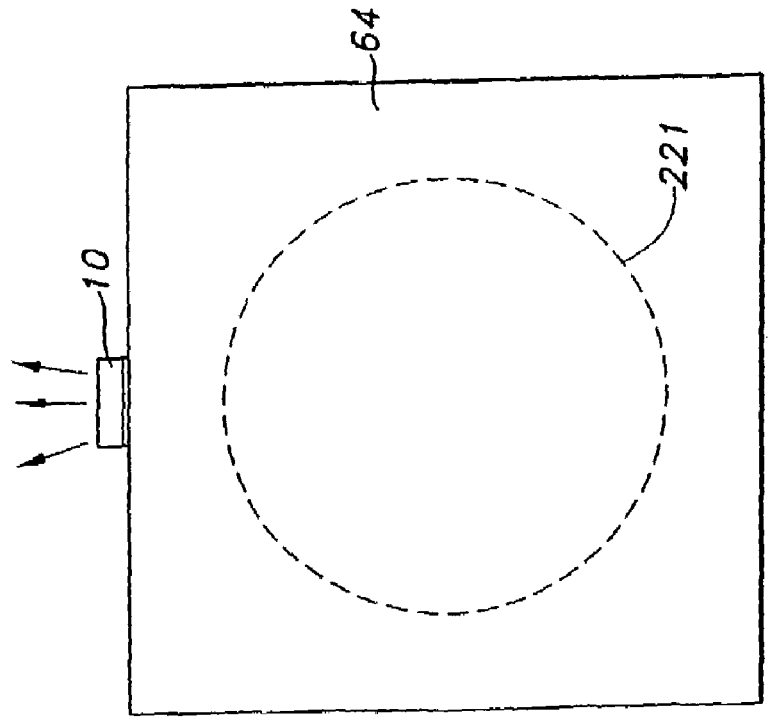

FIGS. 17 and 17a depict a separate heat sink 68 bonded to the end of heat pipe 64, it is understood that this heat sink 68 could be electrolytically electro-formed onto the end of the heat pipe 64. The electro-formed heat sink 68 could be made of copper. In the preferred embodiment the heat sink 68 is bonded to the end of the heat pipe 64 with high thermal conductivity glue. The LED 10 (or LEDs) is shown. The light emission from the LED 10 is shown as arrows pointed upward. This embodiment may also be useful for edge-emitting laser diodes. The dashed lines depict the blind hole 221 that is in the heat sink 68 to accommodate the heat pipe 64, FIGS. 18a and 18b shows an embodiment wherein the LED 10 is mounted to a flat side 64c or spot of the formerly cylindrical heat pipe 64. It is not necessary that the heat pipe be formerly cylindrical; it may be manufactured "flat". The light emission with arrows pointed upward is shown. Arrays (more than one) of LEDs 10 may be bonded to the flattened portion of the heat sink 68 in any orientation. The LEDs 10 may be soldered directly to the copper heat pipe 64 with lead/tin or other solder 110. This embodiment is preferable when a direct 90° side emission in relation to the heat pipe length axial direction is required. This is especially useful for curing applications that require close contact.

Figure 18D:
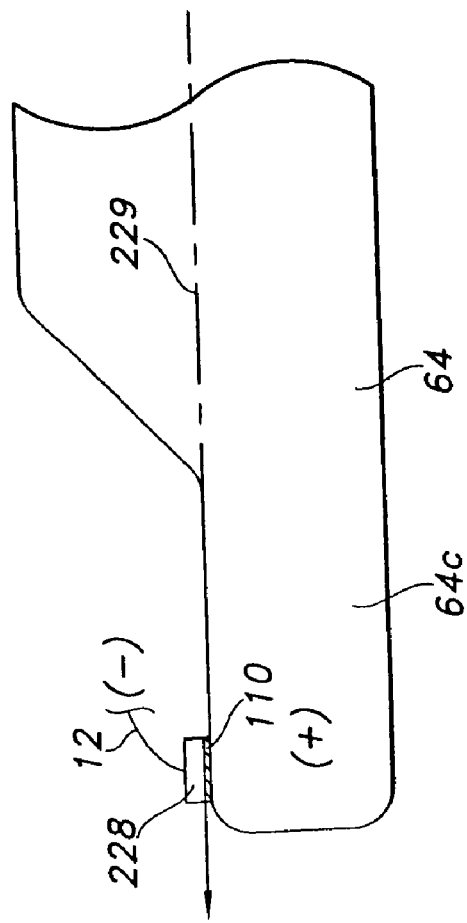
Figure 18C:
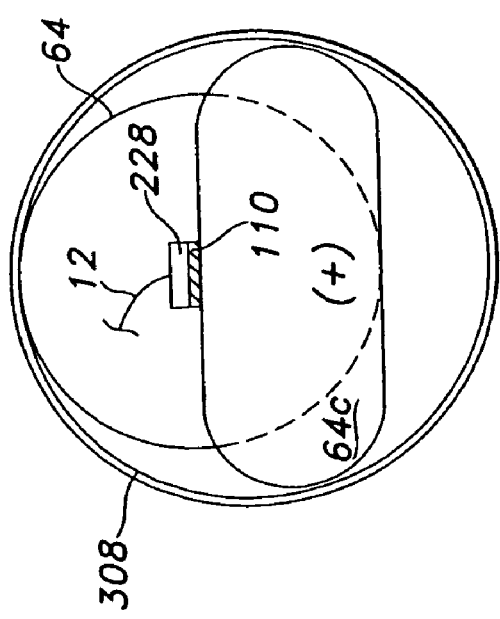

FIGS. 18c and 18d depict a laser diode 228 mounted directly to a flattened portion 64c of a round heat pipe 64. The negative anode wire 12 is shown along with symbol (−). The cathode in this drawing is the heat pipe 64, It is marked with symbol (+). Light emission with arrows pointed is shown. Also, solder 110 is shown. An edge emitting, broad area laser diode bar may be employed. Optional lenses may also preferably be employed. Lenses, such as diffractive optical elements (DOE) may also be desirably used in any embodiment to destroy the coherence of LDs. This makes them safer and easier to market from a regulatory (FDA) standpoint. FIG. 13c is a front view of the device. FIG. 18d is a side view of the device. Arrays of LDs, VCSELs, or LEDs, of individual chips or combinations of all three (in any combination) may be preferably used.

Figure 18E:
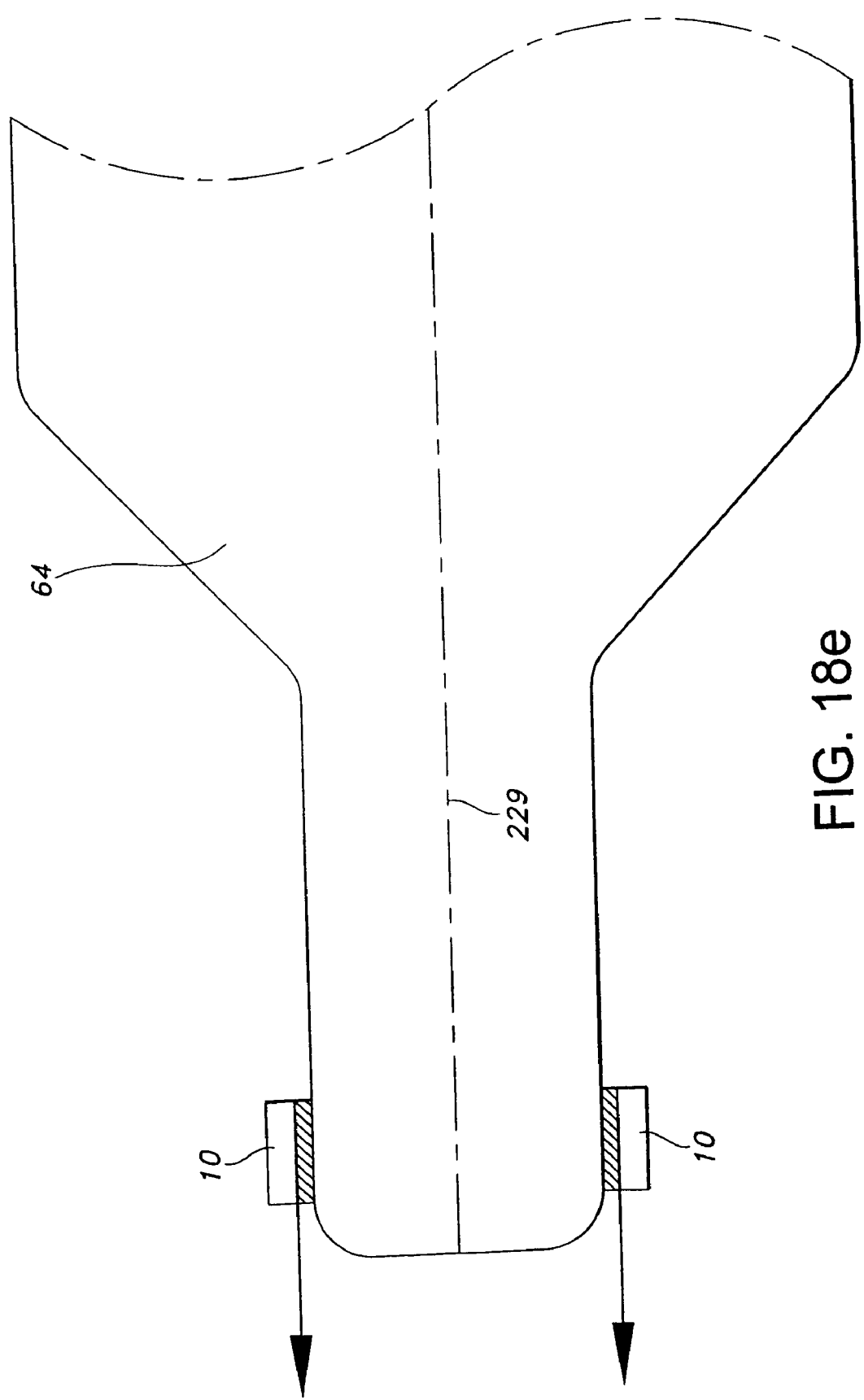

FIG. 18e shows a round heat pipe 64 that has been flattened at one end, with LEDs 10 disposed upon the flattened portion of the heat pipe 64. The center line 229 bisects the flattened portion through the center of the heat pipe 64. It should be noted that while this figure depicts a round heat pipe 64 that has been flattened only at one end, the present invention includes any round heat pipe 64 that has been flattened for any portion of its length so as to accommodate the reception of one or more LEDs 10. Additionally, the heat pipe does not have to have ever been round, as it may be manufactured flat. This is true for an embodiments in this patent application. It is noted that all embodiments in this application could utilize microchip or thin disk laser technology, For example, the active region of a microchip laser and/or gain media of a thin disk laser could be mounted on the tip of a heat pipe.

Additionally, in another embodiment of the present invention there is provided packaged LED (or laser diode) device(s) which provide superior thermal transfer which allows operating the LEDs at a current substantially higher than manufacturer specifications and in a package substantially smaller than the current state-of-the-art. The packaged LED (or laser diode) device preferably includes at least one LED, a sub-mount, a flex (or rigid) circuit, and an optional TIR reflector. This packaged device may be affixed to a heat pipe. The device may be used as a discrete device, or with an array of similar devices. Applications include entertainment, architectural, and specialty lighting, applications in medicine (PDT), displays and projectors, and applications in adhesive curing, as well as countless other applications.

Figure 19A:
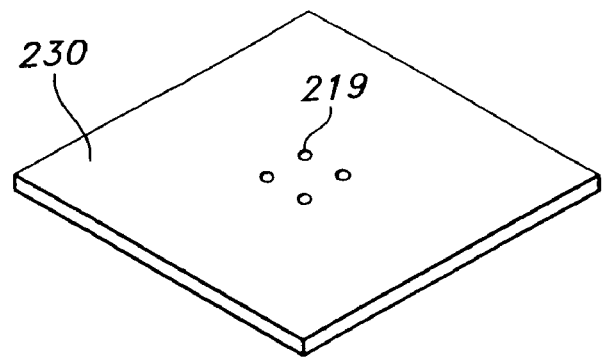
FIGS. 19a, 19b and 19c illustrate packaged LED device on a circuit board.

FIG. 19a depicts a high thermal conductivity material, preferably a CVD Diamonds for use as a heat spreader/submount 230. The diamond in this figure, preferably, is 100 microns thick and has 50 micron diameter laser drilled through holes 219. These holes 219 facilitate the transfer of a thermally, as well as electrically, conductive adhesive from top to bottom and/or bottom to top of the substrate. The holes 219 may have walls that are purposely sloped (not parallel) to allow for a bigger opening on one side than the other to facilitate easier filling of conductive adhesive. Other heat spreader/substrates, such as AlN or even copper, may be used. Heat spreaders may also be metalized with a pattern for one or more semiconductor die. The metalization may or may not extend through holes that may exist in the substrate. They may be metalized on one or both sides.

Figure 19B:
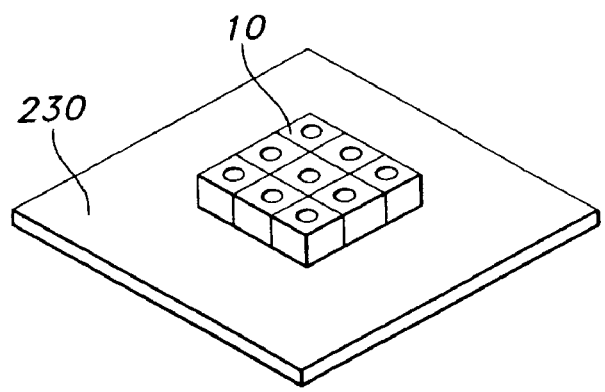
Figure 19C:
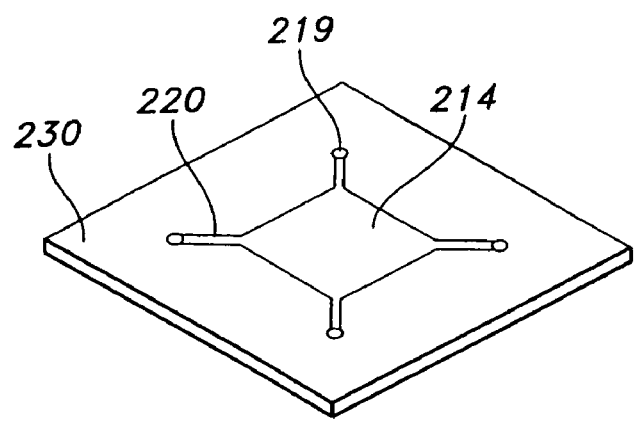
Figure 20:
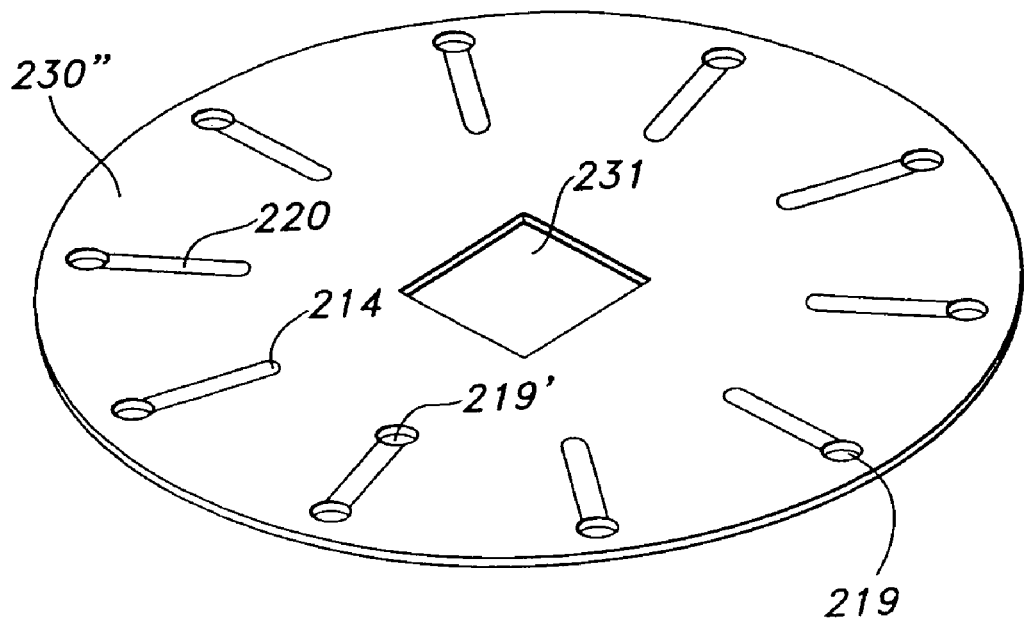
FIG. 20 shows a perspective view of the first circuit with a center cut out for bonding of LEDs together.

FIG. 19*b* depicts nine LED die 10 shoulder to shoulder on a heat spreader/submount 230. These die may be approximately 300 microns×300 microns at the top (wire bond surface) and approximately 200 microns×200 microns at the bottom "n" contact surface. These dimensions allow the holes 219 shown in FIG. 19*a* to not substantially fall under any die surface. The "streets" between the bottom of the dies encompass the holes 219. In other words, the holes in the heat spreader lie in the region between the bottom of the dies. It should be understood that one or both sides of the heat spreader may be metalized to accommodate a solder process and this metalization may extend through holes to allow conductivity from one side of the heat spreader to the other. Also this metalization may be built up by an electroplating or electroless process. Solder may be the metalization or perhaps gold in some instances. The preferable solder is 48 In/52 Sn as its melting point is 118° C. and this low temperature is easy on the polymer optic and also this solder is easy to fluxless solder using a fluorinated compound, such as xenonidifluoride during the reflow process. Conductive epoxy may be used to bond the dies 10 to the heat spreader/substrate 236. Another means of affixing may be to solder, provided that the substrate is first patterned and metalized. The holes 219 allow electrical current to flow between the top and bottom surface of the heat spreader/substrate 230. The heat spreader 230 is preferably non-conductive although it could be conductive if a metal such as copper or aluminum were employed. It is understood that only one die 10 may be used or multiple dies 10 may be used. They may be in series, parallel, or other combination and they may or may not be individually addressable. One or more centered wavelengths may be employed particularly if more than one die is used, although multiple wavelengths m exist on one die. In general, these wavelengths span the visible range from the UV/visible edge to out near the visible/IR edge. If multiple wavelengths are used, they may advantageously be employed to selectively target photo-initiators in adhesives or coatings, and may also be used to penetrate material to different depths. The devices may be capable of being remotely adjusted for beam angle, power, intensity, hue, color, etc. Usually, for most applications with multiple wavelengths, i.e. dies having different centered wavelengths, individual addressability is preferred. The devices in this application have this inherent individually addressable characteristic. The heat spreader 230 may preferably use only one die 10. The holes 219 through it should not be directly under the die(s) 10, but rather out from under it (them) in the periphery. Holes 219 could be replaced by wire bond pads in an alternative embodiment. Circuit traces 220 lead to the metalized bond pads(s) 214 in FIG. 19*c*. It should be understood that it IS NOT necessary to have holes 219 through the heat spreader 30. Circuit trace(s) 220 could simply lead to wire bond pad(s) 214 and a wire or wires could be bonded to the pad(s) and terminate at another bond pad as shown in FIG. 20 to facilitate completion of an electrical circuit. This bond pad 214 could also take the place of through hole 219' in FIG. 20 for example.

FIG. 20 shows layer 230" which is a flexible or rigid circuit material with a cut-out 231 through the center which allows the LED die(s) 10 to come through from the layer 230". The flexible or rigid circuit material may also be referred to as just the circuit material and it may be of any preferably polymeric material but is most preferably a polyimide. Other possible layer materials are CV Diamond, AlN, BeO, silicone, etc. When it is very thin and flexible, such as being less than 0.005", it is most preferably trade name Kapton from Dupont (DE, USA). When it is less flexible to even rigid, such as around 0.040", the material is a polyimide trade name Cirelex from the Fralock Co. (Torrance, Calif., USA). It has wire bond pads 214 and circuit traces 220 that extend out to the preferred plated through holes 219. Each bond pad 214 may accept a wire from an LED. One trace does not have a bond pad, but rather a larger plated through hole 219'. This through hole 219' optionally allows the same electrically conductive glue under the heat spreader 230 to come through and contact the trace 220 connected to it. This essentially allows the electrical polarity of the adhesive under the heat spreader 230 that goes up through the holes 219 in the heat spreader 230 and contacts the adhesive under the die(s) 10, to be the same polarity. In the preferred embodiment, this polarity is "negative" (although it could be "positive") and allows multiple die to share a common ground plane. This ground plane can then have an electrically continuous path up through the through hole 2191 to a trace 220. Note that optional through hole 219' may preferably act as the electrically continuous path that is on top and in the same plane as the die(s). The preferably flex circuit 230" in this figure is preferably of Kapton or similar, substantially non-conductive material with gold plated copper traces that are patterned, etched, and (subsequently gold, or other) plated. This circuit 230" is available on a custom designed basis from manufacturers. The cut-out 231 in the center may be sized to just clear the die(s) 10 or it may be larger. It may also facilitate conductive adhesive stenciling. It is bonded to the preferably flex (or rigid) circuit material 230' as will be shown in FIG. 20*b* through the use of a B-stageable adhesive layer. Again, it is understood that the plated through hole 2191 could be negated by replacing it with a bond pad 214. A wire 213 could then be bonded to this bond pad 214 and a bond pad or pads on the heat spreader 230 that lead, for example, to a ground plane.

Figure 20A:
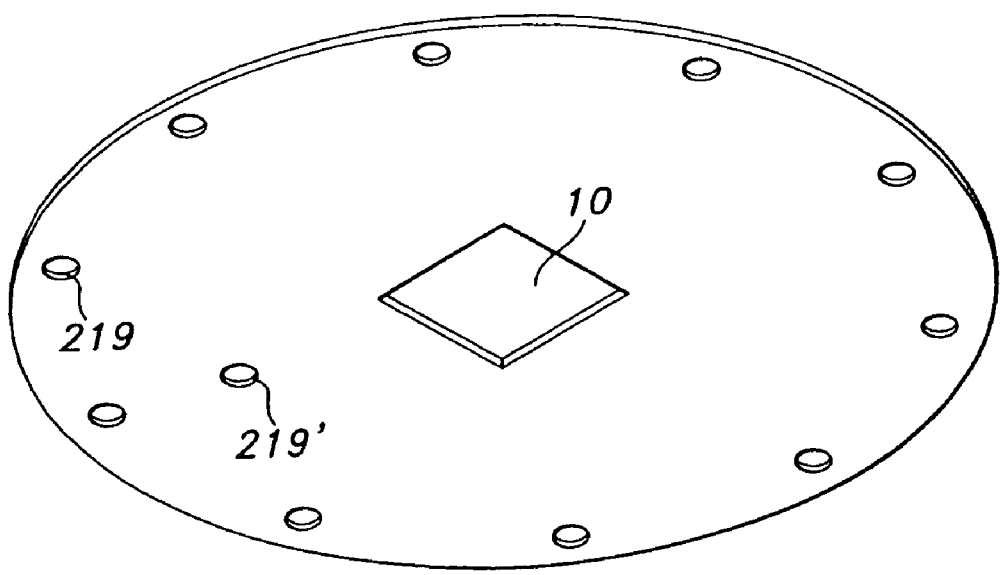
FIG. 20a shows a bottom view of the circuit of FIG. 20.

FIG. 20*a* depicts the "bottom view" of FIG. 20. The holes 219 and 219' are preferably plated through (i.e. the walls of the holes, not including the center die cut-out, are electric conductive). This is often accomplished through the use of a palladium emersion coating applied during the manufacture of the flex (or rigid) circuit.

Figure 20B:
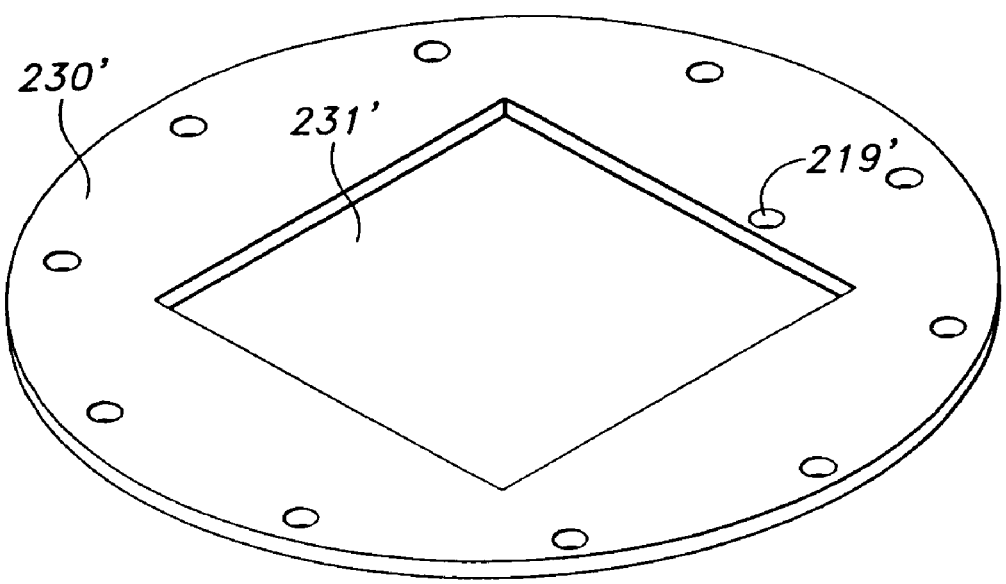
FIG. 20b shows a perspective of a second circuit with a center cut out.

FIG. 20*b* shows the thicker circuit material 230' and shows the top side. Note the cut-out 23. Preferably by laser means through the material preferably Kapton or rigid FR4 Flex that allows the heat spreader 230 of FIG. 19 to fit inside. The circuit material 230' may also preferably be about the same thickness as the heat spreader 230, i.e. approximately 75 to 150 microns. This circuit material 231' with this side shown is bonded to the bottom of layer 230" of FIG. 20.

Figure 20C:
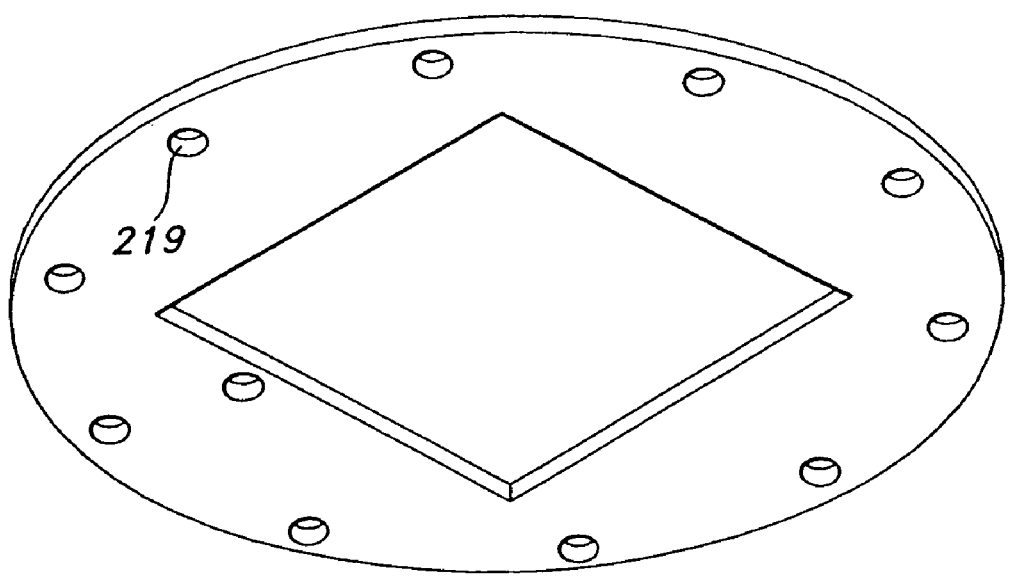
FIG. 20c shows a bottom side of the circuit of FIG. 20b.

FIG. 20*c* shows the bottom side of the material 230' of FIG. 20*b*. Note that the round through holes 219 are preferably plated through.

Figure 20D:
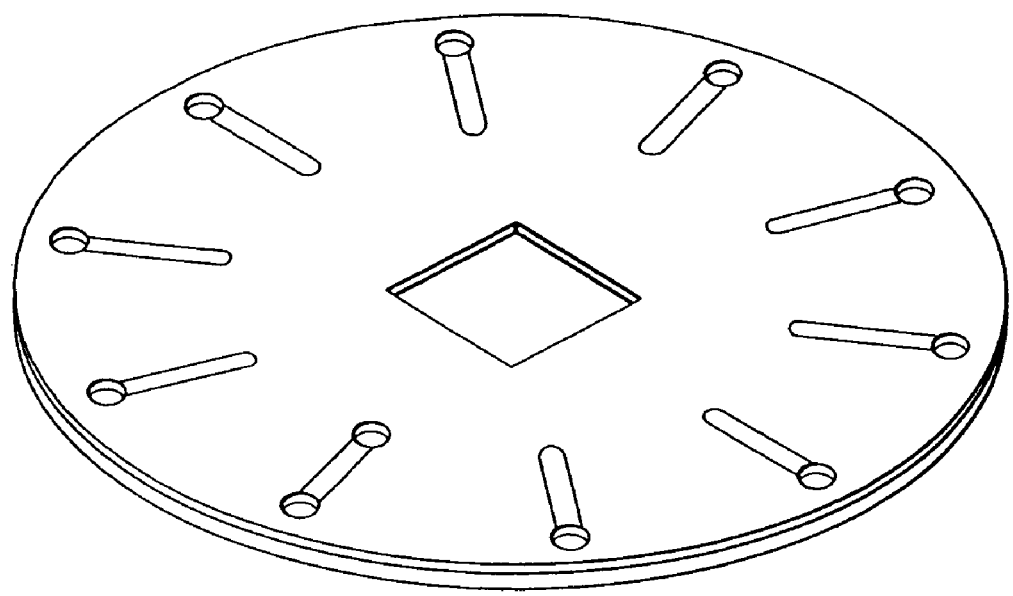
FIG. 20d shows the first circuit of FIG. 20 and the second circuit of FIG. 20b bonded.

FIG. 20*d* shows the circuit material 230" of FIGS. 20 and 20*a* bonded to the material 230' of FIGS. 20*b* and 20*c*.

Figure 20E:
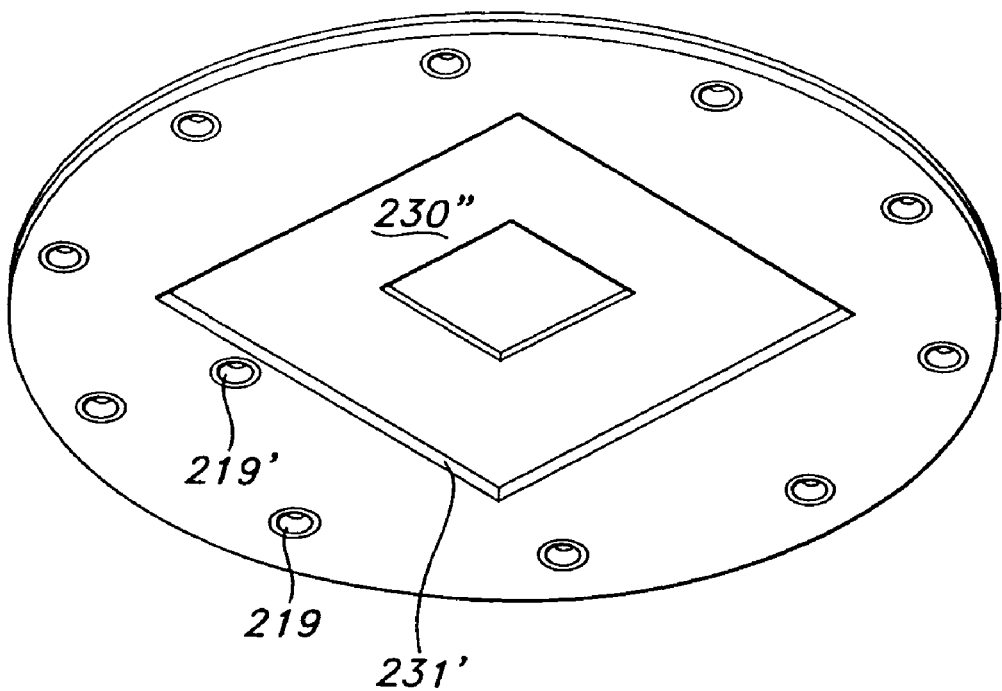
FIG. 20e shows the bottom side of the two bonded circuit of FIG. 20d.

FIG. 20*e* shows the bottom side of the two bonded materials depicted in FIG. 20*d*. Note how the cut-out 231' is terminated by the "membrane" like top circuit material 230". This cut-out accepts the dimensions of the heat sink 68. In fact, the heat sink 68 is glued into place by placing a drop of glue in the four corners of this cut-out 231' and then the heat spreader material 230 is gently placed within the confines of the cut-out 231'. Note that you can clearly see the optionally plated through holes 219 and 219'.

Figure 21:
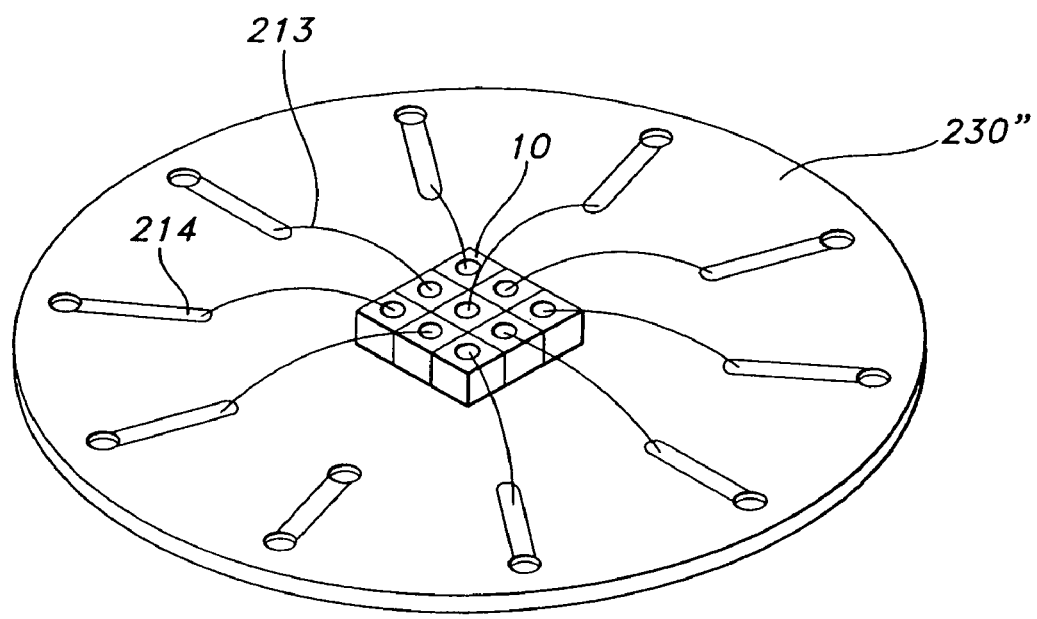
FIG. 21 illustrates a perspective view of the first circuit of FIG. 20 with multiple LEDs.

FIG. 21 shows the previously described circuit material 230" with nine LED dies 10 bonded to it with an electrically and thermally conductive means. The nine dies are for example only. One or more dies may be used. In this example, they are marked "p" side up, although "p" side down with individually addressable bond pads 214 may be employed.

Each die 10 (or packaged die) may be controlled by a computer controlled resistive element between the die cathode lead 12 and a power supply, useful when the, LED 10 is mounted "p" side down on a heat sink 68 that may have an electrically conductive common anode. If the "p" side is not on a common anode (each LED "p" side is electrically isolated from the rest) the current may be directly modulated between the power supply and the "p" contact. Pulse-width modulation may preferably be employed. If the chips are mounted "p" side up, they could share a common cathode and desirably be modulated individually by a computer controlled current modulator between the "p" contact and the power supply. The traces to the bond pads 214 in FIG. 21 could be etched and/or buried in a silicon or other semiconductor layer that could be on top of a high thermal conductivity material such as diamond or traces 220 could be copper on top of flax or rigid circuit 230". Wires 213 are shown from the top of the LEDs to bond pads 214. The LEDs 10 may preferably be placed in the proper position using automated pick and place equipment with machine vision capabilities.

Figure 22:
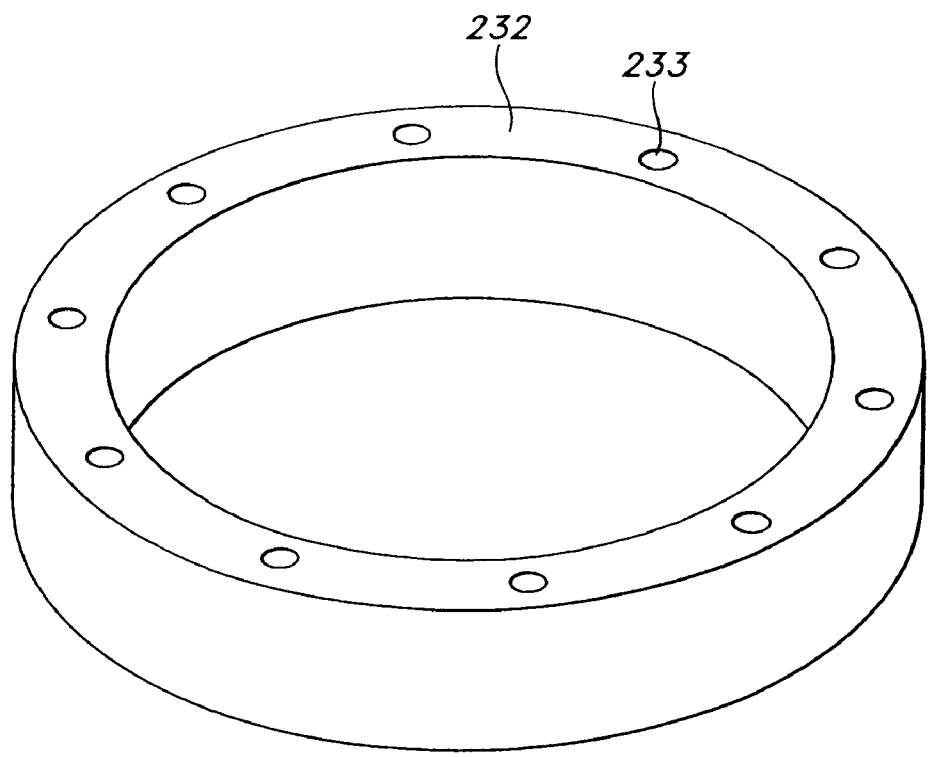
FIGS. 22 and 22a show a ring assembled on top of the first circuit of FIG. 20.

FIG. 22 shows a ring 232 that sits on top of the circuit material 230" of FIG. 20. It is a strengthening member first, but it can also be used as a current equalizing member between all the traces 220 if it has some electrical conductivity. It may also serve as a pin guiding member. This conductivity may result from it being a metal or coated with a metal. Furthermore, the conductivity between it and the traces 220 and/or the plated through holes 219 may be established through the use of an electrically conductive adhesive or solder. The through holes 233 of the ring 232 are aligned over the through holes 219 of the circuit material 230" and adhesive may be injected in them and/or they may contain pins that come up through the plated holes 219 that facilitate electrical interconnections which will be explained later in detail. The ring 232 could also preferably be non-conductive.

Figure 22A:
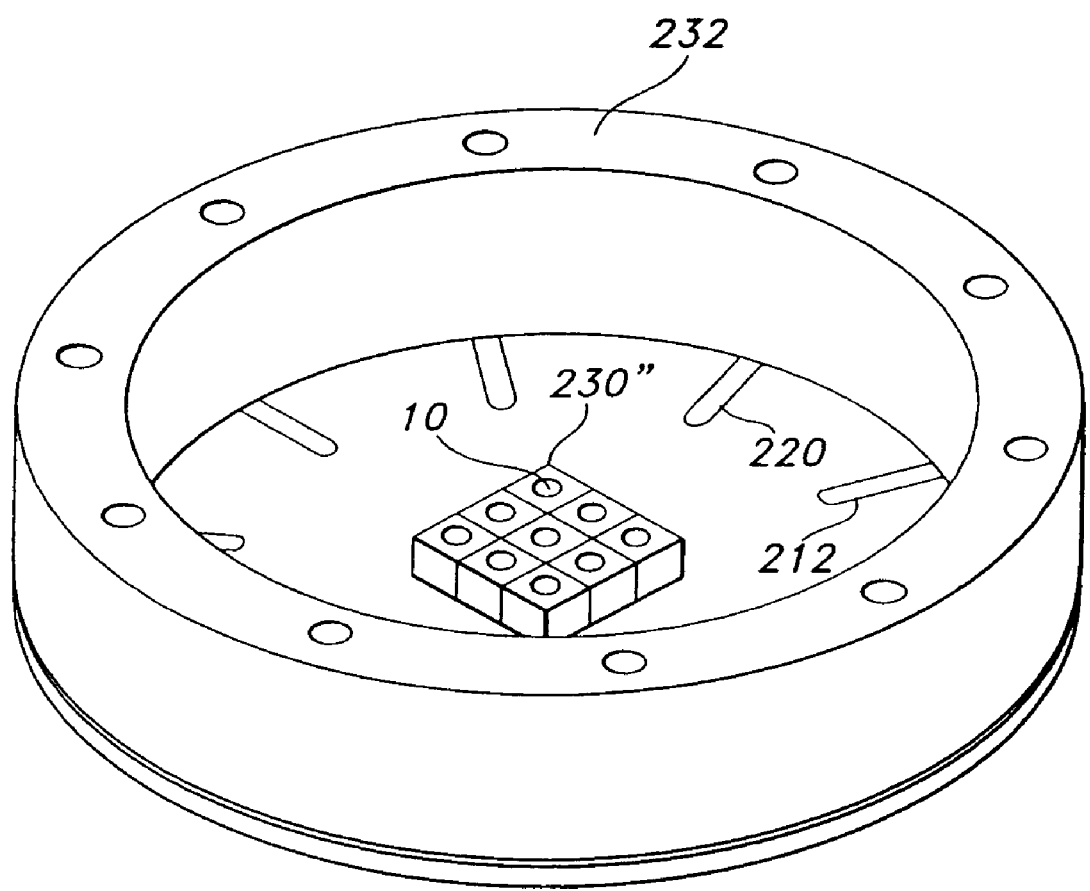

FIG. 22*a* shows the ring 232 of FIG. 22 affixed to the top of circuit 230. Circuit traces 220 and wire bond pads 212 are shown. It is understood that circuit traces 220 and pads 212 could be a monolithic circular annular ring around the outer periphery of circuit 230" if all of the LEDs 10 (or a single LED) were electrically driven together in parallel and were not individually addressable. The ring 232 could be connected to an outer sleeve by conductive adhesive to facilitate electrical connection. The adhesive could be applied to both parts through a hole in the sleeve.

Figure 22B:
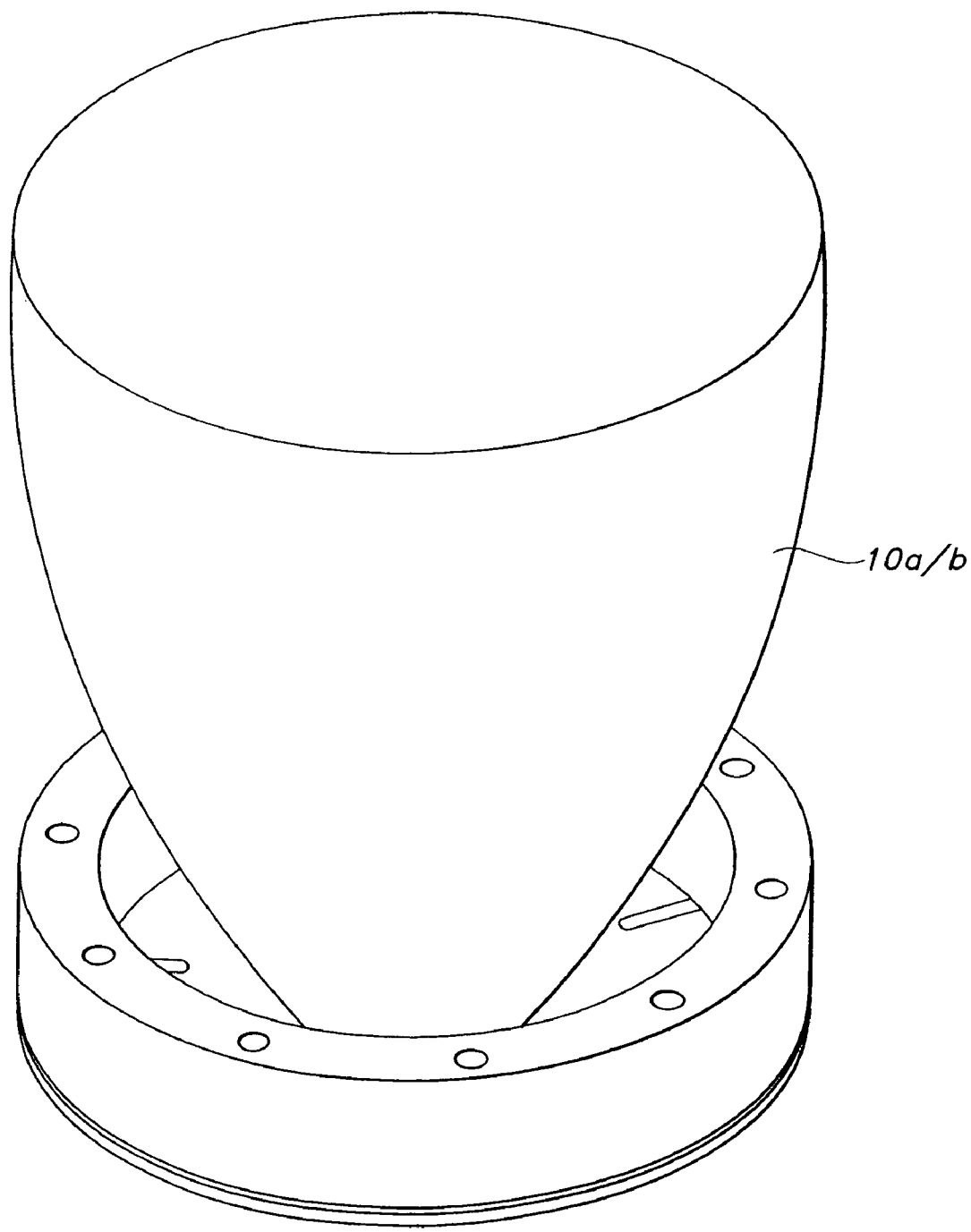
FIG. 22b illustrates the assembly of FIG. 22a with a TIR lens/reflector.

FIG. 22*b* depicts the assembly of FIG. 22*a* with a TIR lens/reflector 10*a/b* over the LED(s) 10. It has a hemispherical cavity in the bottom of it (not shown) that is filled with a preferably heat curable index matching compound. This compound (or gel) allows greater light extraction from the LED die due to its index matching properties. It may be placed on the hemisphere and allowed to partially cure. This partial cure increases its viscosity. The LED(s) may be lowered into the gel in a chamber that is of a pressure lower than ambient. It may also be allowed to fully or partially cured at this sub-ambient pressure. This procedure can lower the risk of a bubble formation. It is important that TM lens/reflector 10*a/b* be lowered over the LEDs at a rate of around 1 micron/second or less. Again, the hemispherical cavity does not have to have a spherical shape. Lens/reflector 10*a/b* could have metalized walls. It also could preferably have an annular "stop" at its point of smallest circumference to act as an index matching compound reservoir.

Figure 22C:
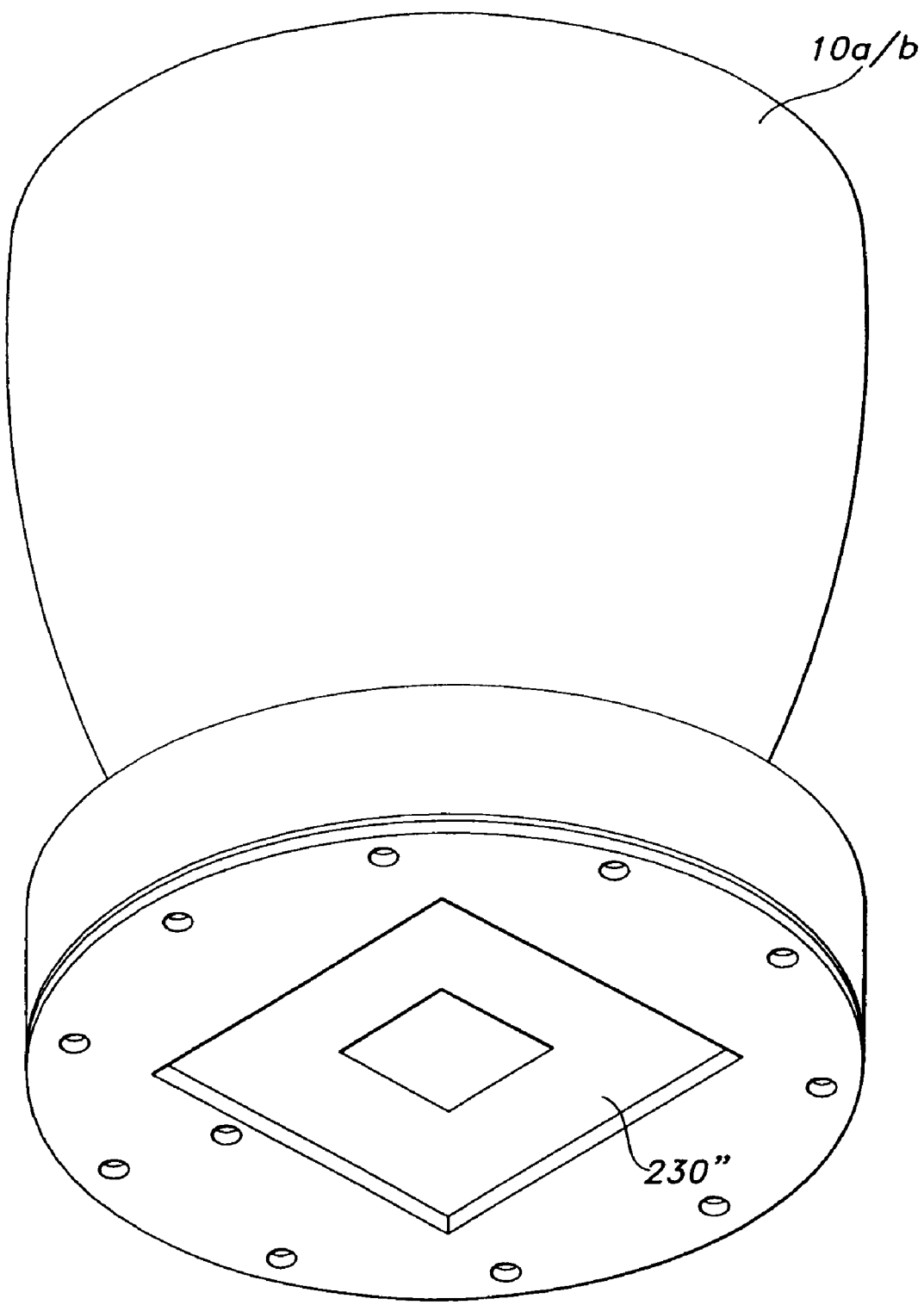
FIG. 22c illustrates a bottom view of the assembly of FIG. 22b.

FIG. 22*c* shows a bottom view of the assembly of FIG. 22*b*, but for purposes of explanation the heat spreader 230 with the attached LED(s) 10 is shown removed from the assembly. Shown herein is the circuit layer 230" and the reflector 10*a/b* is shown for purposes of orientation.

Figure 22D:
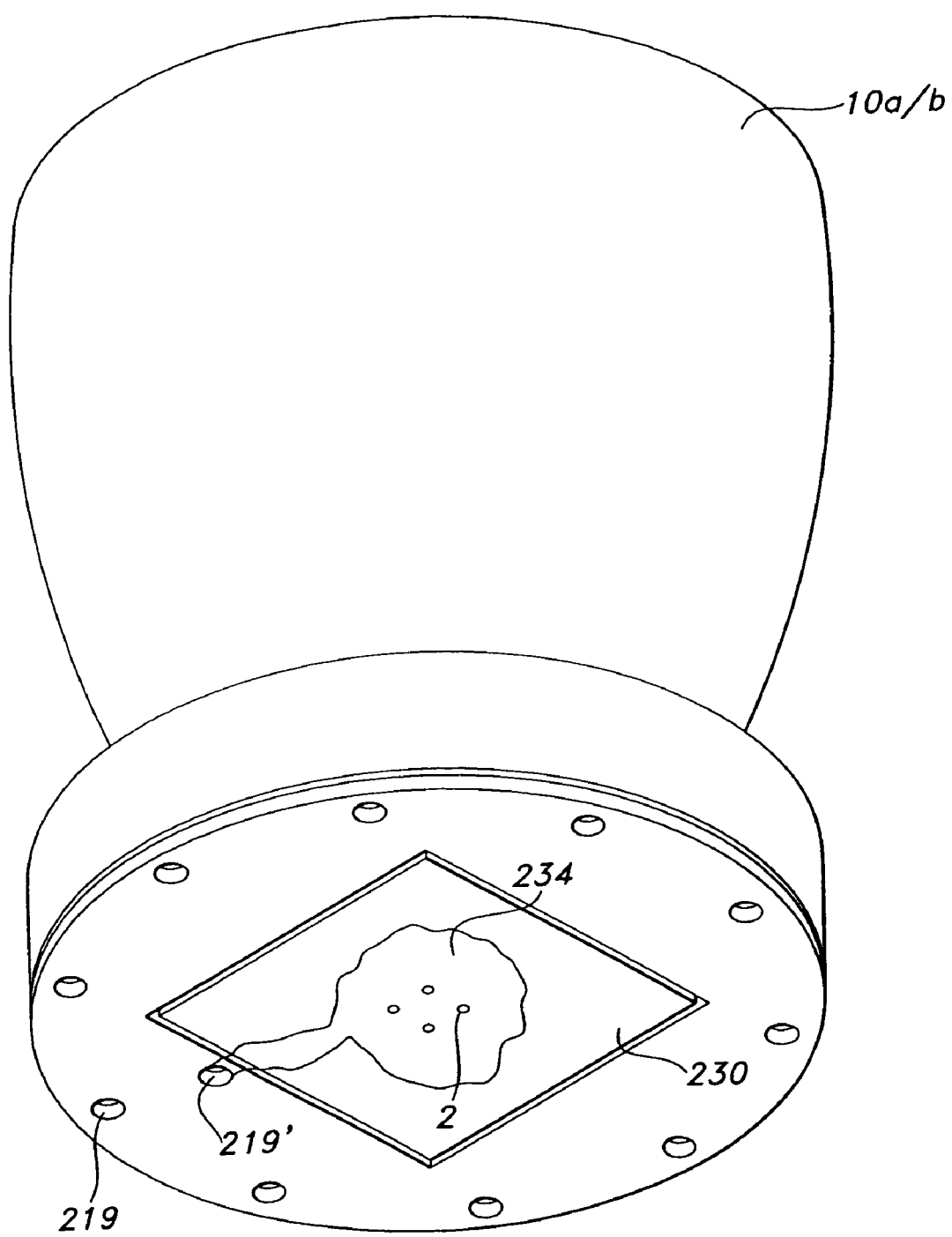
FIG. 22d shows a perspective view of the assembly of FIG. 22c with the first circuit.

FIG. 22*d* shows the assembly of FIG. 22*c* with the heat spreader 230 shown. Uncured conductive adhesive 234 is shown smeared on the bottom of heat spreader 230. It is applied in such a fashion as to make sure that adhesive goes up the through hole 219' to the LED die 10 (not shown) and also, if desired or applicable, over to hole 219' and LIP it. Again, this is the case if one is trying to facilitate an electrically continuous path from the bottom of the assembly or heat spreader 230 (or heat sink 68, or slug 14) to the top surface of the heat spreader 230 in the same plane as the LEDs. It is noted that adhesive 234 can be spread on top of heat pipe 64 prior to the assembly of FIG. 22*d* affixed on the heat pipe 64. It is understood that the assembly of FIG. 22*c* does not need to be mounted on a heat pipe 64 (not shown). It is quite acceptable to mount this assembly on a circuit board and use the heat spreader 230 to spread heat and lower thermal resistance. If not mounted on a heat pipe 64, the assembly may become a SMT (surface mount technology) device. When mounted to a circuit board, traces on the board could lead to plated through hole 219' (which could be plated solidly through) and could serve the purpose of either an anodic or cathodic contact providing that another through hole similar to 219' but on the opposite side of spreader 230 with opposite polarity (as well as, obviously, opposite functionality is provided. In this description the heat spreader 230 could have holes in it providing that they are used as a polar contact and did not short out the previously described circuit. It is preferable that solder 110 be used in this particular embodiment as adhesive can wander short out the device. In this, case adhesive blob 234 would not be present. The solder 115 may be applied to the proper places on the assembly or to proper pad(s) 214 on a circuit board 216 not shown.

Figure 22E:
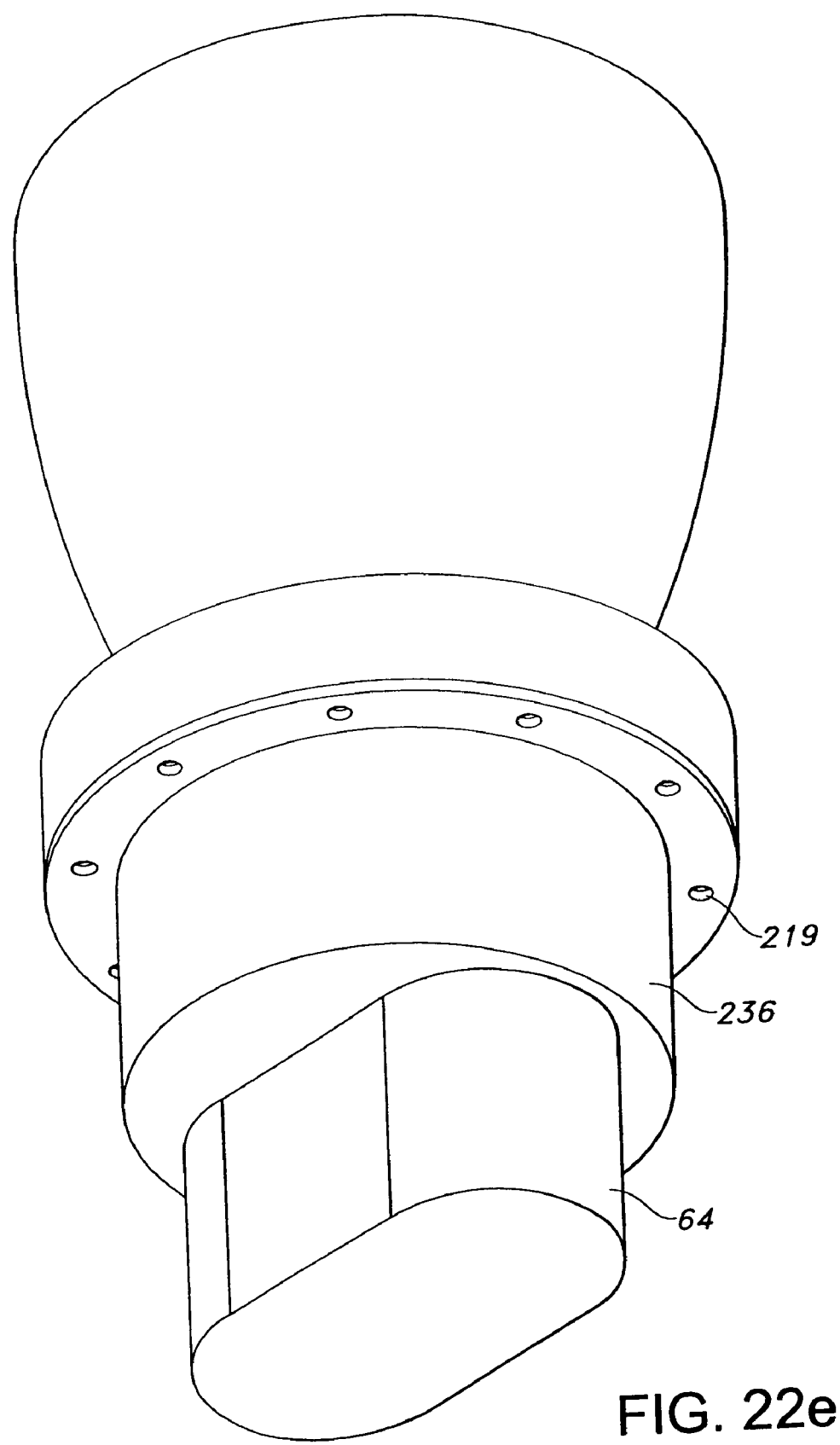
FIG. 22e shows a perspective view of the assembly of FIG. 22d with a strengthening ring and the heat pipe

FIG. 22*e* depicts the assembly of FIG. 22*d* with a strengthening ring 236 and a heat pipe 64 shown. The heat pipe 64 shown is a flattened (although it can be round) and, for example only, has an oval dimension of 2 mm×33 mm×200 mm in length. The strengthening ring 236 may also be thermally conductive so as to spread some heat from the LEDs 10 to the side walls of the heat pipe 64. This may lessen the chance of "dry-out" as the heat is spread over a larger surface of the heat pipe 64. The assembly of FIG. 22*d* is affixed to the plane dictated by the top (tip or end) of the heat pipe 64 and the ring 236 that surrounds it. A thermally and electrically conductive glue may be used for the affixation. The finished assembly may be placed in a female receptacle in a circuit board (not shown) wherein conductive "bumps" or pins could make contact with the plated through holes 219. These "bumps" could be attached to circuit traces 220 in or on the board 216, that could then turn on and off the current to the desired plated through holes which would then result in selected (or all) LEDs turning on or off (or some level in between) at the selected level(s), intervals, and intensities. The "bumps" may be placed on the hole(s) 219 or on a circuit board 230 (not shown) or both as will be shown and described in greater detail in FIG. 24 and FIG. 25 below. The solder bumps may be applied to either the circuit board or the assembly of FIG. 22*d* using robotic solder bumping equipment available from PacTech (San Jose, Calif.). During circuit board manufacture, particularly during plating and etch operations, a solder mask-type material may be used to "tent" over the ID of the strengthening ring to protect the circuitry on the circuit material.

Figure 22F:
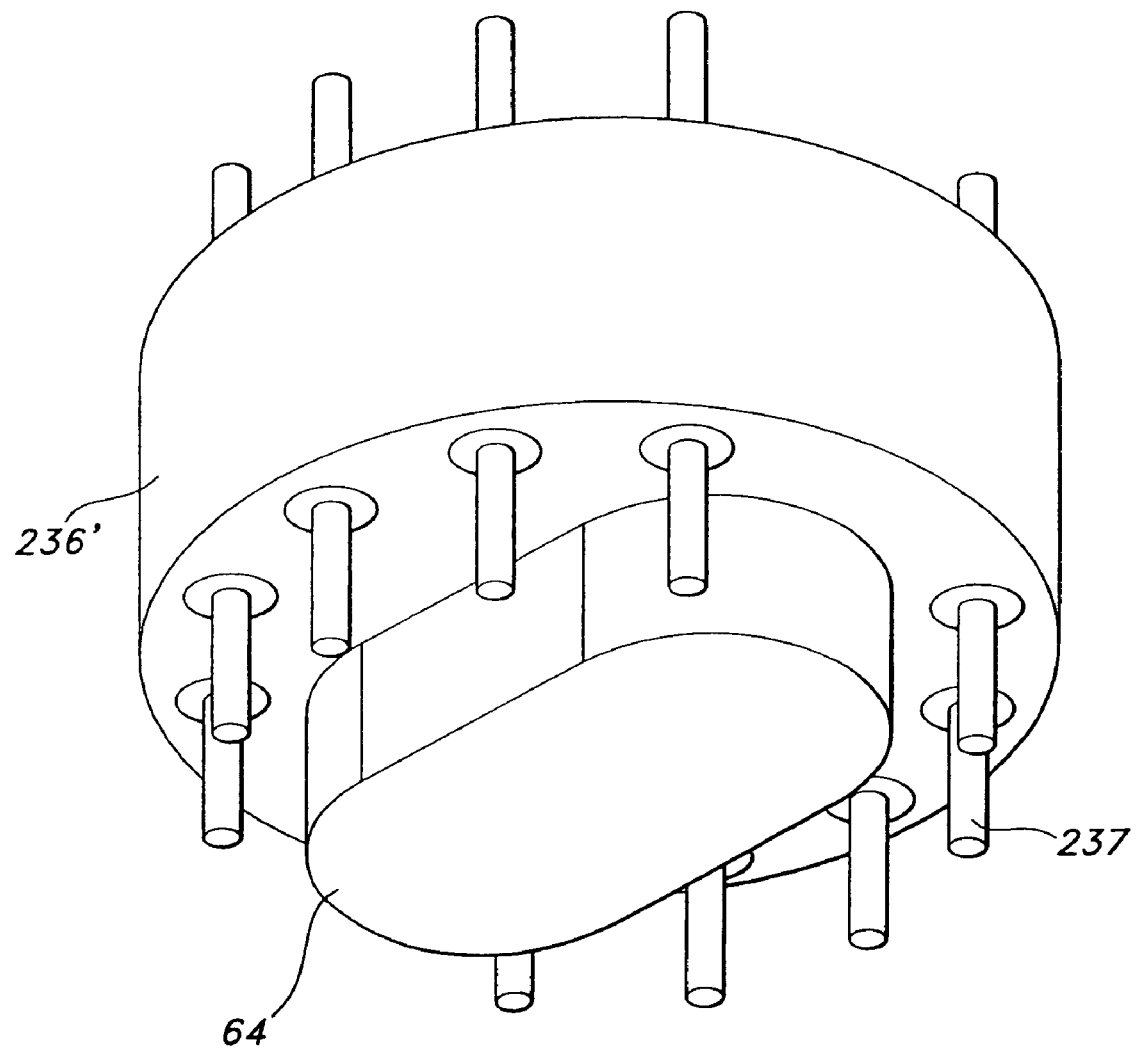
FIG. 22f shows a bottom view of the assembly of FIG. 22e illustrating alternate electrical connections.

FIG. 22*f* depicts the bottom view of an alternative electrical interconnection scheme to that described in FIG. 22*e*. This scheme uses conductive pins 237, similar to nano connectors, to complete the conduction path from the LED, through the wire, through the trace, through the plated through hole, into the conductive pill(s) 237, and the pill(s) 237 into a mating female sleeve or plated through hole located in a circuit board that has appropriate circuit traces to the female alcoves and to a controller and power supply. The assembly in this drawing has a different style strengthening ring 236' than the strengthening ring 236' of FIG. 22e. Heat pipe 64 is shown, but as in all drawings, has only a portion of its length depicted for clarity. The pill(s) 237 could alternatively be placed in a circuit board and female receptacles or plated through holes in ring 236' and/or hole(s) 219 of FIG. 20.

Note how the pins(s) 237 protrude from both the top and bottom of ring 236. The portion of the pins can go into the holes in ring 232 of FIG. 22 and the bottom portion slide into appropriate female receptacles in a circuit board as will be shown and described in detail in FIG. 23. The circuit board may have an array of complete LED assemblies whose LEDs are individually addressable. These arrays may be used for full motion, large video displays, for medical applications (like wound healing), and for curing glues inks, or coatings. The ways used for curing or other photo initiated chemical reactions may have multiple wavelengths strategically turned on at proper times at strategic wavelengths and intensities. The arrays in large video screens or light fixtures could be activated and controlled remotely using wi-fi or blue tooth or other wireless means and protocols. This would greatly reduce the demands of muting traces to all devices oil a large and densely packed circuit board.

Figure 22G:
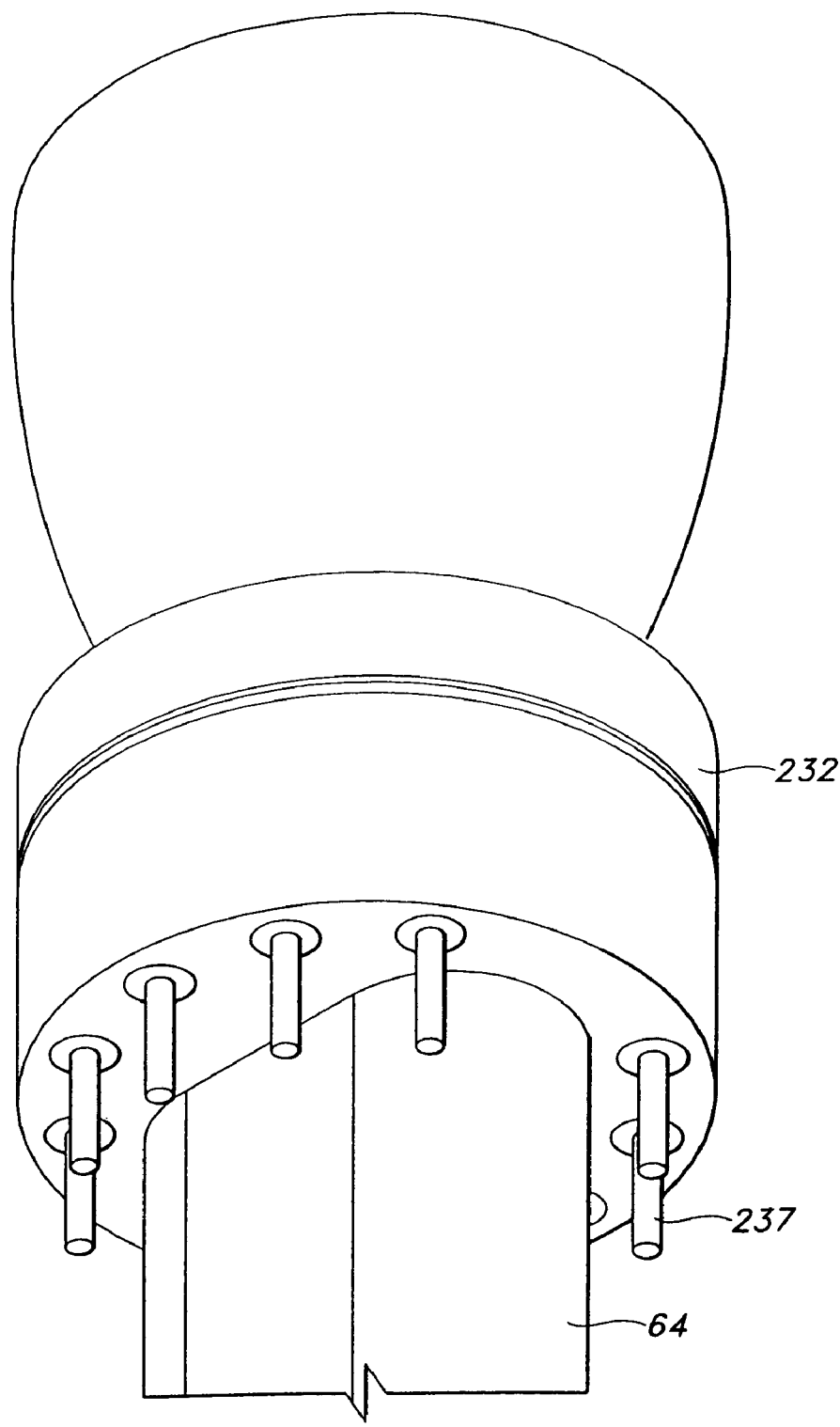
FIG. 22g illustrates a complete assembly with the assembly of FIG. 22d affixed to the assembly of FIG. 22f.

FIG. 22g shows a complete assembly with the assembly of FIG. 22d affixed to the assembly of FIG. 22f. The pin(s) 237 may be glued into the holes of ring 232 (not shown) as well as the preferably plated through holes 219 (not shown). One, or possibly more, pills, may be used as a ground (cathode). If a pin or pins are used, they may be glued with electrically conductive adhesive 234 or solder 110 into hole(s) 219 that has a trace leading to hole(s) 219' as shown in FIG. 20. This may facilitate the negative (cathode) connection of the assembly. There are preferably many different embodiments possible for facilitating a ground connection. The ground connection may take place on the same plane as the bottom of the LED(s), on the bottom of the heat spreader, a combination of each, or some other possibility that one skilled in the art could conceive. The heat pipe may have a bump on its outer surface to key into an opposite-shaped receptacle in a circuit board for purposes of orienting the pins and their polarity.

Figure 22H:
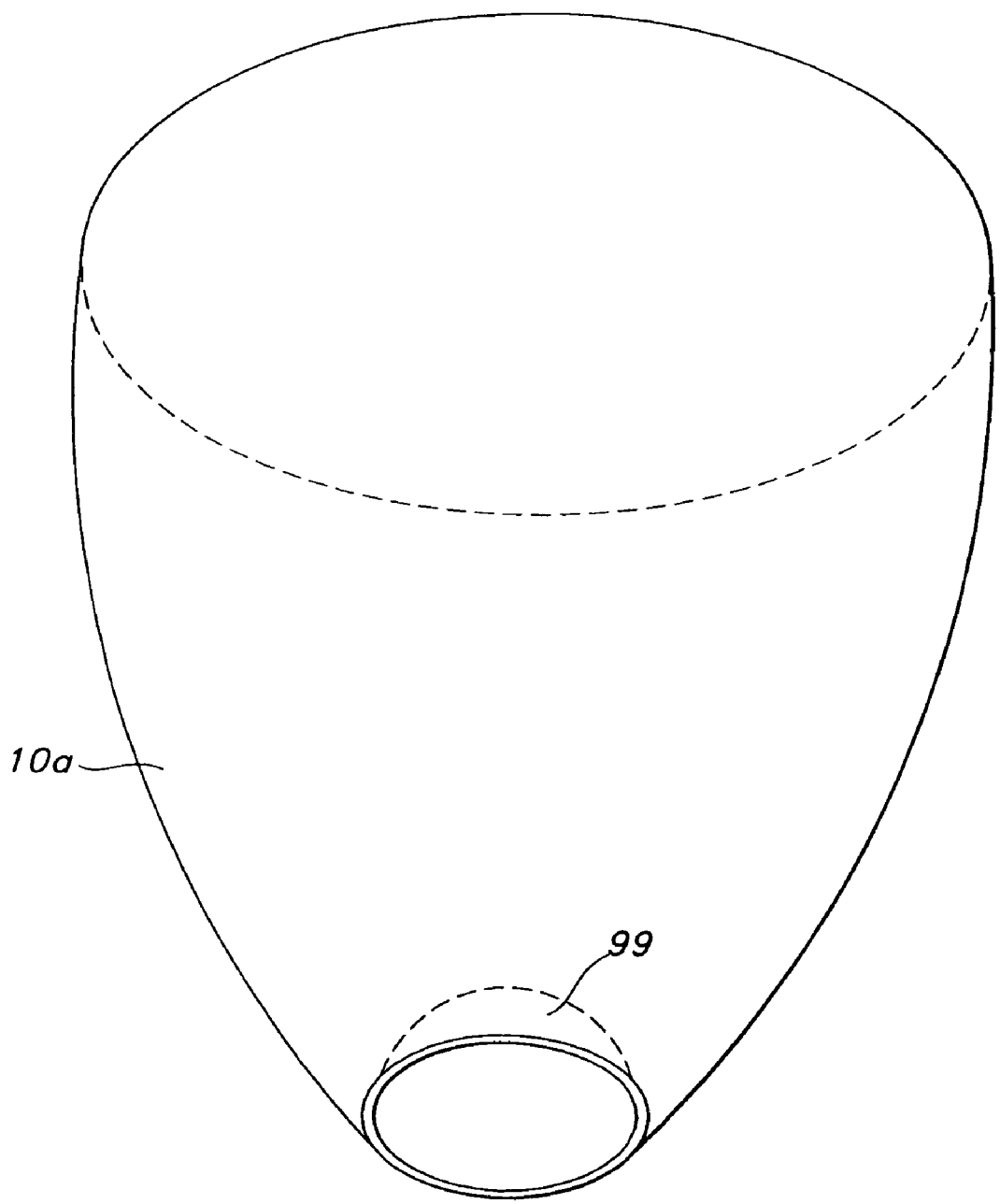
FIG. 22h shows an exploded view of the lens of the LED including a concavity according to a preferred embodiment of the present invention.

FIG. 22h depicts one aspect of the present invention, a total internal reflecting (TIR) lens 10a that includes a concavity 99 at die end of the lens 10a within which an LED 10 is to be disposed, Note that the concavity 99 could be filled with an index-matching gel to surround and encapsulate the LEDs disposed within the cavity of the lens 10a. The TIR reflector 10a depicted in this figure may be molded of, for example, Zeonex E48R and it may be produced by a micron-tolerance-capable injection-molding machine. The index-matching gel that surrounds and encapsulates the LEDs 10 has a refractive index between the refractive index of the LED substrate and/or epitaxial layers and that of air, and preferably has a refractive index greater than 1.59, although other indexes may be used. The concavity 99 may have a mushroom shape to provide uniform illuminance. Instead of a mushroom shape a diffractive surface could be used to provide uniform illuminance a spacer could be employed between the TIR optic 10a and the heat spreader if the LED die with an epitaxial structure on top of the die is employed. This is opposed to no spacer layer needed when the die is placed epitaxial-layer down, otherwise known as a "flip chip". The LED die may be completely immersed in the encapsulating gel that is provided in to the ton cavity. The optical axis is along the length of the optic whereby the optic is rotationally symmetric about the optical axis. The optical axis can also be called the cone axis.

Figure 23A:
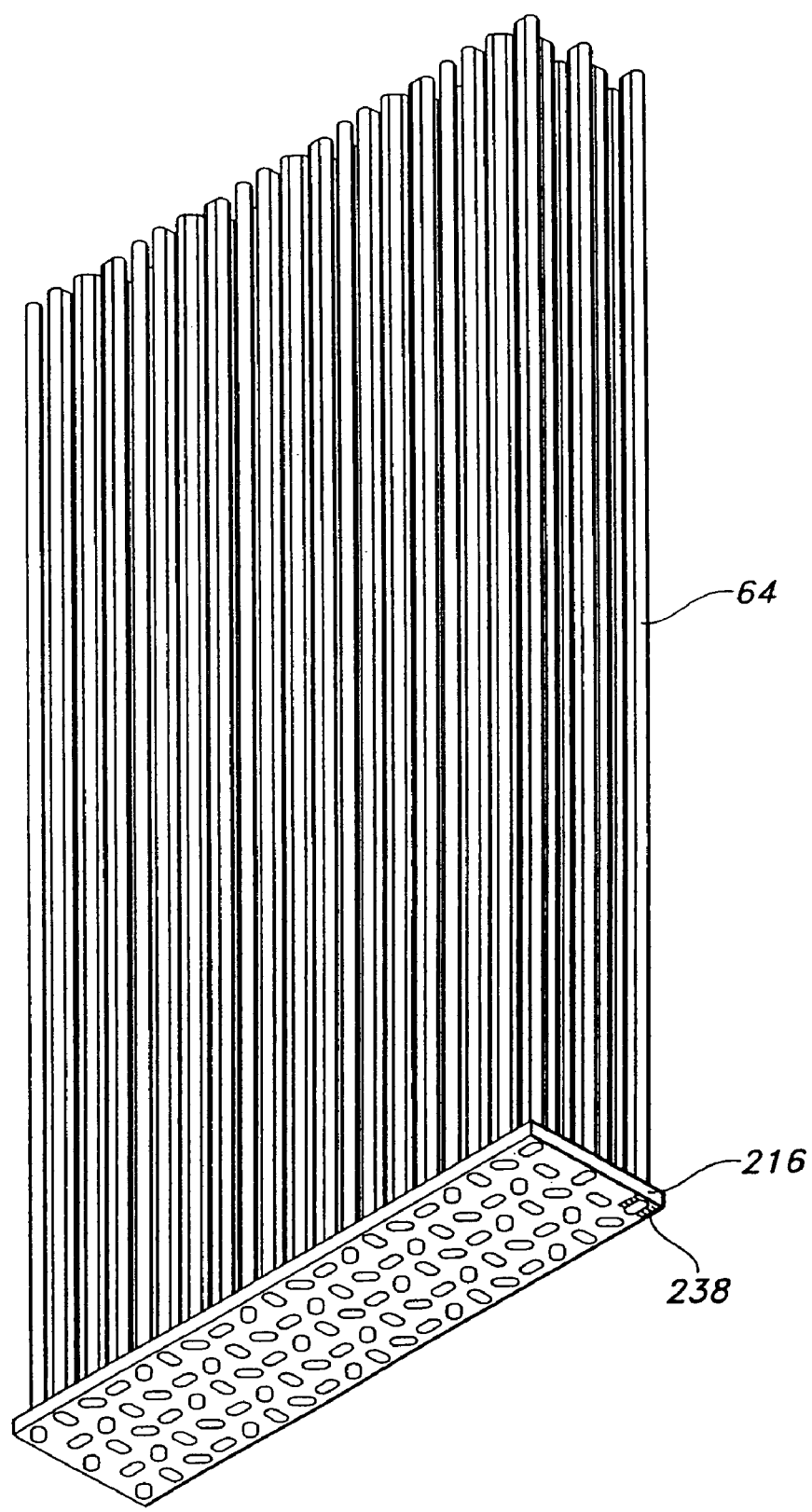
FIGS. 23a and 23b show an array of heat pipes inserted into the circuit board.

FIG. 23a shows an array of heat pipes 64 inserted into circuit board 218. Preferably, the length of the heat pipes 64 are 200 mm and the dimensions of the board 218 are 25 mm×100 mm stacked. These dimensions would allow two 100 mm×100 mm stacked falls 66 to blow air though the array of heat pipes 64 in a dimensionally compact and space conserving manner. Note that by using oval (flattened) heat pipes, air flow between the heat pipes is torturous which results in turbulence, which increases heat transfer. Also note that the oval shape(s) in the circuit board(s) 218 may "key" the entrance of the heat pipes such that the assembly of FIG. 22g could be affixed to this board by the friction of its pins 237 matching up with the array of small holes 238 in this figure. The small holes 238 contain the female receptacles (or sockets) that are themselves connected to circuit truces that ultimately control the LEDs. It is to be noted that instead of pins and sockets, "bumps" could take the place of either the pins, or sockets or both.

Figure 23B:
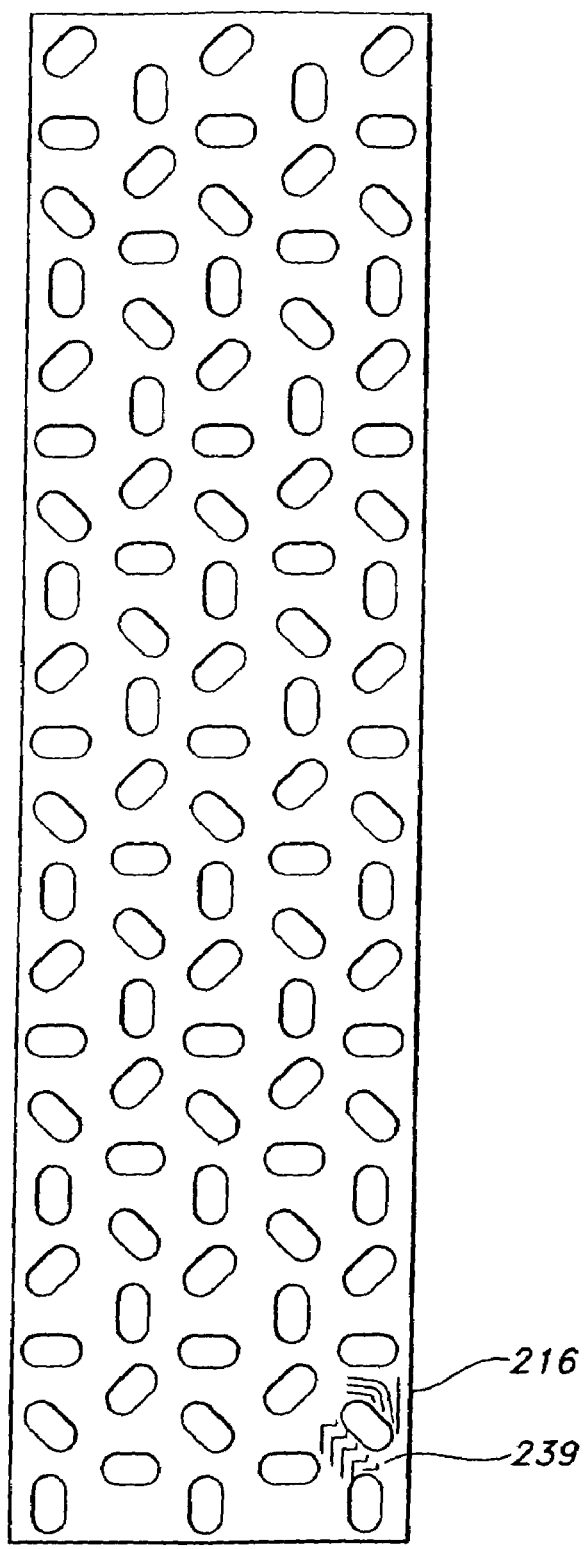

FIG. 23b depicts an alternate arrangement for the heat pipe 64 ovals of FIG. 23a, an even more tortuous path for more turbulence between the preferably oval heat pipes. Round or other shaped heat pipes 64 may be used. Note the sockets 239 for pins 237 and traces to the sockets.

Figure 24:
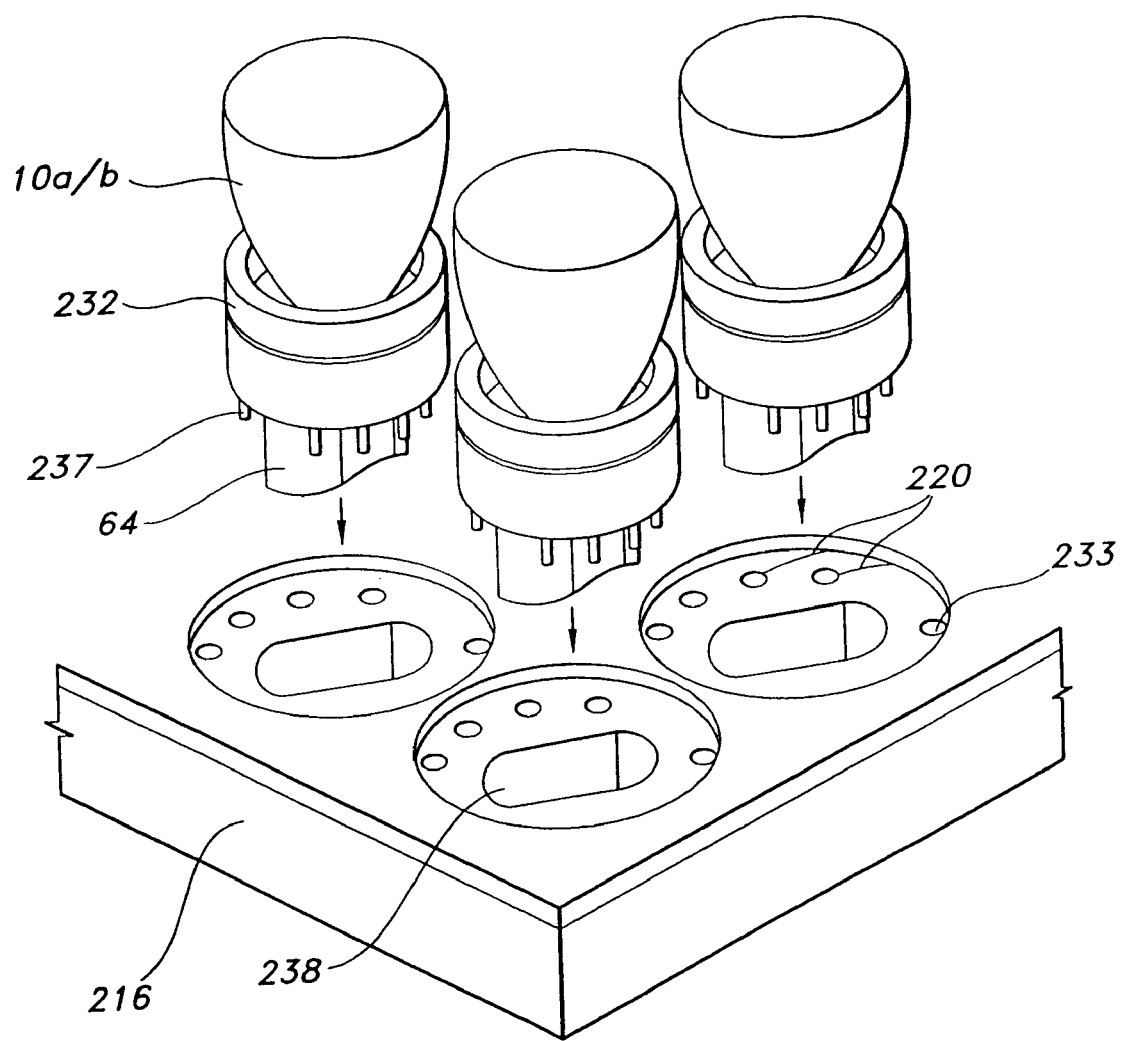

FIG. 24 shows the LED (or laser diode or VCSEL array) assemblies of FIG. 22g being inserted into the circuit board assembly 216 of FIG. 23a. Note the oval shaped holes 238 that "key" and/or accept the oval heat pipes 64. The optional blind circular holes 221 in the top portion of the circuit board 216 accept the strengthening rings of the assemblies of FIG. 22g. Also, note the circuit traces 220 (only a few are shown for clarity) on circuit board 216 beneath the top board layer that contains the blind circular holes 221. Also the holes 238 contain the female receptacles for pins 237. The receptacles in 238 are connected to the traces 220 and the traces lead to a controller and/or power supply. The assembly of FIG. 24 is preferably used in a large video display or sign and each LED 10 on each heat pipe 64 is thought of as a "pixel" that is individually addressable. Each "pixel" may also have nine (for example only) individually addressable LEDs. The waste energy from the LEDs 10 is carried straight back through the heat pipes 64 and distributed across the circumferential surface area of the heat pipes 64 which is somewhat analogous to a the operation of a "pin" in a "pin-fin" heat sink. In the most preferable embodiment, a red, a green, and a blue LED 10 are mounted on or in the region immediately adjacent to the tip of the heat pipe 64 and each are electrically individually addressable. It is understood that multiple red, green, or blue LEDs may be mounted together and/or in any combination and have different centered wavelengths. These assemblies may also be used for many other applications, an example of which is medical devices. The traces 220 are also shown in FIG. 23b and the female holes 238 are also depicted and described in FIGS. 23a and 23b as well as this FIG. 24. Optionally a second strengthening board 240 on top of the board 216 has circular, rather than oval holes. These circular holes accommodate the round strengthening ring(s) 232.

Figure 25:
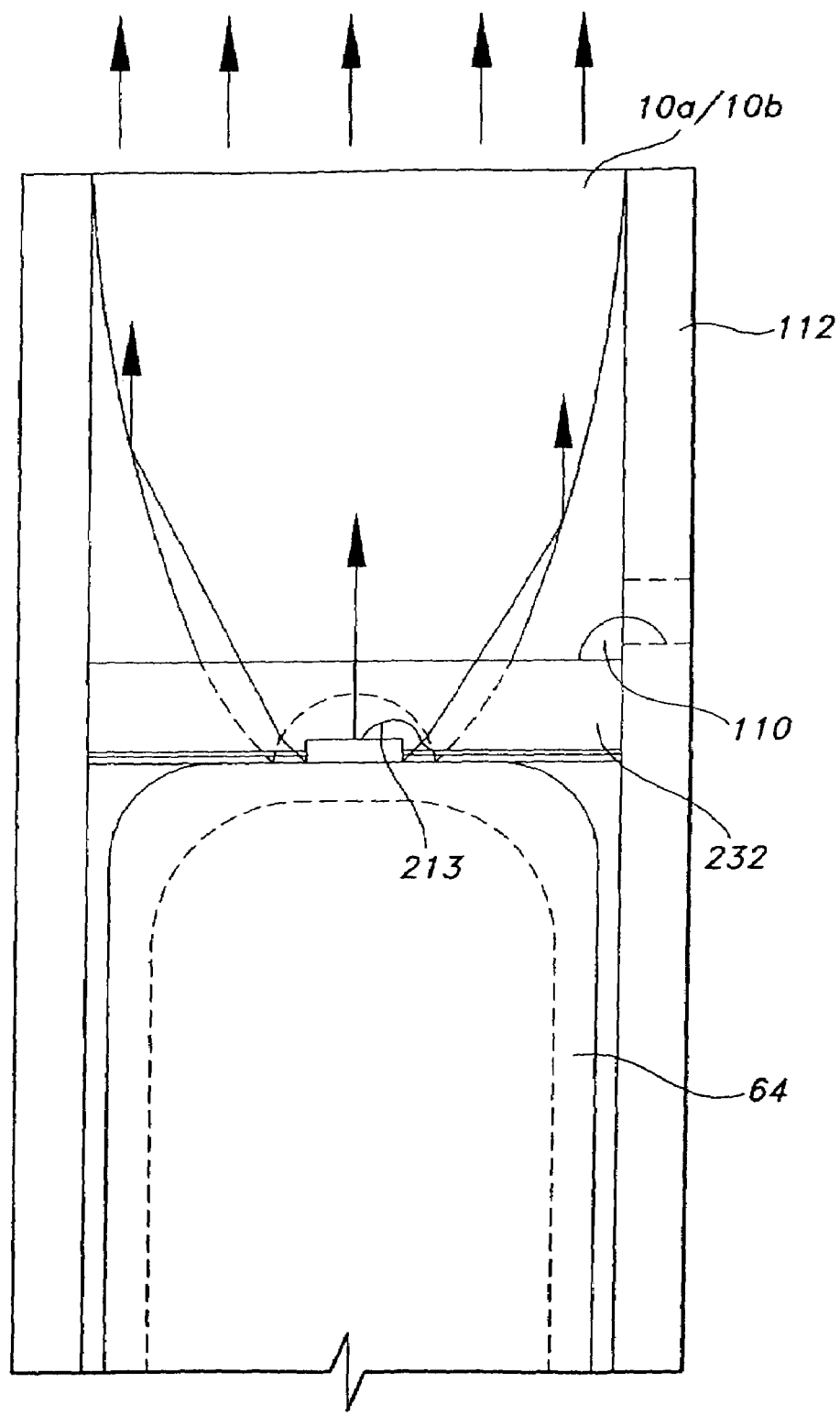
FIG. 25 shows the assembly of FIG. 22b and the assembly of FIG. 22d with a protective outer sleeve.

FIG. 25 shows the assembly of FIG. 22b and FIG. 22d within an outer sleeve 112. The sleeve 112 has a hole through it by which a conductive adhesive 234 or solder 110 may be injected. This adhesive can then serve as an electrical conduction path between the conductive ring 232 of FIG. 22 and the conductive sleeve 112. This sleeve may be made from aluminum and it may be anodized or electrophoretically coated which serves as an electrically isolating coating. However, the through hole 112 is not coated, thereby the adhesive can contact an electrically conducting surface. The sleeve 112 and the heat pipe 64 are electrically insulated from each other by way of example in this FIG. 25. For purposes of drawing orientation, the reflector/lens 10a/10b is shown with the arrows depicting light emitting from the LED or LD device. In this figure, the heat pipe 64 is the "anode" and the current goes through the LED and through the wire 213 and then into the conductive ring 232 and then into the conductive adhesive 234 and finally into the conductive sleeve 112. The heat pipe 64 is connected to the "positive" battery or power supply terminal and the sleeve 112 is connected to the "negative" battery or power supply terminal, the polarity may be reversed depending on polarity of LED die/dice.

Figure 26A:
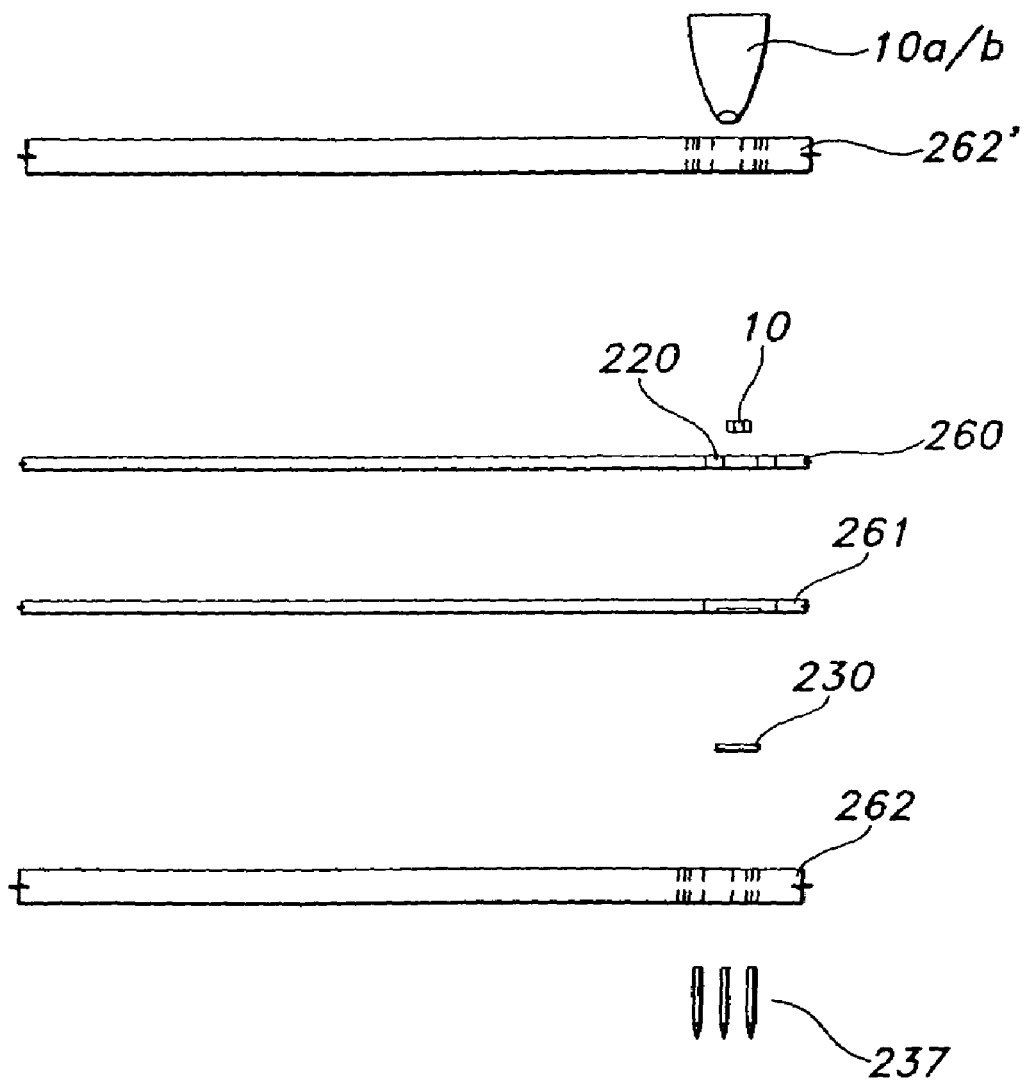
FIG. 26a illustrates a perspective view of various parts of the circuit board device prior to packaging and assembly with LEDs.

In an additional embodiment, there is shown LED packages according to the invention manufactured and assembled using Printed Circuit Board (PCB) techniques described herein. Referring to FIG. 26a, there is shown a first layer 260 made preferably of polyimide and have a preferred thickness of around 0.001" to 0.002". This layer 260 may have photo imaged and etched metal, preferably copper, circuit traces 220. The first layer 260 may be in sheet form of approximate dimensions 12" to 18" and many, if not all succeeding layers may have the same approximate dimensions. This first layer 260 is bonded to the second layer 261 which is also preferably polyimide and is approximately 0.004" thick. This layer 261 may have a square hole laser cut in it to accommodate the eventual insertion of a heat spreader 230. This heat spreader 230 is preferably of a highly heat conductive material such as CVD diamond as mentioned before. LEDs or LDs 10 may be bonded to the heat spreader 230 and have wire bonds leading to traces 220. Stiffeners 262 and 262' may be bonded to layers. These stiffeners are also preferably of a polyimide material which is available in thicknesses around 0.040". These stiffeners could also be injection molded plastic and assembled individually rather than in board format. The stiffeners may be assembled individually if the layers 260 and 261 are manufactured with a real-to-real or roll-to-roll flex circuit manufacturing process. The lens and/or reflector 10 a/b may be bonded on or over the LEDs or LDs 10 while all layers 260, 261, 262 and 262' are in "panel" format, i.e., components are not yet singulated from the "panel" or "board". All the layers may be registered (aligned) to one another as they are bonded. The reflectors, or lenses, may be assembled in trays to match the center to center spacing of the LEDs 10 or LD devices on the panels (boards). The tray of reflectors or lenses 10 a/b may then be lowered into the panel of LED/LD devices. In such a fashion the reflectors or lenses 10 a/b may be assembled over or on the LED/LD devices in an array format to affect high volume manufacture. Fins 237 may also be added while in panel format. Solder bumping, stud bumping, etc., may also be accomplished while in panel format. After all layers and components have been bonded and/or assembled, the individual LED or LD devices may be laser singulated from the panel. A UV laser system may be employed for this task. The LED or LD devices (or "packages") are singulated by the laser cutting through all of the layers and thereby separating the devices from the panel of laminated layers. Polyimide is a preferred layer material because it is laser cut very cleanly and efficiently. FR4 or BT may also be used. Automated pick and place equipment, as well as adhesive dispense equipment, may be employed during all phases of assembly. The lenses/reflectors a/b may be arrayed on trays, on the UV tape electrostatic or vacuum chuck whether assembled in array/panel format or assembled individually using automated pick and place equipment.

Figure 26B:
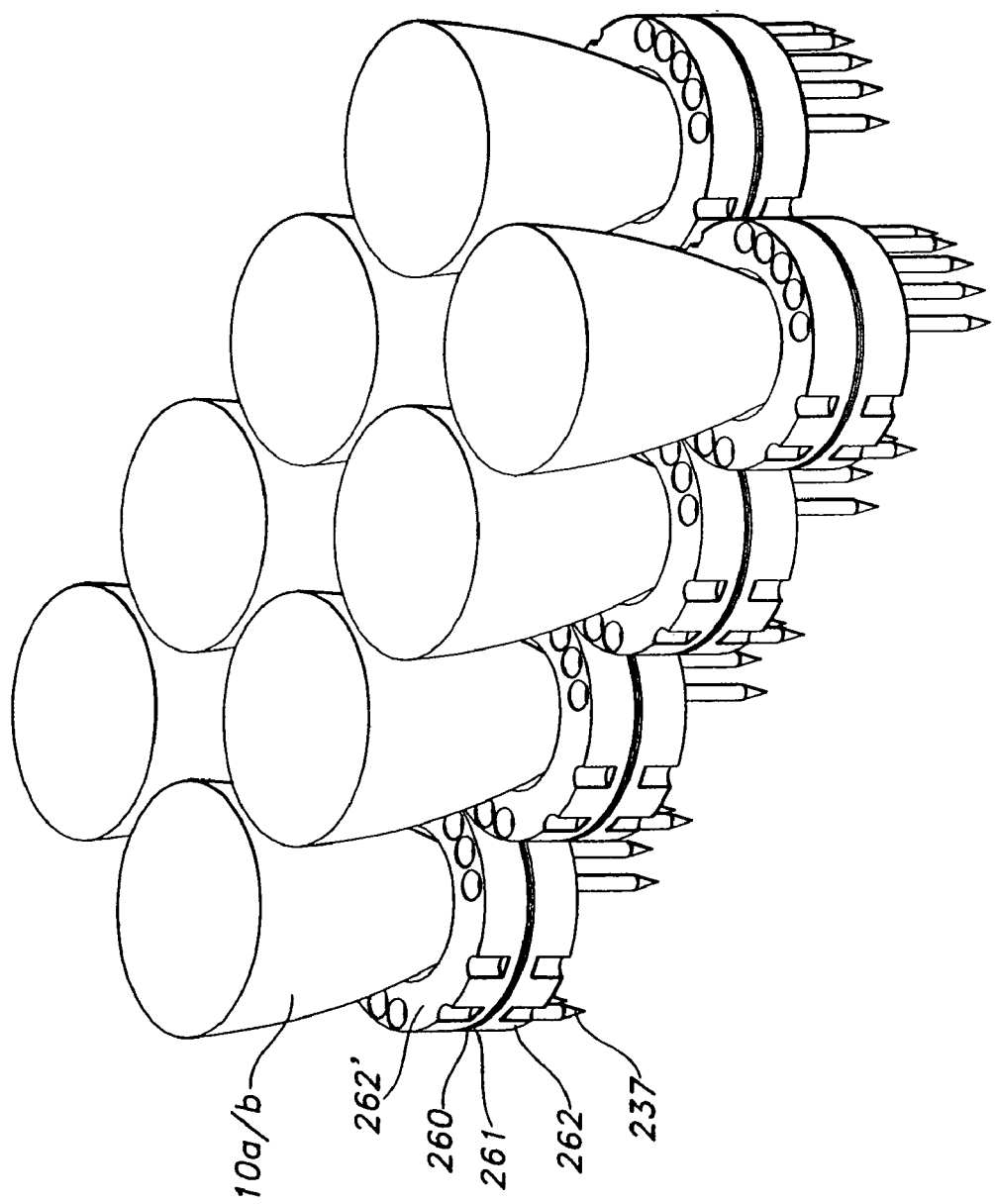
FIG. 26b shows an array of LED packages according to the present invention after the packages have been assembled and singulated.

FIG. 26b shows an array of LED packages manufactured according to the present invention after the packages have been assembled and then singulated by laser-cutting.

Figure 26C:
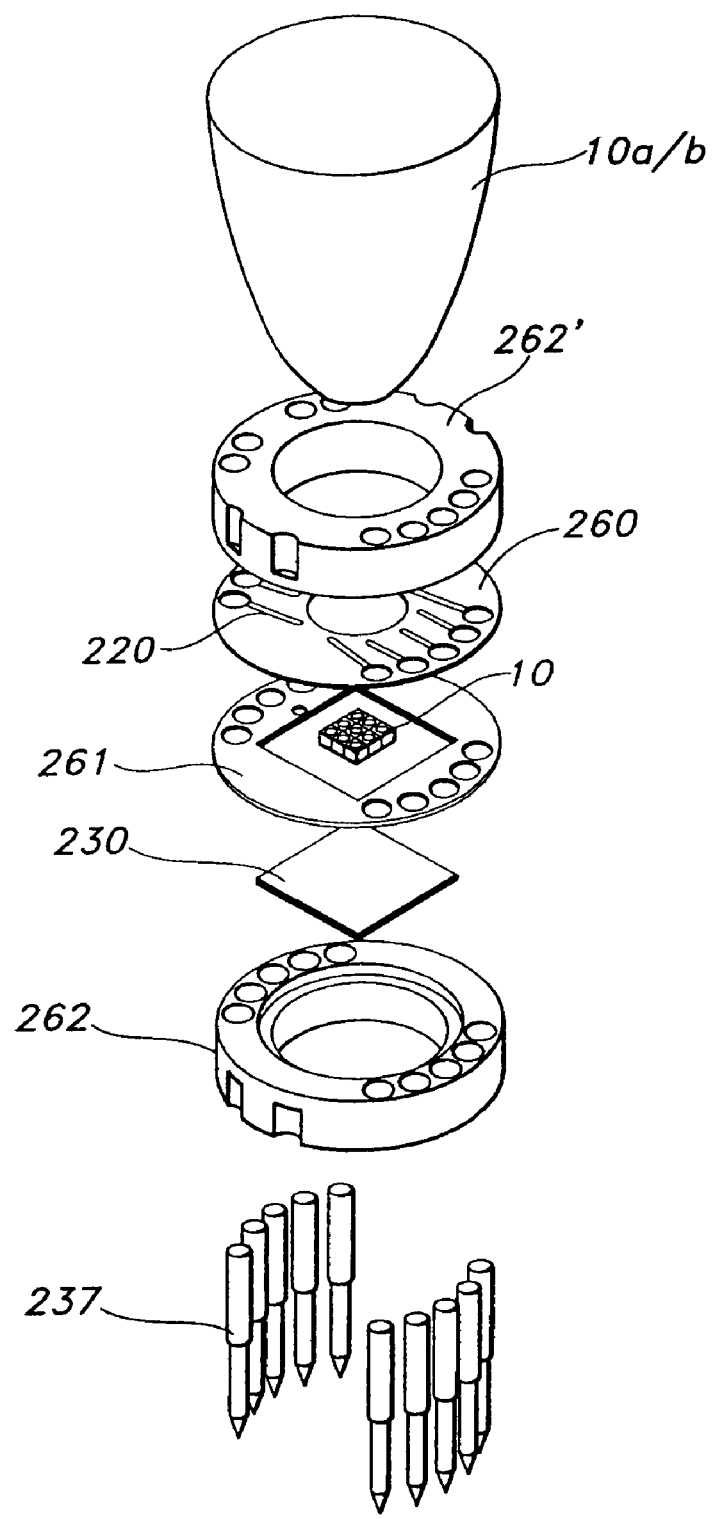
FIG. 26c shows an exploded view of one post-singulation LED package according to the present invention.

FIG. 26c is an exploded view of one post-singulation LED package manufactured according to the present invention.

Figure 27:
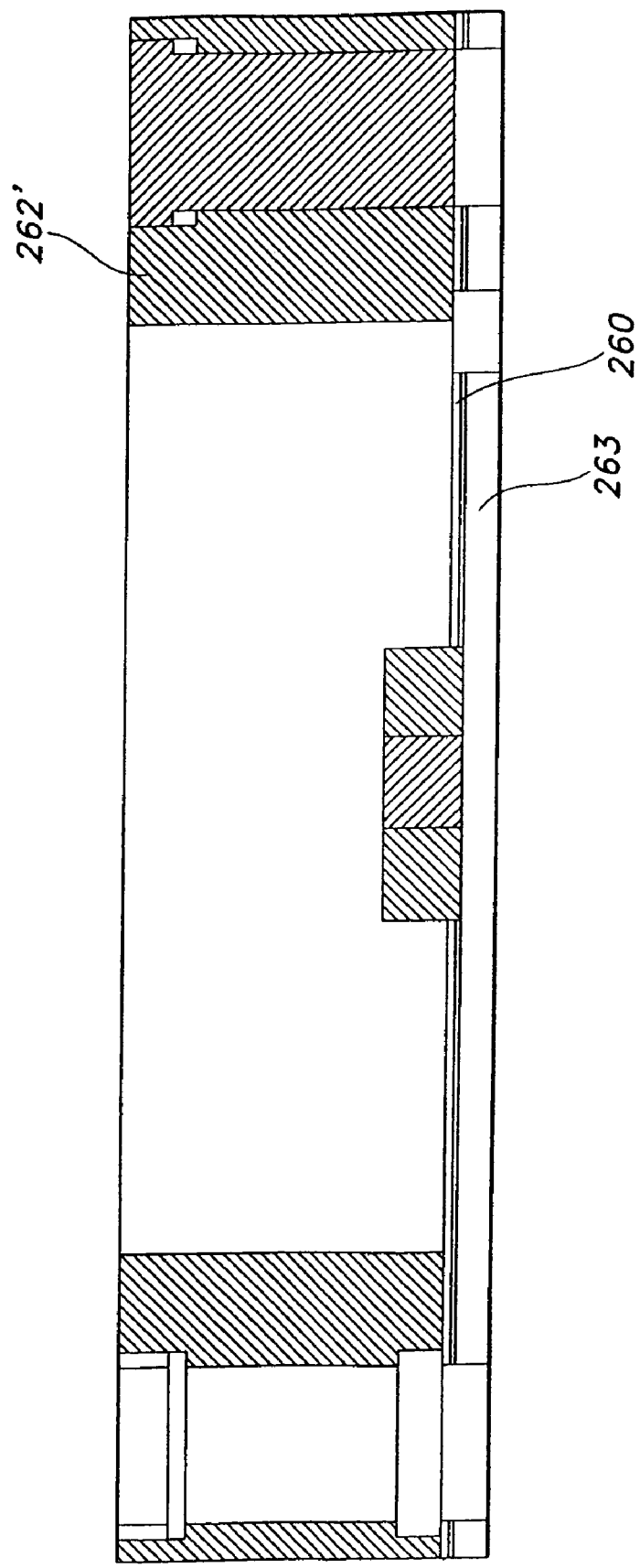
FIG. 27 shows an expanded view of an individual LED package of FIGS. 26a, 26b and 26c.

FIG. 27 shows an individual device similar to devices shown in FIGS. 26a, 26b and 26c, except that the preferably polyimide circuit layer 260 is bonded not to another polyimide layer 261 (that has a cut out in it for heat spreader 230 as shown in FIGS. 26a and 26c), but is instead bonded to a monolithic highly thermal conductive heat spreader without any surrounding polyimide layer 261. Layer 263 can be pre-laser cut diamond and assembled using pick and place equipment while the LED devices still exist in panel format i.e., stiffener layer 262' and polyimide circuit layer 260 have not been laser separated from the panel, or layer 263 may be a large wafer, (preferably 1 foot diameter and this wafer may be bonded to the polyimide circuit layer 260' which is also bonded to stiffener layer 262'. Both layers 260 and 262' may also preferably be 1 foot diameter, similar to 1 foot diamond layers 263. Two one foot diamond layers 263 may preferably be bonded on to polyimide layer 260 or layer 262', as layer 260 is optional if circuit traces 220 are deposited directly on 263. It should be understood that circuit traces directly deposited onto layer 263 by means such as masks or photolithography is an excellent means for providing circuit traces and no polymer layer is required.

Figure 27A:
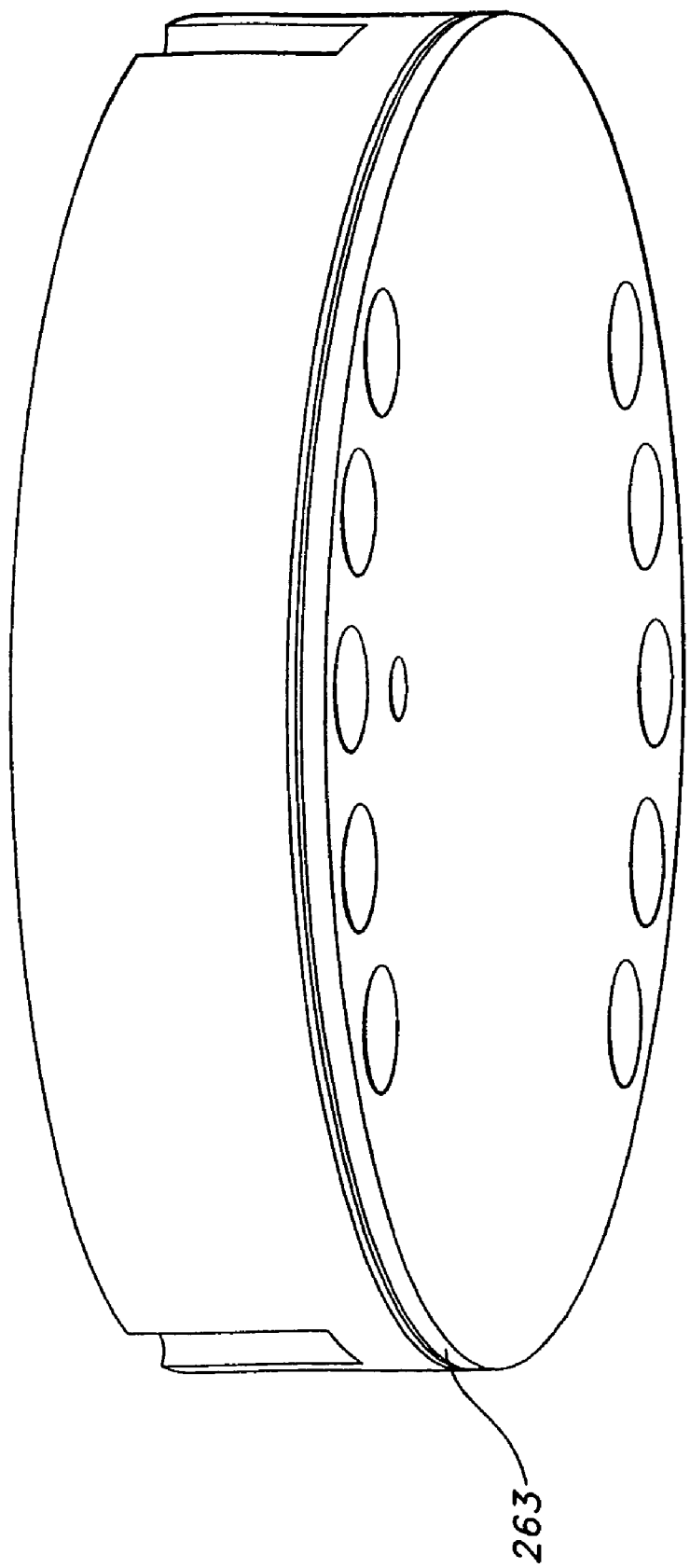
FIG. 27a shows a bottom-side view of the individual LED package of FIG. 27 with the bottom layer including a highly thermally conductive material.

FIG. 27a shows a bottom-side view of the LED package of FIG. 27 wherein the no cut-out bottom layer 263 is a highly thermally conductive material such as diamond. Holes through this layer 263 may be laser drilled and plated through after a first conductive metal "seed" layer is first deposited by vapor or liquid means.

Figure 28A:
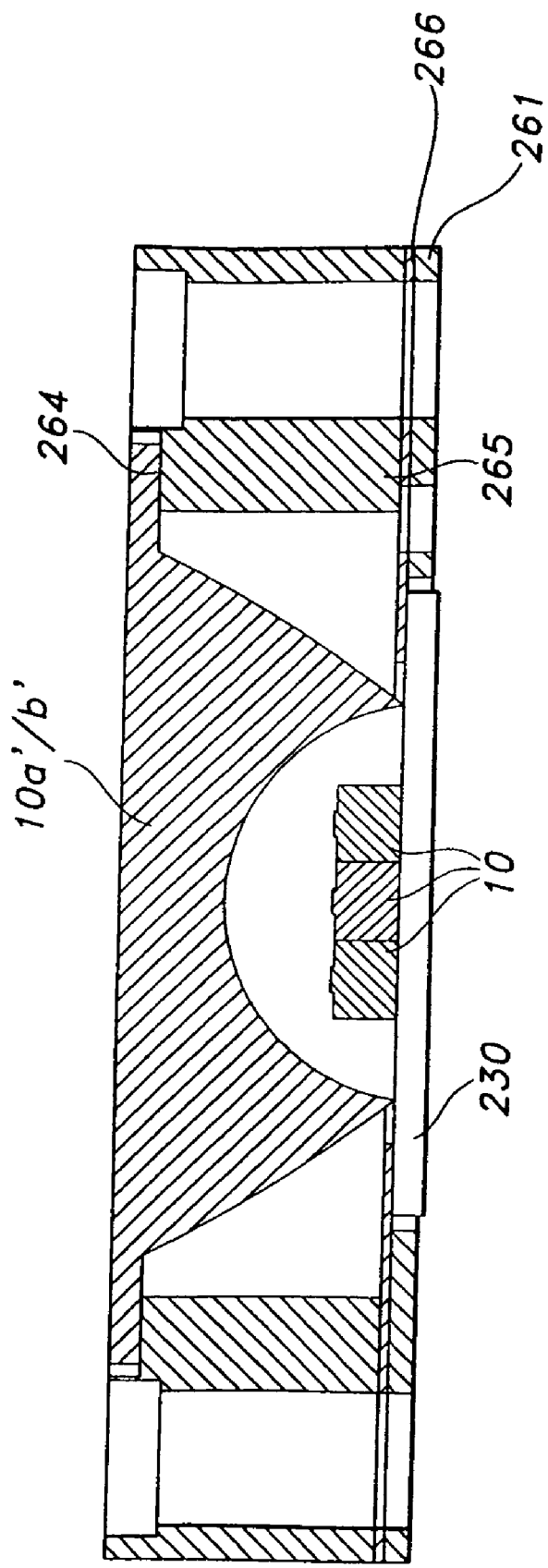
FIGS. 28a and 28b show a side view of the individual LED package of FIG. 27.

FIG. 28a shows a side view of the LED packaged device of FIG. 27. The TIR reflector 10 a/b his its elliptical or parabolic side wall portion significantly shortened in overall length as opposed to that of reflector 10 a/b in FIG. 26a. This shortening in length increases the output divergence of the light as opposed to a longer side wall reflector. Also, this figure depicts a package that is more "hermetic" in its environmental sealing from contaminants. This is accomplished by the top surface of reflector 10 a/b having a larger flat plate-like integral "hat" 264. This "hat" 264 sits down in a counter bore in stiffening ring 265. Note the LEDs 10 for the purpose of drawing orientation. Epoxy or solder or other adhesive is used to seal "hat" 264 to stiffening ring 265. Element 266 is also a polyimide circuit layer. The heat spreader is denoted by 230.

Figure 28B:
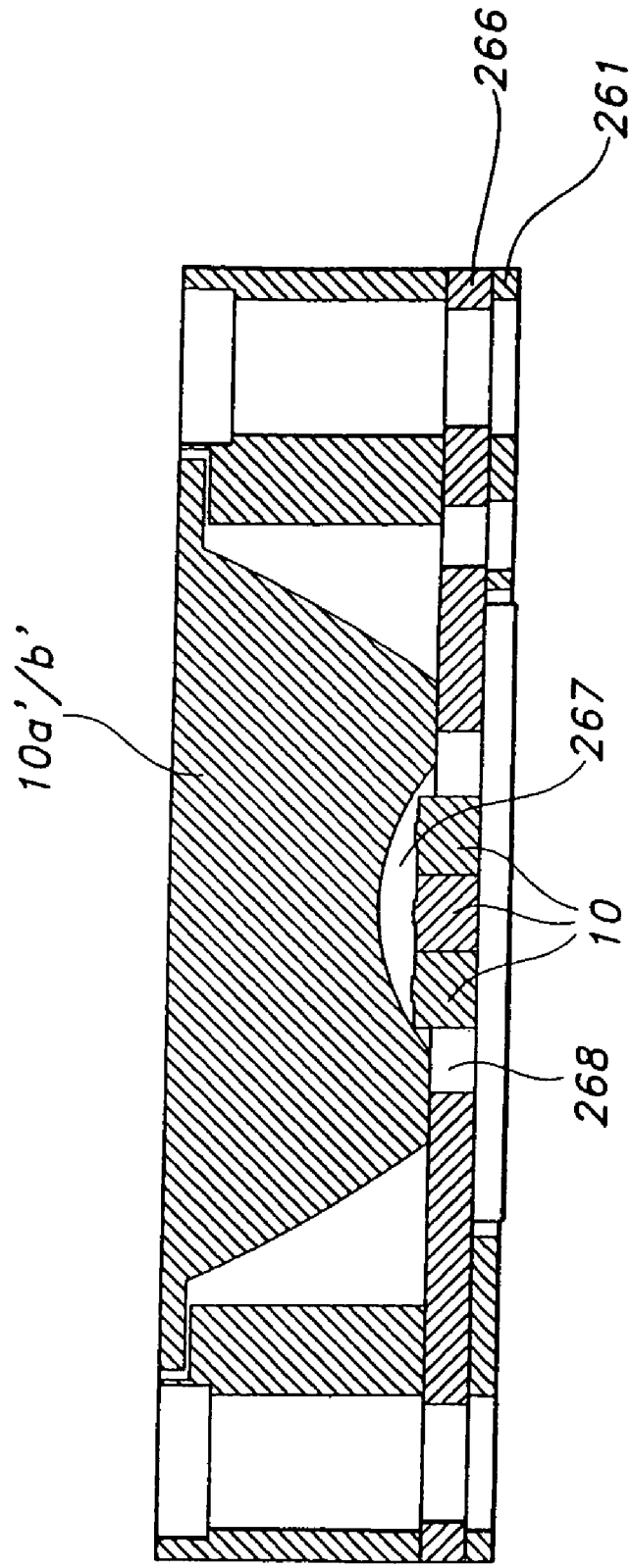

FIG. 28b depicts an LED Package similar to that in FIG. 28a, except the polyimide or other non-conductive material 266 is of greater thickness and the concave hemispherical portion of reflector 10a/10b' is of less curvature. The circuit layer 266 is nearly as thick as the LEDs 10 are. The reason for this is that the LEDs 10 shown have the epitaxial layer 267 an top of the LED 10 as opposed to a "flip-chip" structure wherein the epi layers are on the bottom of the chip, where it is bonded to a submount or heat spreader 230. Since the LED structure is on top, the circuit layer 266 may be thicker without absorbing much emitted light out of the sides of the chip. Primarily the advantage is that the excess index matching gel 2 that surrounds the chip(s) is less likely to flow on the sides of the TM reflector 10 a/b and destroy the TIR properties i.e., couple out light through the sides because the gel 268 has a cavity to flow into that is not in such close proximity to the reflector wall. The cavity is defined by the thick (high) side walls of the square cavity that is laser cut-out or punched in circuit layer 266. The heat spreader 230 maybe thicker than layer 261. As such it would "stick out" a little and may give clearance for solder bumps used as connection devices near the outer diameter "periphery" of the device. This clearance helps to alleviate some stress in the solder bumps if the package is not so firmly pulled down onto the circuit board. The layer 267 may be of essentially the same thickness as layer 262. Lastly layer 267 may be thinner than layer 262 which would allow extra room for the bonding means of layer 267 to the heat pipe 64 or circuit board 216. This extra room can alleviate stress in the bond layer.

Figure 29:
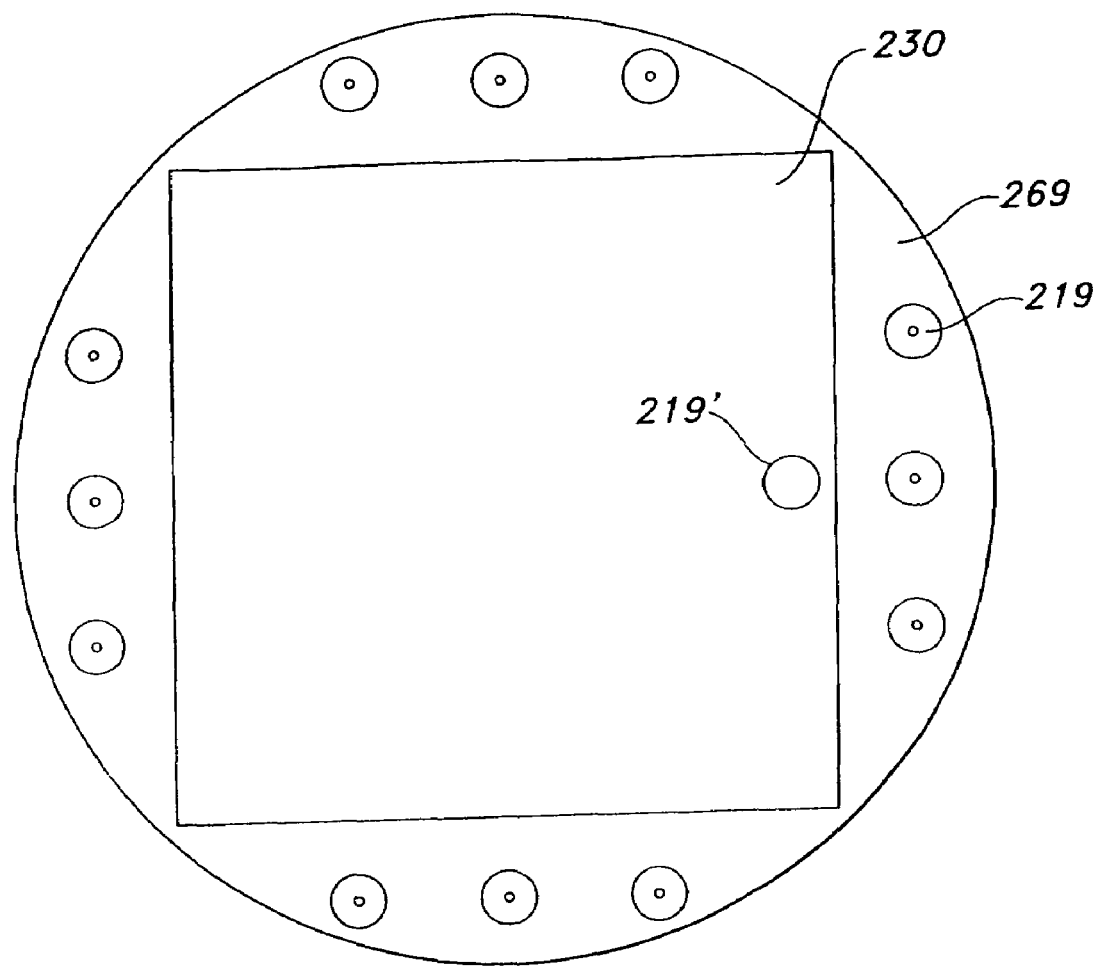
FIG. 29 shows a bottom-side view of the individual LED package of FIG. 27 with the heat spreader.

FIG. 29 shows a bottom-side view of an LED Packaged device of FIG. 27 wherein the hypotenuse of the heat spreader 230 is almost as long as the cord of the diameter of the captive polymer layer 269. This greater surface area of the heat spreader 230 allows a greater area to conduct heat through in a small diameter package, which by nature has a smaller diameter polymer layer ring 269. If nine individually addressable LEDs are employed, there is an inherent need for nine conductors plus a ground. These nine conductors may be placed through holes 219 through the heat spreader 230. Importantly, three such conductors are located symmetrically on each of the four sides of the heat spreader 230. The hole(s) 219 are connected to circuit traces found on top of the heat spreader 230. These traces are then wire bonded to the LEDs or LDs 10. These hole(s) 219 may be connected to a circuit board that controls the packaged device via solder bumps on the device and/or board, conductive (anisotropic or isotropic) adhesive bumps on the device and/or board, stud bumps an the, device and/or board, pins—preferably compliant on the device and/or board, solder paste the device and/or board, solder pads or preforms on the device and/or board, or anisotropic conductive film. Conductive adhesive or solder paste may be injected in holes 219. This is by no means meant to be exhaustive or all inclusive. In hole 219 a solder ball may be partially inserted in this hole and reflowed slightly with a laser beam to hold solder ball in place until final assembly/reflow operation. Pac Tech, Inc. (Santa Clara, Calif.) manufactures equipment that is optimal for this operation. Any hole may have a solder ball placed in it, as well as anywhere on the metalized surface of the heat spreader. Solder balls may also be placed by screen printing or electrochemical means, as well as adhesive means.

Figure 30A:
FIG. 30a illustrates a perspective view of a flattened heat pipe with LEDs.

FIG. 30a depicts a flattened flexible heat pipe 64 With LED's or LD's 10 bonded to it. This heat pipe could be less than 1 mm or also be thicker than 1 mm. One or more LEDs or LDs 10 may first be mounted onto a submount, individually or collectively i.e., monolithic submount. The heat pipe 64 may conduct electricity and, as such, be either an anode or a cathode. Arrows from LEDs 10 depict light emission. The LEDs 10 may be in series, or in parallel or be individually addressable. This flexible device may be encapsulated in a transparent polymer. It may be used as a strap like device to wrap around a human or animal body part for light therapy. This same purpose may result from the use of device in FIG. 30b. These flattened heat pipes are available from Furukawa Electric (Japan). The heat pipes may be of the "sheet" variation that are discussed in their press release of Apr. 11, 2003. These devices in FIGS. 30a, b, and c may be encapsulated in a transparent polymer (as shown in FIG. 30a) and IR LEDs or visible or UV LEDs may be used and the device may be strapped on to a body part with light shining into the body for pain management as well as diabetes relate neuropathy. Work in similar areas to this has been researched by Anodyne (Tampa, Fla., USA).

Figure 30B:
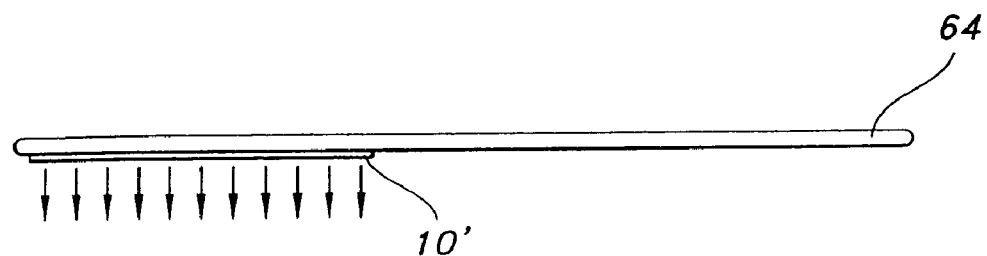
FIG. 30b illustrates a perspective view of a flattened heat pipe with LEDs.

FIG. 30b depicts the heat pipe of FIG. 30a. This heat pipe 64 has one or more organic Light Emitting Diode(s) (OLED) 10' bonded to it. This allows for a very thin structure and the heat pipe 64 is preferably longer than OLED 10' and transports the waste heat away from the OLED 10' to a heat sink 68 or dissipates the heat energy to ambient air.

Figure 30C:
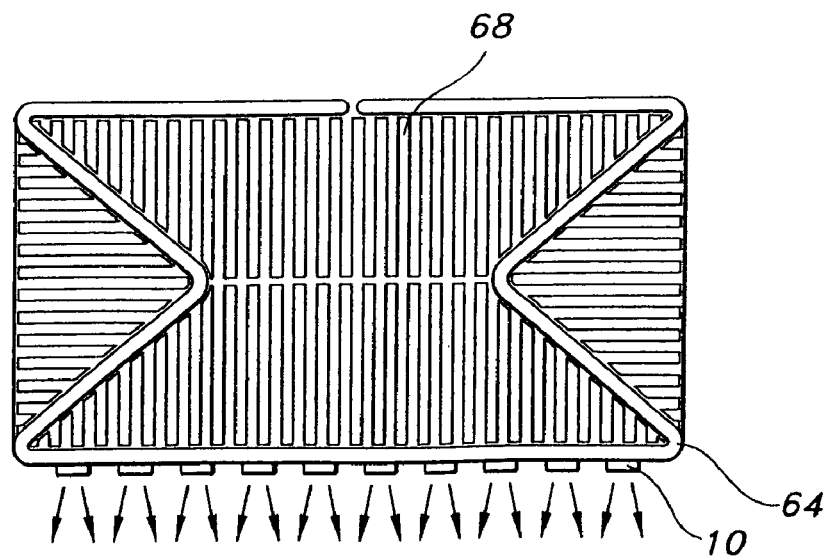
FIG. 30c illustrates a perspective view of the heat pipe bent around a finned sink.

FIG. 30c shows the heat pipe 64 bent around a finned heat sink 68. This heat sink may be made LIP of one or more extruded, molded, or machined heat sink(s) 68. The finned heat sinks 68 allow for more surface area for the heat from the LED device(s) 10 to be dissipated, through either natural or forced air convection. The device in the drawing may used for applications requiring a large emitting area with or without corresponding high (10 W or greater) output power. An OLED 10' may be used where LED 10 is shown. High output power may be used in various applications like LED/LD hair removal, wrinkle removal, pain management, PDT, carpal tunnel syndrome, and arthritis treatment.

Figure 31A:
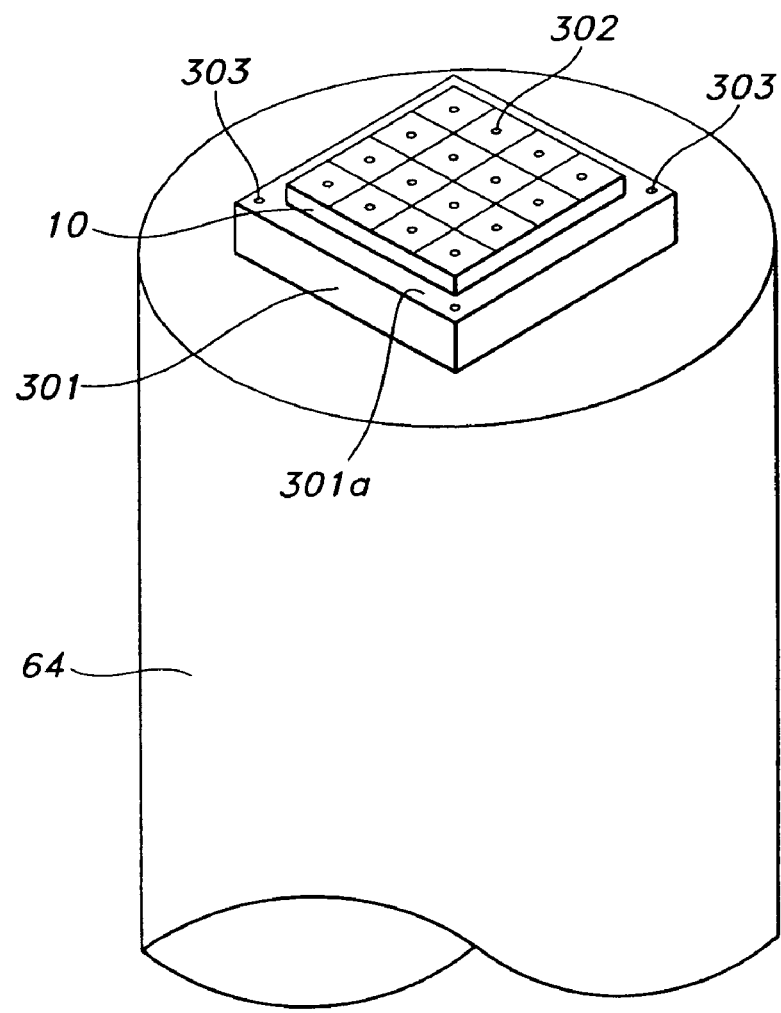
FIGS. 31a and 31b illustrate a perspective view of an array of LEDs bonded on a diamond substrate with a heat pipe according to an alternate embodiment of the present invention.

Referring to FIG. 31a, there is shown an array of LEDs 10 on a diamond submount 301 which is then bonded to a heat pipe 64. The diamond submount 301 is non-conductive, although it could be doped with boron to make it electrically conductive. The top surface 301a of the diamond 301 is metalized. This metalized layer serves as the "p" contact 303 metalization and is the common "p" contact for all of the LEDs (1-N in number) 10. "n" wire 10 302 and "p" wire 303 are shown only one for clarity. The LEDs 10 in this embodiment are preferably "metal-backed" LEDs, but various other LEDs may be used. This depiction is ideal for use in various applications preferably without a lens. A transparent flat (planar) window is preferred.

Figure 31B:
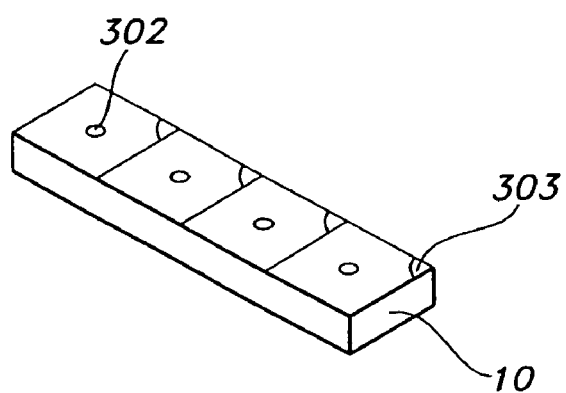

FIG. 31b depicts an array of four (although 1-N may be used) LEDs 10. In this embodiment, the "n" 302 and "p" 303 contacts are on the same side of the chip and the chips are connected in electrical series. This array may be placed on a heat pipe 64 similar to FIG. 31a.

All the devices in this patent application can be used with blue (465 nm) light to activate photo initiators common in dental initiators. Or other chromophors or sensitizers may be employed in curing adhesives or composites or other substances, as well as used in devices that may or may not contain light sensitizers, chromophors, or photoinitiators. The devices of the present invention may be used in conjunction with a variety of different compositions which are curable using electromagnetic radiation, as described herein. For example, compositions which harden or crosslink to form coatings, sealants, adhesives or articles of manufacture may be subjected to radiation emitted from the inventive devices to effectuate hardening or polymerizing. A wide variety of materials and compositions may be employed. For example, compositions including polyolefins, acrylates, epoxies, urethanes, polyesters, acrylimides, cyanoacrylates, silicones, polyamides, polyimides, polyvinyl compounds, latex compounds, among others, may be cured using radiation emitted from the present inventive device. These compounds rely on a variety of different chemical mechanisms to harden or polymerize. Generally, the ability to polymerize using light radiation, includes the use of compounds or complexes, which initiate or induce or otherwise accelerate the polymerization process. Frequently, one or more of these additional compounds, usually referred to as photoinitiators, photosensitizers or chromophors, are added to the polymerizable material to enhance both the speed and/or thoroughness of the cure.

The preferred embodiments described herein are intended in an illustrative rather than a limiting sense. The true scope of the invention is set forth in the claims appended hereto.

What is claimed is:

1. A lighting device comprising:
   a conductive patterned circuit material layer;
   at least one heat sink; and
   a light emitting device mounted to the at least one heat sink, the light emitting device electrically connected to the conductive patterned circuit material layer;
   wherein the at least one heat sink is in communication with the conductive patterned circuit material layer; and
   wherein the at least one heat sink is in thermal communication with a phase change material that changes phases between a solid and a liquid;
   wherein a conductive material is in thermal communication with the at least one heat sink and the phase change material;
   wherein the conductive material is dispersed throughout and in communication with the phase change material thereby further dissipating heat through the phase change material wherein the conductive material is a conductive fibrous material.

2. The lighting device of claim 1 wherein the at least one heat sink is a conductive patterned heat spreader layer.

3. The lighting device of claim 2 wherein the conductive patterned heat spreader layer is mounted to a heat pipe.

4. The lighting device of claim 1 wherein the at least one heat sink is a heat pipe.

5. The lighting device of claim 1 wherein an area between the light emitting device and the heat sink is free from a thermally resistive polymeric layer.

6. The lighting device of claim 1 wherein the conductive patterned circuit material layer has an aperture, at least one light emitting device receivable within the aperture.

7. The lighting device of claim 1 wherein the conductive fibrous material is wool.

8. A lighting emitting apparatus comprising:
   a fluid containing heat pipe having an evaporating end and a condensing end;
   a light emitting device mounted directly on the evaporating end of the heat pipe;
   a cone of light emitting from the light emitting device, the cone having a cone axis; and
   control circuitry capable of controlling electrical current transmission to the light emitting device;
   wherein upon the evaporating end of the heat pipe being expose to heat produced by the light emitting device, the fluid in the evaporating end vaporizes and flows to the condensing end;
   wherein upon reaching the condensing end, the vaporized fluid condenses and returns to the evaporating end; and
   wherein the light ray along the cone axis moves in a substantially parallel and opposite direction to the thermal energy moving along at least a portion of the vapor cavity axis.

9. The lighting apparatus of claim 8 and further comprising:
   a power supply for powering the control circuitry.

10. The lighting apparatus of claim 8 wherein the control circuitry being part of a power supply.

* * * * *